US008178759B2

(12) United States Patent
Morell et al.

(10) Patent No.: US 8,178,759 B2
(45) Date of Patent: *May 15, 2012

(54) BARELY WITH REDUCED SSII ACTIVITY AND STARCH AND STARCH CONTAINING PRODUCTS WITH A REDUCED AMYLOPECTIN CONTENT

(75) Inventors: Matthew Kennedy Morell, Aranda (AU); David Topping, Victor Harbor (AU); Ian Leslie Batey, Hornsby Heights (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/800,143

(22) Filed: May 10, 2010

(65) Prior Publication Data

US 2010/0330253 A1 Dec. 30, 2010

Related U.S. Application Data

(63) Continuation of application No. 10/416,439, filed as application No. PCT/AU01/01452 on Nov. 9, 2001, now Pat. No. 7,888,499.

(30) Foreign Application Priority Data

Nov. 9, 2000 (AU) .................................. PR1370
Nov. 9, 2000 (AU) .................................. PR1371
Nov. 9, 2000 (AU) .................................. PR1372
Nov. 9, 2000 (AU) .................................. PR1373

(51) Int. Cl.
*A01H 5/10* (2006.01)
*A01H 5/00* (2006.01)
*C08B 30/00* (2006.01)
*A21D 13/00* (2006.01)

(52) U.S. Cl. .......... 800/320; 800/295; 127/65; 426/549; 435/99

(58) Field of Classification Search ........................ None
See application file for complete search history.

(56) References Cited

U.S. PATENT DOCUMENTS

| | | | |
|---|---|---|---|
| 3,690,896 A | 9/1972 | Tarasewitz et al. | |
| 4,770,710 A | 9/1988 | Friedman et al. | |
| 5,051,271 A | 9/1991 | Iyengar et al. | |
| 5,792,920 A | 8/1998 | Bridges et al. | |
| 6,013,861 A | 1/2000 | Bird et al. | |
| 6,083,547 A | 7/2000 | Katta et al. | |
| 6,303,174 B1 | 10/2001 | McNaught et al. | |
| 6,307,125 B1 | 10/2001 | Block et al. | |
| 6,376,749 B1 | 4/2002 | Broglie et al. | |
| 6,483,009 B1 | 11/2002 | Poulsen et al. | |
| 6,730,825 B1 | 5/2004 | Goldsbrough et al. | |
| 6,734,339 B2 | 5/2004 | Block et al. | |
| 6,897,354 B1 | 5/2005 | Yamamori et al. | |
| 6,903,255 B2 | 6/2005 | Yamamori et al. | |
| 6,916,976 B1 | 7/2005 | Li et al. | |
| 7,001,771 B1 | 2/2006 | Morell et al. | |
| 7,009,092 B1 | 3/2006 | Jane et al. | |
| 7,041,484 B1 | 5/2006 | Baga et al. | |
| 7,365,189 B2 | 4/2008 | Block et al. | |
| 7,521,593 B2 | 4/2009 | Regina et al. | |
| 7,667,114 B2 | 2/2010 | Morell et al. | |
| 7,700,139 B2 | 4/2010 | Bird et al. | |
| 7,700,826 B2 | 4/2010 | Morell et al. | |
| 7,790,955 B2 | 9/2010 | Li et al. | |
| 7,812,221 B2 | 10/2010 | Regina et al. | |
| 7,888,499 B2* | 2/2011 | Morell et al. | ................. 536/102 |
| 7,919,132 B2 | 4/2011 | Regina et al. | |
| 7,993,686 B2 | 8/2011 | Bird et al. | |
| 2004/0060083 A1 | 3/2004 | Regina et al. | |
| 2004/0199942 A1 | 10/2004 | Morell et al. | |
| 2004/0204579 A1 | 10/2004 | Block et al. | |
| 2005/0071896 A1 | 3/2005 | Regina et al. | |
| 2006/0010517 A1 | 1/2006 | Li et al. | |
| 2006/0035379 A1 | 2/2006 | Morell et al. | |
| 2006/0286186 A1 | 12/2006 | Bird et al. | |
| 2007/0300319 A1 | 12/2007 | Li et al. | |
| 2009/0226592 A1 | 9/2009 | Regina et al. | |
| 2011/0010807 A1 | 1/2011 | Morell et al. | |
| 2011/0059225 A1 | 3/2011 | Li et al. | |
| 2011/0070352 A1 | 3/2011 | Regina et al. | |
| 2011/0212916 A1 | 9/2011 | Bird et al. | |

FOREIGN PATENT DOCUMENTS

GB 2 360 521 9/2001

(Continued)

OTHER PUBLICATIONS

U.S. Appl. No. 12/881,040, filed Sep. 13, 2010, Regina et al.

(Continued)

*Primary Examiner* — Brent T Page

(74) *Attorney, Agent, or Firm* — John P. White; Gary J. Gershik; Cooper & Dunham LLP

(57) ABSTRACT

Barley with reduced SSII activity has a starch structure with reduced amylopectin content and a consequent high relative amylose content. Additionally the grain can have a relatively high β glucan content. The structure of the starch may also be altered in a number of ways which can be characterized by having a low gelatinzation temperature but with reduced swelling. The viscosity of gelatinized starch of the starch is also reduced. There is a chain length distribution of the amylopectin content and a low crystallinity of the starch. The starch is also characterized by having high levels of lipid associated starch exhibiting very high levels of V form starch crystallinity. The dietary fiber content of the starch is high. This has desirable dietary and food processing characteristics.

14 Claims, 23 Drawing Sheets

FOREIGN PATENT DOCUMENTS

| WO | WO 97/22703 | 6/1997 |
| --- | --- | --- |
| WO | WO 99/14314 A | 3/1999 |
| WO | WO 00/15810 | 3/2000 |
| WO | WO 00/66745 A1 | 3/2000 |
| WO | WO 01/32886 | 5/2001 |
| WO | WO 01/62934 | 8/2001 |
| WO | WO 02/37955 | 5/2002 |
| WO | WO 02/101059 | 12/2002 |
| WO | WO 03/023024 | 3/2003 |
| WO | WO 03/094600 A1 | 11/2003 |
| WO | WO 2005/001098 | 1/2005 |
| WO | WO 2005/040381 | 6/2005 |

OTHER PUBLICATIONS

U.S. Appl. No. 12/799,013, filed Apr. 16, 2010, Bird et al.
U.S. Appl. No. 12/806,167, filed Aug. 6, 2010, Li et al.
Gillespie, K., Type 1 diabetes: pathogenesis and prevention, CMAJ, 2006, vol. 175, pp. 165-170.
Regina A., High-amylose wheat generated by RNA interference improves indices of large-bowel health in rats. 2006, PNAS, 2006 vol. 103, pp. 3546-3551.
Sun at al., The Two Genes Encoding Starch-Branching Enzymes IIa and IIb Are Differentially Expressed in Barley. Plant Physiol, 1998, 118:37-49.
Decision on Petition, issued Jul. 25, 2011 in connection with U.S. Appl. No. 10/416,439.
Patent Term Adjustment Petition, filed Apr. 14, 2011 in connection with U.S. Appl. No. 10/416,439.
Response to Amendment after Notice of Allowance, issued May 17, 2010 in connection with U.S. Appl. No. 10/416,439.
Amendment after Notice of Allowance, filed Mar. 22, 2010 in connection with U.S. Appl. No. 10/416,439.
Notice of Allowance, issued Dec. 22, 2009 in connection with U.S. Appl. No. 10/416,439.
Response to Non-Final Office Action, filed Sep. 2, 2009 in connection with U.S. Appl. No. 10/416,439.
Non-Final Office Action, issued Apr. 3, 2009 in connection with U.S. Appl. No. 10/416,439.
Decision on Petition, issued Mar. 13, 2009 in connection with U.S. Appl. No. 10/416,439.
Petition, filed Feb. 6, 2009 in connection with U.S. Appl. No. 10/416,439.
Final Office Action, issued Dec. 8, 2008 in connection with U.S. Appl. No. 10/416,439.
Response to Non-Final Office Action, filed Jul. 31, 2008 in connection with U.S. Appl. No. 10/416,439.
Non-Final Office Action, issued Mar. 31, 2008 in connection with U.S. Appl. No. 10/416,439.
Response to Non-Final Office Action, filed Dec. 13, 2007 in connection with U.S. Appl. No. 10/416,439.
Examiner Interview Summary, issued Nov. 30, 2007 in connection with U.S. Appl. No. 10/416,439.
Non-Final Office Action, issued Aug. 13, 2007 in connection with U.S. Appl. No. 10/416,439.
Applicant Interview Summary, filed Jul. 24, 2007 in connection with U.S. Appl. No. 10/416,439.
Examiner Interview Summary, issued Jul. 13, 2007 in connection with U.S. Appl. No. 10/416,439.
Notice of Appeal, filed Jun. 22, 2007 in connection with U.S. Appl. No. 10/416,439.
Advisory Action, issued Jun. 18, 2007 in connection with U.S. Appl. No. 10/416,439.
Examiner Interview Summary Record, issued Jun. 14, 2007 in connection with U.S. Appl. No. 10/416,439.
Response to Final Office Action, Filed May 24, 2007 in connection with U.S. Appl. No. 10/416,439.
Final Office Action, issued Jan. 22, 2007 in connection with U.S. Appl. No. 10/416,439.
Response to Non-Final Office Action, filed Sep. 6, 2006 in connection with U.S. Appl. No. 10/416,439.
Non-Final Office Action, issued Jun. 6, 2006 in connection with U.S. Appl. No. 10/416,439.
Response to Restriction Requirement, filed Feb. 1, 2006 in connection with U.S. Appl. No. 10/416,439.
Restriction Requirement, filed Dec. 8, 2005 in connection with U.S. Appl. No. 10/416,439.
Communication, filed Sep. 29, 2005 in connection with U.S. Appl. No. 10/416,439.
Non-Final Office Action filed Aug. 10, 2005 in connection with U.S. Appl. No. 10/416,439.
Decision to Grant a European Patent, issued by the European Patent Office on Jun. 15, 2011 in connection with European Patent Application No. EP 01983291.4.
Written Submission, filed Nov. 29, 2010 in connection with European Patent Application No. EP 01983291.4.
Written Submission, filed Nov. 2, 2010 in connection with European Patent Application No. EP 01983291.4.
Summons to Attend Oral Proceedings, issued Jun. 2, 2010 by the European Patent Office in connection with European Patent Application No. EP 01983291.4.
Reply to Communication from the Examining Division, filed Mar. 22, 2010 in connection with European Patent Application No. EP 01983291.4.
Result of Consultation, issued by the European Patent Office on Feb. 17, 2010 in connection with European Patent Application No. EP 01983291.4.
Reply to Communication from the Examining Division, filed Jun. 25, 2008 in connection with European Patent Application No. EP 01983291.4.
Communication from the Examining Division, issued by the European Patent Office on Oct. 15, 2007 in connection with European Patent Application No. EP 01983291.4.
European Search Report, issued by the European Patent Office on Jan. 14, 2005 in connection with European Patent Application No. EP 01983291.4.
European Search Report, issued by the European Patent Office on Jun. 28, 2011 in connection with European Patent Application No. EP 10183887.8.
Calvert et al., High Amylose Glacier Barley in Swine Diets. Nutritional Reports International, 1981, 23:29-36.
Schulman et al., Structural analysis of starch from normal and *shx* (shrunken endosperm) barley (*Hordeum vulgare* L.). Carbohydrate Research, 1995, 275:361-369.
Schulman and Kammiovirta, Purification of Barley Starch by Protein Extraction. Starch, 1991, 43(10):387-389.
Walker et al., J.T. Genetic Control of Abnormal Starch Granules and High Amylase Content in a Mutant of glacier Barley. Nature, 1969, 221:482-483.
Yoshimoto et al., Molecular Structure and Some Physiochemical Properties of High-Amylose Barley Starches. Cereal Chem, 2000, 77(3):279-285.
Zobel et al., Starch Gelatinization: An X-ray Diffraction Study. Cereal Chem, 1988, 65(6):443-446.
Zabel, H.F., Starch Crystal Transformations and Their Industrial Importance. Starch, 1988, 40(1): 1-7.
Zwar and Chandler, α-Amylose production and leave protein synthesis in a gibberellin-responsive dwarf mutant of 'Himalaya' barley (*Hordeum vulgate* L.). Planta, 1995, 197:39-48.
File History of U.S. Patent No. 7,812,221, Regina et al., issued Oct. 12, 2010 (U.S. Appl. No. 10/881,808, filed Jun. 20, 2004).
File History of U.S. Patent Application Publication No. 2011-0070352, Regina et al., published Mar. 24, 2011 (U.S. Appl. No. 12/881,040, filed Sep. 13, 2010).
File History of U.S. Patent No. 7,700,139, Bird et al., issued Apr. 20, 2010 (U.S. Appl. No. 11/324,063, filed Dec. 30, 2005).
File History of U.S. Patent Application Publication No. 2006-0286186, Bird et al., published Dec. 21, 2006 (U.S. Appl. No. 11/417,330, filed May 2, 2006).
File History of U.S. Patent No. 7,790,955, Li et al., issued Sep. 7, 2010 (U.S. Appl. No. 10/577,564, filed Apr. 27, 2006).
File History of U.S. Patent Application Publication No. 2011-0059225, Li et al., published Mar. 10, 2011 (U.S. Appl. No. 12/806,167, filed Aug. 6, 2010).
File History of U.S. Patent No. 7,001,771, Morell et al., issued Feb. 21, 2006 (U.S. Appl. No. 10/018,418, filed May 9, 2002).
File History of U.S. Patent No. 7,700,826, Morell et al., issued Apr. 20, 2010 (U.S. Appl. No. 11/231,599, filed Sep. 21, 2005).

File History of U.S. Patent No. 7,521,593, Regina et al., issued Apr. 21, 2009 (U.S. Appl. No. 10/434,893, filed May 9, 2003).

File History of U.S. Patent No. 7,919,132, Regina et al., issued Apr. 5, 2011 (U.S. Appl. No. 12/384,823, filed Apr. 9, 2009).

File History of U.S. Patent No. 7,667,114, Morell et al., issued Feb. 23, 2010 (U.S. Appl. No. 10/204,347, filed Feb. 20, 2002).

File History of U.S. Patent Application Publication No. 2011-0010807, Morell et al., published Jan. 13, 2011 (U.S. Appl. No. 12/707,437, filed Feb. 17, 2010).

First Official Action issued Jul. 24, 2007 by the Australian Patent Office in connection with Australian Patent Application No. 2006202440.

Office Action issued Jul. 10, 2008 by the Japanese Patent Office in connection with Japanese Patent Application No. 2002-540557, including English language translation.

Abel, G.J.W. et al., "Cloning and functional analysis of a cDNA encoding a novel 139 kDa Starch Synthase from Potato *Solanum tuberosum* L.)," Plant J. 10(6): 981-991 (1996).

Ainsworth, C. et al., "Expression, organization and structure of the genes encoding the waxy protein (granule-bound starch synthase) in wheat," Plant Mol. Biol. 22:67-82 (1993).

Anchikhorova ("Methods for carrying out pot experiments with granulated fertilizers", Doklady Vsesoyuznoi Akademii/Sel'skokhozyaistvennykh Nauk imeni V. I. Lenina (1971), vol. 8, pp. 20-22.

Baba, T. et al., "Identification, cDNA cloning and gene expression of soluble starch synthase in rice (*Oryza stativa* L.) Immature Seeds," Plant Physiol. 103:565-573 (1993).

Banks et al., "Studies on Starches of High Amylose Content," Starch 26: 289-300 (1974).

Batey and Curtin, "Measurement of Amylose/Amylopectin Ratio by High-Performance Liquid Chromatography," Starch 48: 338-344 (1996).

Blauth et al., "Identification of Mutator Insertional Mutants of Startch—Branching Enzyme 2a in Corn," Plant Physiology 125:1396-1405 (2001).

Boyer and Preiss, "Evidence for Independent Genetic Control of the Multiple Forms of Maize Endosperm Branching Enzymes and Starch Synthases," Plant Physiology 67: 1141-1145 (1981).

Buleon et al., "Starch Granules: Structure and Biosynthesis," International Journal of Biological Macromolecules 23: 85-112 (1998).

Craig et al., "Mutations in the Gene Encoding Starch Synthase IT Profoundly Alter Amylopectin Structure in Pea Embryos," The Plant Cell, vol. 10: 413-26 (1998).

Denyer, K. et al., "Identification of Multiple Isoforms of Soluble and Granule Bound Starch Synthase in Developing Wheat Endosperm," Planta 196: 256-265 (1995).

Dry, I. et al., "Characterization of cDNAs encoding two isoforms of granule-bound synthase which show differential expression in developing storage organs of pea and potato," Plant J. 2(2): 193-202 (1992).

Edwards et al., "Biochemical and Molecular Characterization of a Novel Starch Synthase from Potato Tubers," Plant J. 8(2): 283-294 (1995).

Flipse et al., "Introduction of Sense and Antisense cDNA for Branching Enzyme in the Amylose-Free Potato Mutant Leads to Physico-Chemical Changes in the Starch," Planta 198: 340-347 (1996).

Fujita et al., "Grain and Starch Characteristics of the Double Recessive Lines for Amylose-free and High Amylose Gene in Barley," Breeding Science 49: 217-219, 1999.

Gao et al., "Characterization of dull 1, a Maize Gene Coding for a Novel Starch Synthase," Plant Cell 10:399-412 (1998).

Gao et al., "*Triticum aestivum* mRNA for starch synthase ITa-2 (wSs2a-2)." EMBL Abstract Accession No. AJ269503, Jul. 6, 2000.

Gao et al., "Isolation, characterization, and expression analysis of starch synthase IIa cDNA from wheat (*Triticum aestivum* L.)," Genome, vol. 43: 768-75 (2000).

Goering and DeHass, "A Comparison of the Properties of Large- and Small-Granule Starch Isolated from Several Isogenic Lines of Barley," Cereal Chemistry 51:573-578 (1974).

Harn et al., "Isolation and Characterization of the zSSIIA and zSSIIb Starch Synthase cDNA Clones from Maize Engdosperm," Plant Mol. Biol. 37:639-649 (1998).

Holmes et al., Henderson's Dictionary of Biological Terms, 9th Ed., Van Nostrand Reinhold Co., New York, 1979, p. 218.

Klosgen, et al., "Molecular Analysis of the Waxy Locus of *Zea mays*," Mol. Gen. Genet. 203: 237-244 (1986).

Knight, et al., "Molecular Cloning of Starch Synthase I from Maize (w64) Endosperm and Expression in *Escherichia coli*," Plant J. 14(5): 613-622 (1998).

Kull et al., "Genetic Engineering of Potato Starch Composition: Inhibition of Amylose Biosynthesis in Tubers from Transgenic Potato Lines by the Expression of Antisense Sequences of the Gene for Granule-bound Starch Synthase," J. Genet. Breed. 49: 69-76 (1995).

Jansson et al., "Cloning, Characterization and Modification of Genes Encoding Starch Branching Enzymes in Barley." Starch: Structure and Functionality. Royal Society of Chemistry, London, pp. 196-203 (1997).

Jarvi and Eslick, "Shrunken Endosperm Mutants in Barley," Crop Science 15:363-366 (1975).

Li et al., "Cloning and Characterization of a Gene Encoding Wheat Starch Synthase I," Theor. Appl. Genet. 98: 1208-1216 (1999).

Li et al, "*Triticum aestivum* starch synthase IIA mRNA, complete cds." EMBL Abstract Accession No. AF155217, Sep. 7, 1999.

Li et al, "The Localization and Expression of the Class IT Starch Synthases of Wheat," Plant Physiology, vol. 120:1147-55 (1999).

Mazzolini et al., "Assaying synthetic ribozymes in plants: high-level expression of a functional hammerhead structure fails to inhibit target gene activity in transiently transformed protoplasts," Plant Mol. Biol. 20: 715-731 (1992).

Miao et al., "Evaluation and Characterization of an Endosperm-Specific sbeIIa Promoter in Wheat," Chinese Science Bulletin 49(6): 579-585 (2004).

Mizuno et al., "Alteration of the Structural Properties of Starch Components by the Lack of an Isoform of Starch Branching Enzyme in Rice Seeds," J. Biol. Chem. 268(25): 19084-19091 (1993).

Morell et al., "The Biochemistry and Molecular Biology of Starch Synthesis in Cereals," Aust. J. Plant. Physiol. 22: 647-660 (1995).

Morell et al., "Barley sex6 mutants lack starch synthase Iia activity and contain a starch with novel properties," The Plant Journal 34:173-185 (2003).

Myers et al., "Recent Progress toward Understanding Biosynthesis of the Amylopectin Crystal," Plant Physiology 122: 989-997 (2000).

Nishi et al., "Biochemical and Genetic Analysis of the Effects of Amylose-Extender Mutation in Rice Endosperm." Plant Physiology 127:459-472 (2001).

Nakamura Y., Towards a Better Understanding of the Metabolic System for Amylopectin Biosynthesis in Plants: Rice Endosperm as s Model Tissue. Plant Cell Physiology 43(7):718-725 (2002).

National Plant Germplasm System—(http://www.ars-grin.gov/npgsD, Grln System Accession No. GSHO 2476, Jun. 23, 1997.

Official Action issued Sep. 10, 2009 in connection with European Patent Application No. 01983291.4.

Okagaki R.J., "Nucleotide Sequence of a Long cDNA from the Rice Waxy Gene," Plant Molecular Biology 19: 513-516 (1992).

Puchta, "Gene Replacement by Homologous Recombination in Plants," Plant Mol. Biol. 48: 173-182 (2002).

Rahman, Sadequr et al., "Comparison of Starch-Branching Enzyme Genes Reveals Evolutionary Relationships Among Isoforms. Characterization of a Gene for Starch-Branching Enzyme IIa from the Wheat D Genome Donor Aegilops tauschii," Plant Physiology. 125: 1314-1324 (2001).

Rahman, S. et al., "A Complex Arrangement of Genes at a Starch Branching Enzyme I Locus in the D-genome Donor of Wheat," Genome 40: 465-474 (1997).

Rahman, S. et al., "The Major Proteins of Wheat Endosperm Starch Granules," Aust. J. Plant Physiol., 22:793-803 (1995).

Rahman, S. et al., "Characterisation of a Gene Encoding Wheat Endosperm Starch Branching Enzyme-I," Theor. Appl. Genet. 98: 156-163 (1999).

Safford, et al., "Consequences of Antisense RNA Inhibition of Starch Branching Enzyme Activity on Properties of Potato Starch," Carbohydrate Polymers 35: 155-168 (1998).

Sathish et al. "Cloning and Anti-Sense RNA Constructs of a Startch Branching Enzyme Gene From Barley Endosperm." Photosynthesis: from Light to Biosphere vol. V. P. Mathis (ed.) pp. 313-316 (1995).

Schondelmaier et al., "Genetical Studies in the Mode of Inheritance and Localization of the amol (High Amylose) Gene in Barley," Plant Breeding 109: 274-280 (1992).

Schwall, et al., "Production of Very-High-Amylose Potato Starch by Inhibition of SBE A and B," Nature Biotechnology 18: 551-554 (2000).

Shannon and Garwood, "In Starch: Chemistry and Technology," Whistler et al., eds, Academic Press, Orlando, FL, 25-86 (1984).

Sidebottom, et al., "Characterization of the Difference of Starch Branching Enzyme Activities in Normal and Low-Amylopectin Maize during Kernel Development," Journal of Cereal Science 27: 279-287 (1998).

Sun et al., "Identification of Four Starch-Branching Enzymes in Barley Endosperm: Partial Purification of forms I, IIa and IIb." New Phytol. 137:215-222 (1997).

Sun et al., "The Two Genes Encoding Startch-Branching Enzymes IIa and IIb Are Differentially Expressed in Barley," Plant Physiology 118:37-49 (1998).

Sundberg et al., "Glycaemic Responses and Hyopcholesterolaemic Effects of High-Amylose Barley Diets on Broiler Chicks," J. Sci. Food Agric. 76: 457-463 (1998).

Takaoka, M. et al., "Structural characterization of high molecular weight starch granule-bound proteins in wheat (*Triticum aestivum* L.)," J. Agric. Food Chem. 45: 2929-2934 (1997).

Tang et al. (2001) "Physicochemical properties and structure of large, medium and small granule starches in fractions of nomlal barley endospem1" Carbohydrate Research 330:241-248.

Terada at al., "Efficient Gene Targeting by Homologous Recombination in Rice," Nature Biotech. 20: 1030-1034 (1997).

Tester, T. F. "Influence of growth conditions on barley starch properties." Biological Macromolecules 21:37-45 (1997).

Tester, R.F. "The effects of ambient temperature during the Grain-filing period on the composition and properties of starch and four barley genotypes." Journal of Cereal Science 13:113-127 (1991).

Tetlow, I.J. et al., "Recent developments in understanding the regulation of starch metabolism in higher plants" Journal of Experimental Botany 55(406):2131-2145(2004).

Thomas, et al., "Size Constraints for Targeting Post-Transcriptional Gene Silencing and for RNA-directed Mehtylation in Nicotiana benthamiana Using a Potato Virus X Vector," Plant J. 25: 417-425 (2001).

Van der Leij et al., "Sequence of the Structural Gene for Granule-Bound Starch Synthase of Potato (*Solanum Tuberosum* L.) and Evidence for a Single Point Deletion in the amf allele," Mol. Gen. Genet. 228: 240-248 (1991).

Vrinten et al. "Wheat Granule-Bound Starch Synthase I and IT Are Encoded by Separate Genes That Are Expressed in Different Tissues," Plant Physiology, vol. 122, 255-63 (2000).

Walker and Meritt, "Genetic Control of Abnormal Starch Granules and High Amylose Content in a Mutant of Glacier Barley," Nature 221:482-484(1969).

Yamamori et al., "Genetic Elimination of a Starch Granule Protein, SGP-1, of Wheat Generates an Altered Starch with Apparent High Amylose," Theor. Appl. Genet. 101: 21-29 (2000).

Yamamori and Endo, "Variation of Starch Granule Proteins and Chromosome Mapping of Their Coding Genes in Common Wheat," Theor. Appl. Genet. 93: 275-181 (1996).

Yamamori, "Selection of a Wheat Lacking a Putative Enzyme for Starch Synthesis, SGP-1," Proc. 9th in Wheat Gen. Symp. 4:300-302 (1998).

Abel et al., GenBank Accession #Y10416 (Jan. 9, 1997) S. Tuberosum mRNA for Soluble Starch Synthase.

Bhullar et al., GenBank Accession #CAB40374 (Mar. 20, 1998) Starch synthase isoform SS III [*Vigna unguiculata*].

Block et al., GenBank Accession #U48227 (Feb. 1, 1996) *Triticum aestivum* soluble starch synthase mRNA, partial cds.

D'Hulst et al., GenBank Accession #AAC17969 (Nov. 5, 2001) Granule-bound starch synthase I precursor [*Chlamydomonas reinhardtii*].

Gao et al., GenBank Accession #AAC14014 (Apr. 18, 1998) Starch synthase DULL 1 [*Zea mays*].

Gao et al., GenBank Accession #AAC14015 (Apr. 18, 1998) Starch synthase DULL 1 [*Zea mays*].

Gao et al., GenBank Accession #CAB86618 (Apr. 18, 2002) Starch synthase Iia-1 [*Triticum aestivum*].

Gao et al., GenBank Accession #AJ269502 (Apr. 18, 2002) *Triticum aestivum* mRNA for starch synthase Iia-1 (wSs2a-1 gene).

Rahman et al., GenBank Accession #AF076680 (May 6, 1997) *Aegilops tauschii* starch branching enzyme-I (SBE-I) gene, complete cds.

Walter et al., GenBank Accession #AAB17085 (Oct. 18, 1996) Starch Synthase.

Walter et al., GenBank Accession #U66377 (Oct. 18, 1996) *Triticum aestivum* soluble starch synthase mRNA, partial cds.

File History of U.S. Patent Application Publication No. 2004/0199942 A1. Morell et al., published Oct. 7, 2004 (U.S. Appl. No. 10/416,439, filed Dec. 5, 2003).

U.S. Appl. No. 13/243,220, filed Sep. 23, 2011, Regina et al.

* cited by examiner

| Position | Locus | Description |
|---|---|---|
| 70 | Rpg1 (T) | Reaction to *Puccinia graminis* 1 |
| 67 | Run1 | Reaction to *Ustilago nuda* 1 |
| 61 | brh1 (br, ari-i) | Brachytic 1 (Breviaristatum-i) |
| 52 | fch12 (f$_c$) | Chlorina seedling 12 (Chlorina seedling c) |
| 50 | wax (wx) | Waxy endosperm |
| 48 | gsh3 (cer-a) | Glossy sheath 3 (Eceriferum-a) - - ++ |
| 43 | fch5 (f5) | Chlorina seedling 5 |
| 39 | yvs2 (y$_c$) | Virescent seedling 2 (Yellow seedling c) |
| 36 | cer-ze (gl5) | Eceriferum-ze (Glossy leaf 5) ++ ++ - |
| 32 | wnd | Winding dwarf |
|  | — rsm1 (sm) | Reaction to BSMV 1 |
| 26 | abo7 (a$_{c2}$) | Albino seedling 7 (Albino seedling c2) |
| 23 | ant1 (Rs) | Anthocyanin-less 1 (Red stem) |
| 22 | ert-m | Erectoides-m |
| 18 | ert-a | Erectoides-a |
| 13 | ert-d | Erectoides-d |
| 12 | fch8 (f8) | Chlorina seedling 8 |
| 10 | fst3 (fs3) | Fragile stem 3 |
| 9 | cer-f | Eceriferum-f + + ++ |
| 8 | dsp1 (l) | Dense spike 1 |
| 7 | msg14 | Male sterile genetic 14 |
| 6 | msg10 | Male sterile genetic 10 |
| 4 | sex6 | Shrunken endosperm xenia 6 |
| 2 | seg5 | Shrunken endosperm 5 |
| 1 | seg2 | Shrunken endosperm 2 |
| 0 | nud (n) | Naked caryopsis |
| -5 | fch4 (f4) | Chlorina seedling 4 |
| -6 | Amy2 | Alpha-amylase 2 |
| -7 | lks2 (lk2) | Short awn 2 |
| -8 | ubs4 (u4, ari-d) | Unbranched style 4 (Breviaristatum-d) |
| -11 | blx2 (bl2) | Non-blue aleurone xenia 2 |
| -20 | lbi3 (lb3) | Long basal rachis internode 3 |
|  | — xnt4 (x$_{c2}$) | Xantha seedling 4 (Xantha seedling c2) |
|  | — msg50 | Male sterile genetic 50 |
| -31 | Rym2 (Ym2) | Reaction to BaYMV 2 |
| -35 | seg4 | Shrunken endosperm 4 |
| -46 | Xnt1 (X$_a$) | Xantha seedling 1 (Xantha a) |
| -56 | Rph3 (Pa3) | Reaction to *Puccinia hordei* 3 |
|  | —xnt9 (xan,,i) | Xantha seedling 9 (Xantha seedling i) |
| -80 | seg1 | Shrunken endosperm 1 |
| -85 | msg23 | Male sterile genetic 23 |

FIGURE 7

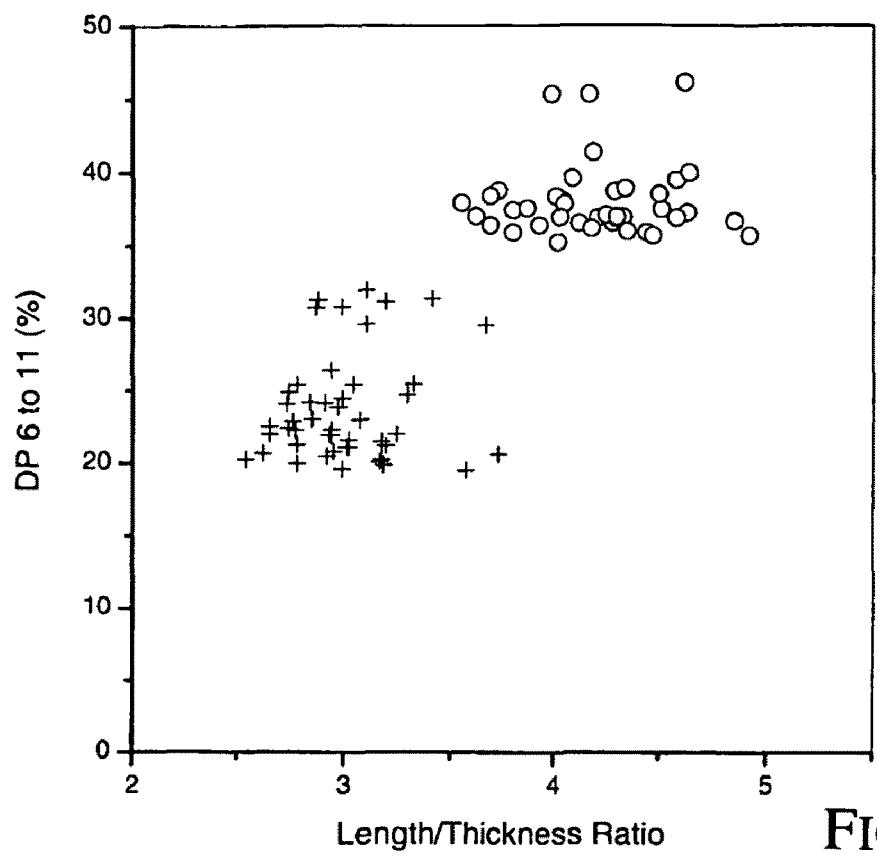
FIGURE 8
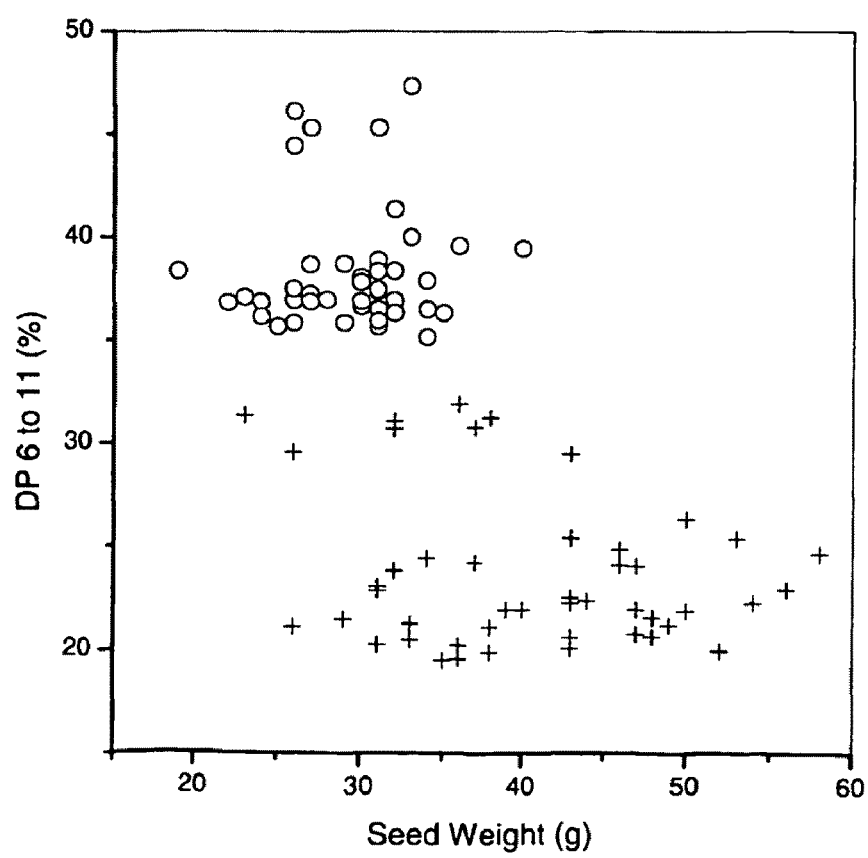

FIGURE 9
Barley SSII cDNA Sequence

```
   1  CCTCGAGGTG CGTTTACCCC ACACAGAGTA CACTCCAACT CCAGTCCAAT
  51  CCAGCCCACT GCCGCTTCTG CCCGCCCATC GTACCGTCGC CCGCCCCGAT
 101  CCCGGCCGCC GCCATGTCGT CGGCGGTCGC GTCCCCCGCG TCCTTCCTCG
 151  CGCTCGCGTC CGCCTCGCCC GGGAGATCAT CACGGAGGAG GGCGAGGGTG
 201  GGCGCGTCGC CAACCCGCGC TGGGGCCGGC AGGCTGCAAT GGCGGCCGTC
 251  GCCGCTGCAG CGCACGGCTC GCGACGGAGC GGTGGCCGCG CGCGCCGCCG
 301  GGATCGACGA CGCCGCGCCC GGTAGGCAGC CCCGCGCTCG CCGCTATGGC
 351  GCCGCCACCA AGGTCGCGGA TCCCGTCAAG ACGCTCGATC GCGACGCCGC
 401  GGAAGGTGGT GGGCCGTCCC CGCCGGCACC GAGGCAGGAC GCCGCCCGTC
 451  TGCCGAGTAA GAACGGCACG CTGATCAACG GTGAGAACAA ACCTACCGGC
 501  GGCGGTGGCG CGACTAAAGA CAGCGGGCTT GCCACACCCG CACGCGCGCC
 551  CCATCTGTCA ATCCAAAACA GAGTACCGGT GAACGGTGAA AACAAACATA
 601  AGGTCGCCTC GCCGCCGACC AGCATAGTGG ATGTCGCGTC TCCGGGTTCC
 651  GCAGCTAACA TTTCCATCAG TAACAAGGTG CCGCCGTCCG TTGTCCCAGC
 701  CAAGAAGACG CCGCCGTCGT CCGTTTTCCC GGCCAAGAAG ACGCTGCCGT
 751  CGTCCGGCTC AAATTTTGTG TCCTCGGCCT CTGCTCCAG GCTGGACACT
 801  GTCAGCGATG TGGAACTTGC ACAGAAGAAG GATGCGCTGA TTGTCAAAGA
 851  AGCTCCAAAA CCAAAGGCTC TTTCGGCCCC TGCAGCCCCC GCTGTACAAG
 901  AAGACCTTTG GGATTTCAAG AAATACATTG GTTTCGAGGA GCCCGTGGAG
 951  GCCAAGGATG ATGGCTCGGC TGTTGCAGAT GATGCGGGTT CCTTTGAACA
1001  TCACCAGAAT CATGATTCCG GACCTTTGGC AGGGGAGAAC GTCATGAACG
1051  TGGTCGTCGT TGCTGCTGAA TGTTCTCCCT GGTGCAAAAC AGGTGGTCTT
1101  GGAGATGTTG CGGGTGCTTT GCCCAAGGCT TTGGCTAAGA GAGGACATCG
1151  TGTTATGGTT GTGGTACCAA GGTATGGGGA CTATGAGGAA GCCTACGATG
1201  TCGGAGTCCG AAAATACTAC AAGGCTGCTG ACAGGATAT GGAAGTGAAT
1251  TATTTCCATG CTTATATCGA TGGAGTGGAT TTTGTGTTCA TTGACGCTCC
1301  TCTCTTCCGA CACCGTCAGC AAGACATTTA TGGGGGCAGC AGACAGGAAA
1351  TTATGAAGCG CATGATTTTG TTCTGCAAGG CCGCTGTCGA GGTTCCTTGG
1401  CACGTTCCAT GCGGCGGTGT CCCTTACGGG GATGGAAATC TGGTCTTCAT
1451  TGCAAATGAT TGGCACACGG CACTCCTGCC TGTCTATCTG AAAGCATATT
1501  ACAGGGACCA TGGTTTGATG CAATACAGTC GCTCCGTTAT GGTGATACAT
1551  AACATCGCTC ACCAGGGCCG TGGCCCTGTA GATGAATTCC CGTTCACCGA
1601  GTTGCCTGAG CACTACCTGG AACACTTCAG ACTGTACGAC CCCGTCGGCG
1651  GTGAGCACGC CAACTACTTC GCCGCCGGCC TGAAGATGGC GGACCAGGTT
1701  GTCGTCGTGA GCCCCGGGTA CCTGTGGGAG CTGAAGACGG TGGAGGGCGG
1751  CTGGGGGCTT CACGACATCA TACGGCAGAA CGACTGGAAG ACCCGCGGCA
1801  TCGTGAACGG CATCGACAAC ATGGAGTGGA ACCCTGAGGT GGACGTCCAC
1851  CTGAAGTCGG ACGGCTACAC CAACTTCTCC CTGAAGACGC TGGACTCCGG
1901  CAAGCGGCAG TGCAAGGAGG CCCTGCAGCG CGAGCTGGGG CTGCAGGTCC
1951  GCGGCGACGT GCCGCTGCTC GGGTTCATCG GCGGCTGGA CGGGCAGAAG
2001  GGCGTGGAGA TCATCGCGGA CGCGATGCCC TGGATCGTGA GCCAGGACGT
2051  GCAGCTGGTG ATGCTGGGCA CGGGGCGCCA CGACCTGGAG AGCATGCTGC
2101  AGCACTTCGA GCGGGAGCAC CACGACAAGG TGCGCGGGTG GGTGGGGTTC
2151  TCCGTGCGCC TGGCGCACCG GATCACGGCG GGCGCCGACG CGCTCCTCAT
2201  GCCCTCCCGG TTCGAGCCGT GCGGGCTGAA CCAGCTCTAC GCGATGGCCT
2251  ACGGCACCGT CCCCGTCGTG CACGCCGTCG GCGGCTTGAG GGATACCGTG
2301  CCGCCGTTCG ACCCCTTCAA CCACTCCGGG CTCGGGTGGA CGTTCGACCG
2351  CGCCGAGGCG CACAAGCTGA TCGAGGCGCT CGGGCACTGC CTCCGCACCT
2401  ACCGGGACCA CAAGGAGAGC TGGAGGGGCC TCCAGGAGCG CGGCATGTCG
2451  CAGGACTTCA GCTGGGAACA TGCCGCCAAG CTCTACGAGG ACGTCCTCGT
2501  CCAGGCCAAG TACCAGTGGT GAACGCTGCT ACCCGGTCCA GCCCCGCATG
2551  CGTGCATGAG AGGATGGAAA TGCGCATTGC GCACTTGCAG ATTTGGCGCA
2601  CGCAGGAACG TGCCGTCCTT CTTGATGAGA ACGCCGGCAT CCGCGAGGTT
2651  GAGACGCTGA TTCCGATCTG GTCCGTCGCA GAGTAGAGTG AAACGCTCCT
2701  TGTTGCAGGT ATATGGGAAT GTTTTTTTTC CTTTTTTTTT GCGAGGGAGG
2751  TATATGGGAA TGTTAACTTG GTATTGTAAT GTGGTATGCT GTGTGCATTA
2801  TTACATCGGT TGTTGTTGCT TATTCTTGCT AGCTAAGTCG GAGGCCAAGA
```

```
2851  GCGAAAGCTA GCTCACATGT CTGATGTATG CAAGTGACAT GGTTGGTTTG
2901  AAAAAAAAAA AAAAAAAAA
```

Figure 9
-continued-

Comparison of cDNA Sequences

```
             1                                                          50
MK6827       -------GTG CGTTTACCCC ACACAGAGTA CACTCCAACT CCAGTCCAGT
MOREX        -------GTG CGTTTACCCC ACACAGAGTA CACTCCAACT CCAGTCCAGT
292          -------GTG CGTTTACCCC ACACAGAGTA CACTCCAACT CCAGTCCAGT
HIMALAYA     CCTCGAGGTG CGTTTACCCC ACACAGAGTA CACTCCAACT CCAGTCCAAT 51                                                         100
MK6827       CCAGCCCACT GCCGCTTCTG CCCGCCCATC GTACCGTCGC CCGCCCCGAT
MOREX        CCAGCCCACT GCCGCTTCTG CCCGCCCATC GTACCGTCGC CCGCCCCGAT
292          CCAGCCCACT GCCGCTTCTG CCCGCCCATC GTACCGTCGC CCGCCCCGAT
HIMALAYA     CCAGCCCACT GCCGCTTCTG CCCGCCCATC GTACCGTCGC CCGCCCCGAT

101            *** start codon                             150
MK6827       CCCGGCCGCC GCCATGTCGT CGGCGGTCGC GTCCCCCGCG TCCTTCCTCG
MOREX        CCCGGCCGCC GCCATGTCGT CGGCGGTCGC GTCCCCCGCG TCCTTCCTCG
292          CCCGGCCGCC GCCATGTCGT CGGCGGTCGC GTCCCCCGCG TCCTTCCTCG
HIMALAYA     CCCGGCCGCC GCCATGTCGT CGGCGGTCGC GTCCCCCGCG TCCTTCCTCG 151                                                        200
MK6827       CGCTCGCGTC CGCCTCGCCC GGGAGATCAT CACGGAGGAG GGCGAGGGTG
MOREX        CGCTCGCGTC CGCCTCGCCC GGGAGATCAT CACGGAGGAG GGCGAGGGTG
292          CGCTCGCGTC CGCCTCGCCC GGGAGATCAT CACGGAGGAG GGCGAGGGTG
HIMALAYA     CGCTCGCGTC CGCCTCGCCC GGGAGATCAT CACGGAGGAG GGCGAGGGTG 201                                                  #
MK6827       GGCGCGTCGC CAACCCGCGC TGGGGCCGGC AGGCTGCAAT GACGGCCGTC
MOREX        GGCGCGTCGC CAACCCGCGC TGGGGCCGGC AGGCTGCAAT GGCGGCCGTC
292          GGCGCGTCGC CAACCCGCGC TGGGGCCGGC AGGCTGCAAT GGCGGCCGTC
HIMALAYA     GGCGCGTCGC CAACCCGCGC TGGGGCCGGC AGGCTGCAAT GGCGGCCGTC 251                                                        300
MK6827       GCCGCTGCAG CGCACGGCTC GCGACGGAGC GGTGGCCGCG CGCGCCGCCG
MOREX        GCCGCTGCAG CGCACGGCTC GCGACGGAGC GGTGGCCGCG CGCGCCGCCG
292          GCCGCTGCAG CGCACGGCTC GCGACGGAGC GGTGGCCGCG CGCGCCGCCG
HIMALAYA     GCCGCTGCAG CGCACGGCTC GCGACGGAGC GGTGGCCGCG CGCGCCGCCG 301                                                        350
MK6827       GGATCGACGA CGCCGCGCCC GGTAGGCAGC CCCGCGCTCG CCGCTATGGC
MOREX        GGATCGACGA CGCCGCGCCC GGTAGGCAGC CCCGCGCTCG CCGCTATGGC
292          GGATCGACGA CGCCGCGCCC GGTAGGCAGC CCCGCGCTCG CCGCTATGGC
HIMALAYA     GGATCGACGA CGCCGCGCCC GGTAGGCAGC CCCGCGCTCG CCGCTATGGC 351                                                        400
MK6827       GCCGCCACCA AGGTCGCGGA TCCCGTCAAG ACGCTCGATC GCGACGCCGC
MOREX        GCCGCCACCA AGGTCGCGGA TCCCGTCAAG ACGCTCGATC GCGACGCCGC
292          GCCGCCACCA AGGTCGCGGA TCCCGTCAAG ACGCTCGATC GCGACGCCGC
HIMALAYA     GCCGCCACCA AGGTCGCGGA TCCCGTCAAG ACGCTCGATC GCGACGCCGC 401                                                        450
MK6827       GGAAGGTGGT GGGCCGTCCC CGCCGGCACC GAGGCAGGAC GCCGCCCGTC
MOREX        GGAAGGTGGT GGGCCGTCCC CGCCGGCACC GAGGCAGGAC GCCGCCCGTC
292          GGAAGGTGGT GGGCCGTCCC CGCCGGCACC GAGGCAGGAC GCCGCCCGTC
HIMALAYA     GGAAGGTGGT GGGCCGTCCC CGCCGGCACC GAGGCAGGAC GCCGCCCGTC 451                                                        500
MK6827       TGCCGAGTAA GAACGGCACG CTGATCAACG GTGAGAACAA ACCTACCGGC
MOREX        TGCCGAGTAA GAACGGCACG CTGATCAACG GTGAGAACAA ACCTACCGGC
292          TGCCGAGTAA GAACGGCACG CTGATCAACG GTGAGAACAA ACCTACCGGC
HIMALAYA     TGCCGAGTAA GAACGGCACG CTGATCAACG GTGAGAACAA ACCTACCGGC
```

FIGURE 11

```
            501                                                       550
MK6827      GGCGGTGGCG CGACTAAAGA CAGCGGGCTG CCCACACCCG CACGCGCGCC
MOREX       GGCGGTGGCG CGACTAAAGA CAGCGGGCTG CCCACACCCG CACGCGCGCC
292         GGCGGTGGCG CGACTAAAGA CAGCGGGCTG CCCACACCCG CACGCGCGCC
HIMALAYA    GGCGGTGGCG CGACTAAAGA CAGCGGGCTT GCCACACCCG CACGCGCGCC 551                                                       600
MK6827      CCATCTGTCA ATCCAGAACA GAGTACCGGT GAACGGTGAA AACAAACATA
MOREX       CCATCTGTCA ATCCAGAACA GAGTACCGGT GAACGGTGAA AACAAACATA
292         CCATCTGTCA ATCCAGAACA GAGTACCGGT GAACGGTGAA AACAAACATA
HIMALAYA    CCATCTGTCA ATCCAAAACA GAGTACCGGT GAACGGTGAA AACAAACATA 601                                                       650
MK6827      AGGTCGCCTC GCCGCCGACC AGCATAGTGG ATGTCGCGTC TCCGGGTTCC
MOREX       AGGTCGCCTC GCCGCCGACC AGCATAGTGG ATGTCGCGTC TCCGGGTTCC
292         AGGTCGCCTC GCCGCCGACC AGCATAGTGG ATGTCGCGTC TCCGGGTTCC
HIMALAYA    AGGTCGCCTC GCCGCCGACC AGCATAGTGG ATGTCGCGTC TCCGGGTTCC 651                                                       700
MK6827      GCAGCTAACA TTTCCATCAG TAACAAGGTG CCGCCGTCCG TTGTCCCAGC
MOREX       GCAGCTAACA TTTCCATCAG TAACAAGGTG CCGCCGTCCG TTGTCCCAGC
292         GCAGCCAACA TTTCCATCAG TAACAAGGTG CCGCCGTCCG TTGTCCCAGC
HIMALAYA    GCAGCTAACA TTTCCATCAG TAACAAGGTG CCGCCGTCCG TTGTCCCAGC 701                                                       750
MK6827      CAAGAAGACG CCGCCGTCGT CCGTTTTCCC GGCCAAGAAG GCGCCGCCGT
MOREX       CAAGAAGACG CCGCCGTCGT CCGTTTTCCC GGCCAAGAAG GCGCCGCCGT
292         CAAGAAGACG CCGCCGTCGT CCGTTTTCCC GGCCAAGAAG GCGCCGCCGT
HIMALAYA    CAAGAAGACG CCGCCGTCGT CCGTTTTCCC GGCCAAGAAG .......... ..........

751                                                       800
MK6827      CGTCCGTTGT CCCGGCCAAG AAGACGCTGC CGTCGTCCGG CTCAAATTTT
MOREX       CGTCCGTTGT CCCGGCCAAG AAGACGCTGC CGTCGTCCGG CTCAAATTTT
292         CGTCCGTTGT CCCGGCCAAG AAGACGCTGC CGTCGTCCGG CTCAAATTTT
HIMALAYA    .......... .......... ...ACGCTGC CGTCGTCCGG CTCAAATTTT 801                                                       850
MK6827      GTGTCCTCGG CCTCTGCTCC CAGGCTGGAC ACTGTCAGCG ATGTGGAACT
MOREX       GTGTCCTCGG CCTCTGCTCC CAGGCTGGAC ACTGTCAGCG ATGTGGAACT
292         GTGTCCTCGG CCTCTGCTCC CAGGCTGGAC ACTGTCAGCG ATGTGGAACT
HIMALAYA    GTGTCCTCGG CCTCTGCTCC CAGGCTGGAC ACTGTCAGCG ATGTGGAACT 851                                                       900
MK6827      TGCACAGAAG AAGGATGCGC TGATTGTCAA AGAAGCTCCA AAACCAAAGG
MOREX       TGCACAGAAG AAGGATGCGC TGATTGTCAA AGAAGCTCCA AAACCAAAGG
292         TGCACAGAAG AAGGATGCGC TGATTGTCAA AGAAGCTCCA AAACCAAAGG
HIMALAYA    TGCACAGAAG AAGGATGCGC TGATTGTCAA AGAAGCTCCA AAACCAAAGG 901                                                       950
MK6827      CTCTTTCGGC CCCTGCAGCC CCCGCTGTAC AAGAAGACCT TTGGGATTTC
MOREX       CTCTTTCGGC CCCTGCAGCC CCCGCTGTAC AAGAAGACCT TTGGGATTTC
292         CTCTTTCGGC CCCTGCAGCC CCCGCTGTAC AAGAAGACCT TTGGGATTTC
HIMALAYA    CTCTTTCGGC CCCTGCAGCC CCCGCTGTAC AAGAAGACCT TTGGGATTTC 951                                                      1000
MK6827      AAGAAATACA TTGGTTTCGA GGAGCCCGTG GAGGCCAAGG ATGATGGCTC
MOREX       AAGAAATACA TTGGTTTCGA GGAGCCCGTG GAGGCCAAGG ATGATGGCTC
292         AAGAAATACA TTGGTTTCGA GGAGCCCGTG GAGGCCAAGG ATGATGGCTC
HIMALAYA    AAGAAATACA TTGGTTTCGA GGAGCCCGTG GAGGCCAAGG ATGATGGCTC
```

Figure 11
-continued-

```
              1001                                              1050
MK6827    GGCTGTTGCA GATGATGCGG GTTCCTTTGA ACATCACCAG AATCATGATT
MOREX     GGCTGTTGCA GATGATGCGG GTTCCTTTGA ACATCACCAG AATCATGATT
292       GGCTGTTGCA GATGATGCGG GTTCCTTTGA ACATCACCAG AATCATGATT
HIMALAYA  GGCTGTTGCA GATGATGCGG GTTCCTTTGA ACATCACCAG AATCATGATT 1051                                              1100
MK6827    CCGGACCTTT GGCAGGGGAG AACGTCATGA ACGTGGTCGT CGTTGCTGCT
MOREX     CCGGACCTTT GGCAGGGGAG AACGTCATGA ACGTGGTCGT CGTTGCTGCT
292       CCGGACCTTT GGCAGGGGAG AACGTCATGA ACGTGGTCGT CGTTGCTGCT
HIMALAYA  CCGGACCTTT GGCAGGGGAG AACGTCATGA ACGTGGTCGT CGTTGCTGCT 1101                                              1150
MK6827    GAATGTTCTC CCTGGTGCAA AACAGGTGGT CTTGGAGATA TTGCGGGTGC
MOREX     GAATGTTCTC CCTGGTGCAA AACAGGTGGT CTTGGAGATG TTGCGGGTGC
292       GAATGTTCTC CCTGGTGCAA AACAGGTGGT CTTGGAGATG TTGCGGGTGC
HIMALAYA  GAATGTTCTC CCTGGTGCAA AACAGGTGGT CTTGGAGATG TTGCGGGTGC 1151                                              1200
MK6827    TTTGCCCAAG GCTTTGGCTA AGAGAGGACA TCGTGTTATG GTTGTGGTAC
MOREX     TTTGCCCAAG GCTTTGGCTA AGAGAGGACA TCGTGTTATG GTTGTGGTAC
292       TTTGCCCAAG GCTTTGGCTA AGAGAGGACA TCGTGTTATG GTTGTGGTAC
HIMALAYA  TTTGCCCAAG GCTTTGGCTA AGAGAGGACA TCGTGTTATG GTTGTGGTAC 1201                                              1250
MK6827    CAAGGTATGG GGACTATGAG GAAGCCTACG ATGTCGGAGT CCGAAAATAC
MOREX     CAAGGTATGG GGACTATGAG GAAGCCTACG ATGTCGGAGT CCGAAAATAC
292       CAAGGTATGG GGACTATGAG GAAGCCTACG ATGTCGGAGT CCGAAAATAC
HIMALAYA  CAAGGTATGG GGACTATGAG GAAGCCTACG ATGTCGGAGT CCGAAAATAC 1251                                              1300
MK6827    TACAAGGCTG CTGGACAGGA TATGGAAGTG AATTATTTCC ATGCTTATAT
MOREX     TACAAGGCTG CTGGACAGGA TATGGAAGTG AATTATTTCC ATGCTTATAT
292       TACAAGGCTG CTGGACAGGA TATGGAAGTG AATTATTTCC ATGCTTATAT
HIMALAYA  TACAAGGCTG CTGGACAGGA TATGGAAGTG AATTATTTCC ATGCTTATAT 1301                                              1350
MK6827    CGATGGAGTG GATTTTGTGT TCATTGACGC TCCTCTCTTC CGACACCGTC
MOREX     CGATGGAGTG GATTTTGTGT TCATTGACGC TCCTCTCTTC CGACACCGTC
292       CGATGGAGTG GATTTTGTGT TCATTGACGC TCCTCTCTTC CGACACCGTC
HIMALAYA  CGATGGAGTG GATTTTGTGT TCATTGACGC TCCTCTCTTC CGACACCGTC 1351                                              1400
MK6827    AGCAAGACAT TTATGGGGGC AGCAGACAGG AAATTATGAA GCGCATGATT
MOREX     AGCAAGACAT TTATGGGGGC AGCAGACAGG AAATTATGAA GCGCATGATT
292       AGCAAGACAT TTATGGGGGC AGCAGACAGG AAATTATGAA GCGCATGATT
HIMALAYA  AGCAAGACAT TTATGGGGGC AGCAGACAGG AAATTATGAA GCGCATGATT 1401                                              1450
MK6827    TTGTTCTGCA AGGCCGCTGT CGAGGTTCCT TGGCACGTTC CATGCGGCGG
MOREX     TTGTTCTGCA AGGCCGCTGT CGAGGTTCCT TGGCACGTTC CATGCGGCGG
292       TTGTTCTGCA AGGCCGCTGT CGAGGTTCCT TGGCACGTTC CATGCGGCGG
HIMALAYA  TTGTTCTGCA AGGCCGCTGT CGAGGTTCCT TGGCACGTTC CATGCGGCGG 1451                                              1500
MK6827    TGTCCCTTAC GGGGATGGAA ATCTGGTCTT CATTGCAAAT GATTGGCACA
MOREX     TGTCCCTTAC GGGGATGGAA ATCTGGTCTT CATTGCAAAT GATTGGCACA
292       TGTCCCTTAC GGGGATGGAA ATCTGGTCTT CATTGCAAAT GATTGGCACA
HIMALAYA  TGTCCCTTAC GGGGATGGAA ATCTGGTCTT CATTGCAAAT GATTGGCACA
```

Figure 11
-continued-

|          | 1501       |            |            |            | 1550       |
|----------|------------|------------|------------|------------|------------|
| MK6827   | CGGCACTCCT | GCCTGTCTAT | CTGAAAGCAT | ATTACAGGGA | CCATGGTTTG |
| MOREX    | CGGCACTCCT | GCCTGTCTAT | CTGAAAGCAT | ATTACAGGGA | CCATGGTTTG |
| 292      | CGGCACTCCT | GCCTGTCTAT | CTGAAAGCAT | ATTACAGGGA | CCATGGTTTG |
| HIMALAYA | CGGCACTCCT | GCCTGTCTAT | CTGAAAGCAT | ATTACAGGGA | CCATGGTTTG |

|          | 1551       |            |            |            | 1600       |
|----------|------------|------------|------------|------------|------------|
| MK6827   | ATGCAATACA | GTCGCTCCGT | TATGGTGATA | CATAACATCG | CTCACCAGGG |
| MOREX    | ATGCAATACA | GTCGCTCCGT | TATGGTGATA | CATAACATCG | CTCACCAGGG |
| 292      | ATGCAATACA | GTCGCTCCGT | TATGGTGATA | CATAACATCG | CTCACCAGGG |
| HIMALAYA | ATGCAATACA | GTCGCTCCGT | TATGGTGATA | CATAACATCG | CTCACCAGGG |

|          | 1601       |            |            |            | 1650       |
|----------|------------|------------|------------|------------|------------|
| MK6827   | CCGTGGCCCT | GTAGATGAAT | TCCCGTTCAC | CGAGTTGCCT | GAGCACTACC |
| MOREX    | CCGTGGCCCT | GTAGATGAAT | TCCCGTTCAC | CGAGTTGCCT | GAGCACTACC |
| 292      | CCGTGGCCCT | GTAGATGAAT | TCCCGTTCAC | CGAGTTGCCT | GAGCACTACC |
| HIMALAYA | CCGTGGCCCT | GTAGATGAAT | TCCCGTTCAC | CGAGTTGCCT | GAGCACTACC |

|          | 1651       |            |            |            | 1700       |
|----------|------------|------------|------------|------------|------------|
| MK6827   | TGGAACACTT | CAGACTGTAC | GACCCCGTCG | GCGGTGAGCA | CGCCAACTAC |
| MOREX    | TGGAACACTT | CAGACTGTAC | GACCCCGTCG | GCGGTGAGCA | CGCCAACTAC |
| 292      | TGGAACACTT | CAGACTGTAC | GACCCCGTCG | GCGGTGAGCA | CGCCAACTAC |
| HIMALAYA | TGGAACACTT | CAGACTGTAC | GACCCCGTCG | GCGGTGAGCA | CGCCAACTAC |

|          | 1701       |            |            |            | 1750       |
|----------|------------|------------|------------|------------|------------|
| MK6827   | TTCGCCGCCG | GCCTGAAGAT | GGCGGACCAG | GTTGTCGTCG | TGAGCCCCGG |
| MOREX    | TTCGCCGCCG | GCCTGAAGAT | GGCGGACCAG | GTTGTCGTCG | TGAGCCCCGG |
| 292      | TTCGCCGCCG | GCCTGAAGAT | GGCGGACCAG | GTTGTCGTCG | TGAGCCCCGG |
| HIMALAYA | TTCGCCGCCG | GCCTGAAGAT | GGCGGACCAG | GTTGTCGTCG | TGAGCCCCGG |

|          | 1751       |            |            |            | 1800       |
|----------|------------|------------|------------|------------|------------|
| MK6827   | GTACCTGTGG | GAGCTGAAGA | CGGTGGAGGG | CGGCTGGGGG | CTTCACGACA |
| MOREX    | GTACCTGTGG | GAGCTGAAGA | CGGTGGAGGG | CGGCTGGGGG | CTTCACGACA |
| 292      | GTACCTGTGG | GAGCTGAAGA | CGGTGGAGGG | CGGCTGGGGG | CTTCACGACA |
| HIMALAYA | GTACCTGTGG | GAGCTGAAGA | CGGTGGAGGG | CGGCTGGGGG | CTTCACGACA |

|          | 1801       |            |            |            | 1850       |
|----------|------------|------------|------------|------------|------------|
| MK6827   | TCATACGGCA | GAACGACTGG | AAGACCCGCG | GCATCGTGAA | CGGCATCGAC |
| MOREX    | TCATACGGCA | GAACGACTGG | AAGACCCGCG | GCATCGTGAA | CGGCATCGAC |
| 292      | TCATACGGCA | GAACGACTGG | AAGACCCGCG | GCATCGTGAA | CGGCATCGAC |
| HIMALAYA | TCATACGGCA | GAACGACTGG | AAGACCCGCG | GCATCGTGAA | CGGCATCGAC |

|          | 1851       | &          |            | 1900       |            |
|----------|------------|------------|------------|------------|------------|
| MK6827   | AACATGGAGT | GGAACCCTGA | GGTGGACGTC | CACCTGAAGT | CGGACGGCTA |
| MOREX    | AACATGGAGT | GGAACCCTGA | GGTGGACGTC | CACCTGAAGT | CGGACGGCTA |
| 292      | AACATGGAGT | GAAACCCTGA | GGTGGACGTC | CACCTGAAGT | CGGACGGCTA |
| HIMALAYA | AACATGGAGT | GGAACCCTGA | GGTGGACGTC | CACCTGAAGT | CGGACGGCTA |

|          | 1901       |            |            |            | 1950       |
|----------|------------|------------|------------|------------|------------|
| MK6827   | CACCAACTTC | TCCCTGAAGA | CGCTGGACTC | CGGCAAGCGG | CAGTGCAAGG |
| MOREX    | CACCAACTTC | TCCCTGAAGA | CGCTGGACTC | CGGCAAGCGG | CAGTGCAAGG |
| 292      | CACCAACTTC | TCCCTGAAGA | CGCTGGACTC | CGGCAAGCGG | CAGTGCAAGG |
| HIMALAYA | CACCAACTTC | TCCCTGAAGA | CGCTGGACTC | CGGCAAGCGG | CAGTGCAAGG |

|          | 1951       |            |            |            | 2000       |
|----------|------------|------------|------------|------------|------------|
| MK6827   | AGGCCCTGCA | GCGCGAGCTG | GGGCTGCAGG | TCCGCGGCGA | CGTGCCGCTG |
| MOREX    | AGGCCCTGCA | GCGCGAGCTG | GGGCTGCAGG | TCCGCGGCGA | CGTGCCGCTG |
| 292      | AGGCCCTGCA | GCGCGAGCTG | GGGCTGCAGG | TCCGCGGCGA | CGTGCCGCTG |
| HIMALAYA | AGGCCCTGCA | GCGCGAGCTG | GGGCTGCAGG | TCCGCGGCGA | CGTGCCGCTG |

Figure 11
-continued-

```
                  2001                                                    2050
MK6827            CTCGGGTTCA TCGGGCGGCT GGACGGGCAG AAGGGCGTGG AGATCATCGC
MOREX             CTCGGGTTCA TCGGGCGGCT GGACGGGCAG AAGGGCGTGG AGATCATCGC
292               CTCGGGTTCA TCGGGCGGCT GGACGGGCAG AAGGGCGTGG AGATCATCGC
HIMALAYA          CTCGGGTTCA TCGGGCGGCT GGACGGGCAG AAGGGCGTGG AGATCATCGC 2051                                                    2100
MK6827            GGACGCGATG CCCTGGATCG TGAGCCAGGA CGTGCAGCTG GTGATGCTGG
MOREX             GGACGCGATG CCCTGGATCG TGAGCCAGGA CGTGCAGCTG GTGATGCTGG
292               GGACGCGATG CCCTGGATCG TGAGCCAGGA CGTGCAGCTG GTGATGCTGG
HIMALAYA          GGACGCGATG CCCTGGATCG TGAGCCAGGA CGTGCAGCTG GTGATGCTGG 2101                                                    2150
MK6827            GCACGGGGCG CCACGACCTG GAGAGCATGC TGCAGCACTT CGAGCGGGAG
MOREX             GCACGGGGCG CCACGACCTG GAGAGCATGC TGCAGCACTT CGAGCGGGAG
292               GCACGGGGCG CCACGACCTG GAGAGCATGC TGCAGCACTT CGAGCGGGAG
HIMALAYA          GCACGGGGCG CCACGACCTG GAGAGCATGC TGCAGCACTT CGAGCGGGAG 2151                                                    2200
MK6827            CACCACGACA AGGTGCGCGG GTGGGTGGGG TTCTCCGTGC GCCTGGCGCA
MOREX             CACCACGACA AGGTGCGCGG GTGGGTGGGG TTCTCCGTGC GCCTGGCGCA
292               CACCACGACA AGGTGCGCGG GTGGGTGGGG TTCTCCGTGC GCCTGGCGCA
HIMALAYA          CACCACGACA AGGTGCGCGG GTGGGTGGGG TTCTCCGTGC GCCTGGCGCA 2201                                                    2250
MK6827            CCGGATCACG GCGGGCGCCG ACGCGCTCCT CATGCCCTCC CGGTTCGAGC
MOREX             CCGGATCACG GCGGGCGCCG ACGCGCTCCT CATGCCCTCC CGGTTCGAGC
292               CCGGATCACG GCGGGCGCCG ACGCGCTCCT CATGCCCTCC CGGTTCGAGC
HIMALAYA          CCGGATCACG GCGGGCGCCG ACGCGCTCCT CATGCCCTCC CGGTTCGAGC 2251                                                    2300
MK6827            CGTGCGGGCT GAACCAGCTC TACGCGATGG CCTACGGCAC CATCCCTGTC
MOREX             CGTGCGGGCT GAACCAGCTC TACGCGATGG CCTACGGCAC CATCCCTGTC
292               CGTGCGGGCT GAACCAGCTC TACGCGATGG CCTACGGCAC CATCCCTGTC
HIMALAYA          CGTGCGGGCT GAACCAGCTC TACGCGATGG CCTACGGCAC CGTCCCCGTC 2301                                                    2350
MK6827            GTGCACGCCG TCGGCGGCCT GAGGGATACC GTGCCGCCGT TCGACCCCTT
MOREX             GTGCACGCCG TCGGCGGCCT GAGGGATACC GTGCCGCCGT TCGACCCCTT
292               GTGCACGCCG TCGGCGGCCT GAGGGATACC GTGCCGCCGT TCGACCCCTT
HIMALAYA          GTGCACGCCG TCGGCGGCTT GAGGGATACC GTGCCGCCGT TCGACCCCTT 2351                                                    2400
MK6827            CAACCACTCC GGGCTCGGGT GGACGTTCGA CCGCGCCGAG GCGCACAAGC
MOREX             CAACCACTCC GGGCTCGGGT GGACGTTCGA CCGCGCCGAG GCGCACAAGC
292               CAACCACTCC GGGCTCGGGT GGACGTTCGA CCGCGCCGAG GCGCACAAGC
HIMALAYA          CAACCACTCC GGGCTCGGGT GGACGTTCGA CCGCGCCGAG GCGCACAAGC 2401                                                    2450
MK6827            TGATCGAGGC GCTCGGGCAC TGCCTCCGCA CCTACCGGGA CCACAAGGAG
MOREX             TGATCGAGGC GCTCGGGCAC TGCCTCCGCA CCTACCGGGA CCACAAGGAG
292               TGATCGAGGC GCTCGGGCAC TGCCTCCGCA CCTACCGGGA CCACAAGGAG
HIMALAYA          TGATCGAGGC GCTCGGGCAC TGCCTCCGCA CCTACCGGGA CCACAAGGAG 2451                                                    2500
MK6827            AGCTGGAGGG GCCTCCAGGA GCGCGGCATG TCGCAGGACT TCAGCTGGGA
MOREX             AGCTGGAGGG GCCTCCAGGA GCGCGGCATG TCGCAGGACT TCAGCTGGGA
292               AGCTGGAGGG GCCTCCAGGA GCGCGGCATG TCGCAGGACT TCAGCTGGGA
HIMALAYA          AGCTGGAGGG GCCTCCAGGA GCGCGGCATG TCGCAGGACT TCAGCTGGGA
```

Figure 11
-continued-

|          | 2501       |            |            |            | 2550       |
|----------|------------|------------|------------|------------|------------|
| MK6827   | ACATGCCGCC | AAGCTCTACG | AGGACGTCCT | CGTCCAGGCC | AAGTACCAGT |
| MOREX    | ACATGCCGCC | AAGCTCTACG | AGGACGTCCT | CGTCCAGGCC | AAGTACCAGT |
| 292      | ACATGCCGCC | AAGCTCTACG | AGGACGTCCT | CGTCCAGGCC | AAGTACCAGT |
| HIMALAYA | ACATGCCGCC | AAGCTCTACG | AGGACGTCCT | CGTCCAGGCC | AAGTACCAGT |

|          | 2551 *** stop codon |            |            |            | 2600       |
|----------|------------|------------|------------|------------|------------|
| MK6827   | GGTGAACGCT | GCTACCCGGT | CCAGCCCCGC | ATGCGTGCAT | GAGAGGATGG |
| MOREX    | GGTGAACGCT | GCTACCCGGT | CCAGCCCCGC | ATGCGTGCAT | GAGAGGATGG |
| 292      | GGTGAACGCT | GCTACCCGGT | CCAGCCCCGC | ATGCGTGCAT | GAGAGGATGG |
| HIMALAYA | GGTGAACGCT | GCTACCCGGT | CCAGCCCCGC | ATGCGTGCAT | GAGAGGATGG |

|          | 2601       |            |            |            | 2650       |
|----------|------------|------------|------------|------------|------------|
| MK6827   | AAATGCGCAT | TGCGCACTTG | CAGATTTGGC | GCATGCAGGA | ACGTGCCGTC |
| MOREX    | AAATGCGCAT | TGCGCACTTG | CAGATTTGGC | GCATGCAGGA | ACGTGCCGTC |
| 292      | AAATGCGCAT | TGCGCACTTG | CAGATTTGGC | GCACGCAGGA | ACGTGCCGTC |
| HIMALAYA | AAATGCGCAT | TGCGCACTTG | CAGATTTGGC | GCACGCAGGA | ACGTGCCGTC |

|          | 2651       |            |            |            | 2700       |
|----------|------------|------------|------------|------------|------------|
| MK6827   | CTTCTTGATG | GGAACGCCGG | CATCCGCGAG | GTTGAGACGC | TGATTCCGAT |
| MOREX    | CTTCTTGATG | GGAACGCCGG | CATCCGCGAG | GTTGAGACGC | TGATTCCGAT |
| 292      | CTTCTTGATG | AGAACGCCGG | CATCCGCGAG | GTTGAGACGC | TGATTCCGAT |
| HIMALAYA | CTTCTTGATG | AGAACGCCGG | CATCCGCGAG | GTTGAGACGC | TGATTCCGAT |

|          | 2701       |            |            |            | 2750       |
|----------|------------|------------|------------|------------|------------|
| MK6827   | CTGGTCCGTC | GCAGAGTAGA | GTGAAACGCT | CCTTGTTGCA | GGTATATGGG |
| MOREX    | CTGGTCCGTC | GCAGAGTAGA | GTGAAACGCT | CCTTGTTGCA | GGTATATGGG |
| 292      | CTGGTCCGTC | GCAGAGTAGA | GTGAAACGCT | CCTTGTTGCA | GGTATATGGG |
| HIMALAYA | CTGGTCCGTC | GCAGAGTAGA | GTGAAACGCT | CCTTGTTGCA | GGTATATGGG |

|          | 2751       |            |            |            | 2800       |
|----------|------------|------------|------------|------------|------------|
| MK6827   | AATGTTTTTT | TTTTCC.TTT | TTTTTTTTGC | GAGGGAGGTA | TATGGGAATG |
| MOREX    | AATGTTTTTT | TTTTCCTTTT | TTTTTTTTGC | GAGGGAGGTA | TATGGGAATG |
| 292      | AATGTTTTTT | TT..CC...T | TTTTTTTTGC | GAGGGAGGTA | TATGGGAATG |
| HIMALAYA | AATGTTTTTT | TT..CC...T | TTTTTTTTGC | GAGGGAGGTA | TATGGGAATG |

|          | 2801       |            |            |            | 2850       |
|----------|------------|------------|------------|------------|------------|
| MK6827   | TTAACTTGGT | ATTGTAATGT | GGTATGCTGT | GTGCATTATT | ACATCGGTTG |
| MOREX    | TTAACTTGGT | ATTGTAATGT | GGTATGCTGT | GTGCATTATT | ACATCGGTTG |
| 292      | TTAACTTGGT | ATTGTAATGT | GGTATGCTGT | GTGCATTATT | ACATCGGTTG |
| HIMALAYA | TTAACTTGGT | ATTGTAATGT | GGTATGCTGT | GTGCATTATT | ACATCGGTTG |

|          | 2851       |            |            |            | 2900       |
|----------|------------|------------|------------|------------|------------|
| MK6827   | TTGTTGCTTA | TTCTTGCTAG | CTAAGTCGGA | GGCCAAGAGC | GAAAGCTAGC |
| MOREX    | TTGTTGCTTA | TTCTTGCTAG | CTAAGTCGGA | GGCCAAGAGC | GAAAGCTAGC |
| 292      | TTGTTGCTTA | TTCTTGCTAG | CTAAGTCGGA | GGCCAAGAGC | GAAAGCTAGC |
| HIMALAYA | TTGTTGCTTA | TTCTTGCTAG | CTAAGTCGGA | GGCCAAGAGC | GAAAGCTAGC |

|          | 2901       |            |            |            | 2950       |
|----------|------------|------------|------------|------------|------------|
| MK6827   | TCACATGTCT | GATGTATGCA | AGTGACATGG | TTGGTTTGGT | TGTGCAGTGC |
| MOREX    | TCACATGTCT | GATGTATGCA | AGTGACATGG | TTGGTTTGGT | TGTGCAGTGC |
| 292      | TCACATGTCT | GATGTATGCA | AGTGACATGG | TTGGTTTGGT | TGTGCAGTGC |
| HIMALAYA | TCACATGTCT | GATGTATGCA | AGTGACATGG | TTGGTTTGAA | AAAAAAAAA  |

|          | 2951       |
|----------|------------|
| MK6827   | AAACGGCA   |
| MOREX    | AAACGGCA   |
| 292      | AAACGGCA   |
| HIMALAYA | AAAAAAAA   |

Figure 11
-continued-

Comparison of SSII Amino Acid Sequences

```
                1                              MK6827 mutation #
Morex       MSSAVASPAS FLALASASPG RSSRRRARVG ASPTRAGAGR LQWRPSPLQR
Himalaya    MSSAVASPAS FLALASASPG RSSRRRARVG ASPTRAGAGR LQWRPSPLQR
292         MSSAVASPAS FLALASASPG RSSRRRARVG ASPTRAGAGR LQWRPSPLQR
MK6827      MSSAVASPAS FLALASASPG RSSRRRARVG ASPTRAGAGR LQ*RPSPLQR 51                                                100
Morex       TARDGAVAAR AAGIDDAAPG RQPRARRYGA ATKVADPVKT LDRDAAEGGG
Himalaya    TARDGAVAAR AAGIDDAAPG RQPRARRYGA ATKVADPVKT LDRDAAEGGG
292         TARDGAVAAR AAGIDDAAPG RQPRARRYGA ATKVADPVKT LDRDAAEGGG
MK6827      TARDGAVAAR AAGIDDAAPG RQPRARRYGA ATKVADPVKT LDRDAAEGGG 101                                               150
Morex       PSPPAPRQDA ARLPSKNGTL INGENKPTGG GGATKDSGLP TPARAPHLSI
Himalaya    PSPPAPRQDA ARLPSKNGTL INGENKPTGG GGATKDSGLP TPARAPHLSI
292         PSPPAPRQDA ARLPSKNGTL INGENKPTGG GGATKDSGLP TPARAPHLSI
MK6827      PSPPAPRQDA ARLPSKNGTL INGENKPTGG GGATKDSGLP TPARAPHLSI 151                                               200
Morex       QNRVPVNGEN KHKVASPPTS IVDVASPGSA ANISISNKVP PSVVPAKKTP
Himalaya    QNRVPVNGEN KHKVASPPTS IVDVASPGSA ANISISNKVP PSVVPAKKTP
292         QNRVPVNGEN KHKVASPPTS IVDVASPGSA ANISISNKVP PSVVPAKKTP
MK6827      QNRVPVNGEN KHKVASPPTS IVDVASPGSA ANISISNKVP PSVVPAKKTP 201                                               250
Morex       PSSVFPAKKT LPSSGSNFVS SASAPRLDTV SDVELAQKKD ALIVKEAPKP
Himalaya    PSSVFPAKKT LPSSGSNFVS SASAPRLDTV SDVELAQKKD ALIVKEAPKP
292         PSSVFPAKKT LPSSGSNFVS SASAPRLDTV SDVELAQKKD ALIVKEAPKP
MK6827      PSSVFPAKKT LPSSGSNFVS SASAPRLDTV SDVELAQKKD ALIVKEAPKP 251                                               300
Morex       KALSAPAAPA VQEDLWDFKK YIGFEEPVEA KDDGSAVADD AGSFEHHQNH
Himalaya    KALSAPAAPA VQEDLWDFKK YIGFEEPVEA KDDGSAVADD AGSFEHHQNH
292         KALSAPAAPA VQEDLWDFKK YIGFEEPVEA KDDGSAVADD AGSFEHHQNH
MK6827      KALSAPAAPA VQEDLWDFKK YIGFEEPVEA KDDGSAVADD AGSFEHHQNH 301                                               350
Morex       DSGPLAGENV MNVVVVAAEC SPWCKTGGLG DVAGALPKAL AKRGHRVMVV
Himalaya    DSGPLAGENV MNVVVVAAEC SPWCKTGGLG DVAGALPKAL AKRGHRVMVV
292         DSGPLAGENV MNVVVVAAEC SPWCKTGGLG DVAGALPKAL AKRGHRVMVV
MK6827      DSGPLAGENV MNVVVVAAEC SPWCKTGGLG DIAGALPKAL AKRGHRVMVV 351                                               400
Morex       VPRYGDYEEA YDVGVRKYYK AAGQDMEVNY FHAYIDGVDF VFIDAPLFRH
Himalaya    VPRYGDYEEA YDVGVRKYYK AAGQDMEVNY FHAYIDGVDF VFIDAPLFRH
292         VPRYGDYEEA YDVGVRKYYK AAGQDMEVNY FHAYIDGVDF VFIDAPLFRH
MK6827      VPRYGDYEEA YDVGVRKYYK AAGQDMEVNY FHAYIDGVDF VFIDAPLFRH 401                                               450
Morex       RQQDIYGGSR QEIMKRMILF CKAAVEVPWH VPCGGVPYGD GNLVFIANDW
Himalaya    RQQDIYGGSR QEIMKRMILF CKAAVEVPWH VPCGGVPYGD GNLVFIANDW
292         RQQDIYGGSR QEIMKRMILF CKAAVEVPWH VPCGGVPYGD GNLVFIANDW
MK6827      RQQDIYGGSR QEIMKRMILF CKAAVEVPWH VPCGGVPYGD GNLVFIANDW 451                                               500
Morex       HTALLPVYLK AYYRDHGLMQ YSRSVMVIHN IAHQGRGPVD EFPFTELPEH
Himalaya    HTALLPVYLK AYYRDHGLMQ YSRSVMVIHN IAHQGRGPVD EFPFTELPEH
292         HTALLPVYLK AYYRDHGLMQ YSRSVMVIHN IAHQGRGPVD EFPFTELPEH
MK6827      HTALLPVYLK AYYRDHGLMQ YSRSVMVIHN IAHQGRGPVD EFPFTELPEH 501                                               550
Morex       YLEHFRLYDP VGGEHANYFA AGLKMADQVV VVSPGYLWEL KTVEGGWGLH
Himalaya    YLEHFRLYDP VGGEHANYFA AGLKMADQVV VVSPGYLWEL KTVEGGWGLH
292         YLEHFRLYDP VGGEHANYFA AGLKMADQVV VVSPGYLWEL KTVEGGWGLH
MK6827      YLEHFRLYDP VGGEHANYFA AGLKMADQVV VVSPGYLWEL KTVEGGWGLH
```

FIGURE 12

|          | 551                                                            | $ 292 mutation                    | 600       |
|----------|----|
| Morex    | DIIRQNDWKT RGIVNGIDNM EWNPEVDVHL KSDGYTNFSL KTLDSGKRQC |
| Himalaya | DIIRQNDWKT RGIVNGIDNM EWNPEVDVHL KSDGYTNFSL KTLDSGKRQC |
| 292      | DIIRQNDWKT RGIVNGIDNM E*NPEVDVHL KSDGYTNFSL KTLDSGKRQC |
| MK6827   | DIIRQNDWKT RGIVNGIDNM EWNPEVDVHL KSDGYTNFSL KTLDSGKRQC |

|          | 601                                                    | 650 |
|----------|----|
| Morex    | KEALQRELGL QVRGDVPLLG FIGRLDGQKG VEIIADAMPW IVSQDVQLVM |
| Himalaya | KEALQRELGL QVRGDVPLLG FIGRLDGQKG VEIIADAMPW IVSQDVQLVM |
| 292      | KEALQRELGL QVRGDVPLLG FIGRLDGQKG VEIIADAMPW IVSQDVQLVM |
| MK6827   | KEALQRELGL QVRGDVPLLG FIGRLDGQKG VEIIADAMPW IVSQDVQLVM |

|          | 651                                                    | 700 |
|----------|----|
| Morex    | LGTGRHDLES MLQHFEREHH DKVRGWVGFS VRLAHRITAG ADALLMPSRF |
| Himalaya | LGTGRHDLES MLQHFEREHH DKVRGWVGFS VRLAHRITAG ADALLMPSRF |
| 292      | LGTGRHDLES MLQHFEREHH DKVRGWVGFS VRLAHRITAG ADALLMPSRF |
| MK6827   | LGTGRHDLES MLQHFEREHH DKVRGWVGFS VRLAHRITAG ADALLMPSRF |

|          | 701                                                    | 750 |
|----------|----|
| Morex    | EPCGLNQLYA MAYGTIPVVH AVGGLRDTVP PFDPFNHSGL GWTFDRAEAH |
| Himalaya | EPCGLNQLYA MAYGTIPVVH AVGGLRDTVP PFDPFNHSGL GWTFDRAEAH |
| 292      | EPCGLNQLYA MAYGTIPVVH AVGGLRDTVP PFDPFNHSGL GWTFDRAEAH |
| MK6827   | EPCGLNQLYA MAYGTIPVVH AVGGLRDTVP PFDPFNHSGL GWTFDRAEAH |

|          | 751                                                    | 800 |
|----------|----|
| Morex    | KLIEALGHCL RTYRDHKESW RGLQERGMSQ DFSWEHAAKL YEDVLVQAKY |
| Himalaya | KLIEALGHCL RTYRDHKESW RGLQERGMSQ DFSWEHAAKL YEDVLVQAKY |
| 292      | KLIEALGHCL RTYRDHKESW RGLQERGMSQ DFSWEHAAKL YEDVLVQAKY |
| MK6827   | KLIEALGHCL RTYRDHKESW RGLQERGMSQ DFSWEHAAKL YEDVLVQAKY |

|          | 801 |
|----------|-----|
| Morex    | QW* |
| Himalaya | QW* |
| 292      | QW* |
| MK6827   | QW* |

Figure 12
-continued- (a)
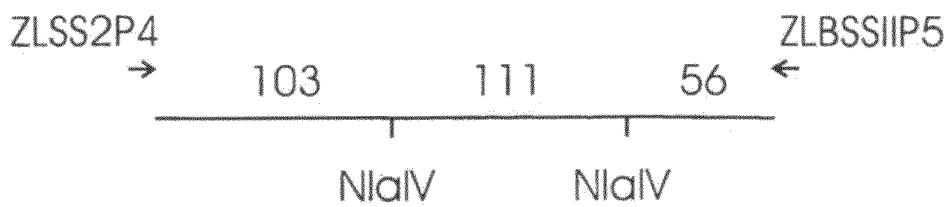
(b)
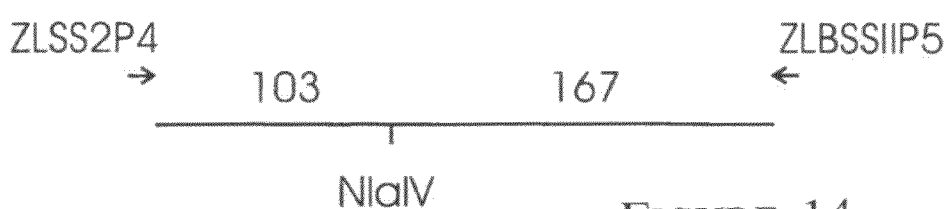
FIGURE 14
(c)
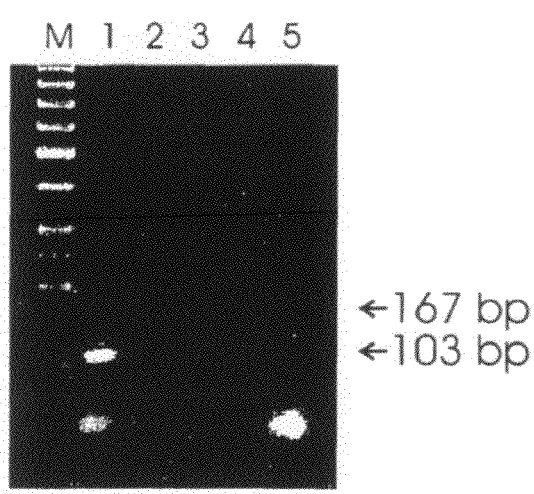
(d)
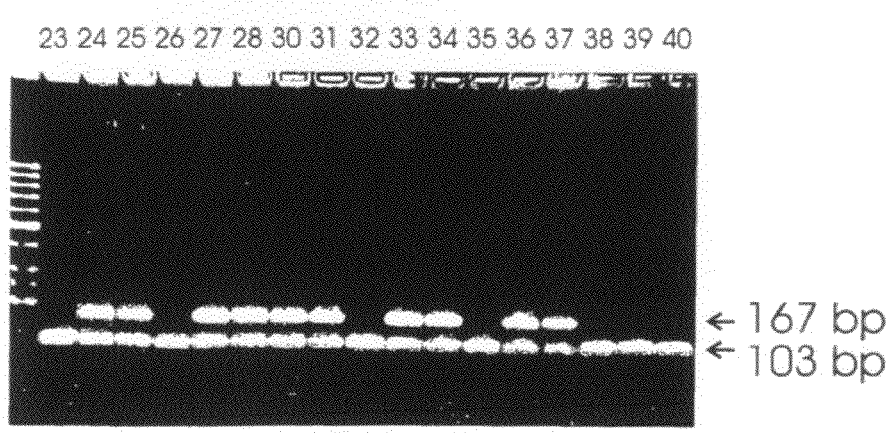

US 8,178,759 B2

BARELY WITH REDUCED SSII ACTIVITY AND STARCH AND STARCH CONTAINING PRODUCTS WITH A REDUCED AMYLOPECTIN CONTENT

This application is a continuation of U.S. Ser. No. 10/416,439, filed Dec. 5, 2003 now U.S. Pat. No. 7,888,499, a §371 national stage of PCT International Application No. PCT/AU01/01452, filed Nov. 9, 2001, and claims priority of Australian Provisional Application Nos. PR 1370, PR 1371, PR 1372, and PR 1373, all filed Nov. 9, 2000, the content of all of which are hereby incorporated by reference into the subject application.

FIELD OF THE INVENTION

This invention relates to a barley plant with a reduced SSII enzyme activity leading to a starch having reduced amylopectin content. The invention also relates to starch and grain and food products obtained therefrom.

BACKGROUND OF THE INVENTION

One finding in nutritional science is that resistant starch has important implications for bowel health, in particular health of the large bowel. The beneficial effects of resistant starch result from the provision of a nutrient to the large bowel wherein the intestinal microflora are given an energy source which is fermented to form inter alia short chain fatty acids. These short chain fatty acids provide nutrients for the colonocytes, enhance the uptake of certain nutrients across the large bowel and promote physiological activity of the colon. Generally if resistant starches or other dietary fibre is not provided the colon is metabolically relatively inactive.

There has in recent years been a direction to look at providing for resistant starches from various sources to address bowel health. Accordingly high amylose starches have been developed in certain grains such as maize for use in foods as a means of promoting bowel health.

The physical structure of starch can have an important impact on the nutritional and handling properties of starch for food products. Certain characteristics can be taken as an indication of starch structure including the distribution of amylopectin chain length, the degree of crystallinity and the presence of forms of crystallinity such as the V-complex form of starch crystallinity. Forms of these characteristics can also be taken as indicator of nutritional or handling properties of foods containing these starches. Thus short amylopectin chain length may be an indicator of low crystallinity and low gelatinisation and is also thought to have a correlation with reduced retrogradation of amylopectin. Additionally shorter amylopectin chain length distribution is thought to reflect organoleptic properties of food in which the starch is included in significant amounts. Reduced crystallinity of a starch may also be indicative of a reduced gelatinisation temperature of starch and additionally it is thought to be associated with enhanced organoleptic properties. The presence of V-complex crystallinity or other starch associated lipid will enhance the level of resistant starch and thus dietary fibre.

Lines of barley having high amylose starch contents have been identified in the past. These have only resulted in relatively modest increases in amylose content to a maximum of about 45% of total starch such as in the barley variety known as High Amylose Glacier (AC38). Whilst elevated amylose starches of that type are useful a starch with a higher amylose content still is preferred, and certain other species of grain are bred to have higher amylose content starches with levels in the 90 percentile range. These are very resistant to digestion and bring a greater health benefit.

There is a problem with providing the high amylose starches because known high amylose starches also have a high gelatinisation temperature. Gelatinisation temperature is reflective of the comminution energy required to process such foods. Thus higher temperatures are normally required to process grain or flour to manufacture foods from such grains or starches. Thus generally products having high amylose starches are more expensive. Similarly from the point of view of the consumer longer times and higher temperatures may be required to prepare the manufactured foods, or to make foods from flour having high amylose starches. Thus there is a significant disadvantage in the provision of high amylose starches in foods.

Another nutritional component of the grains and in particular of barley as β-glucans. β-glucans consist of glucose units bonded by β(1-4) and/or β(1-3) glycosidic linkages and are also not degraded by human digestive enzymes which makes them suitable as a source of dietary fibre. β-glucans can be partially digested by endogenous colonic bacteria which fermentation process gives rise to short chain fatty acids (predominantly acetate, propionate and butyrate) which are beneficial to mucosal cells lining the intestine and colon (Sakata and Engelhard Comp. Biochem Physiol. 74a:459-462 (1983))

Ingestion of β-glucan also has the effect of increasing bile acid excretion leading to a reduction in total serum cholesterol and low density lipoproteins (LDL) with a lowering of the risk of coronary disease. Similarly β-glucans act by attenuating excursions in postprandial blood glucose concentration. It is thought that both of these effects are based on the increase of viscosity in the contents of the stomach and intestines.

The composition of foods containing starches and the intimate relationship of those starches with other nutritional or other components can have a significant impact on the nutritional value of those foods or on the functional characteristics of those components in the preparation or structure of the foods.

Whilst modified starches or β glucans, for example, can be utilised in foods that provide functionality not normally afforded by unmodified sources, such processing has a tendency to either alter other components of value or carry the perception of being undesirable due to processes involved in modification. Therefore it is preferable to provide sources of constituents that can be used in unmodified form in foods.

The barley variety MK6827 is available from the Barley Germplasma Collection (USDA-ARS National Small Grain Germplasma Research Facility Aberdeen, Id. 831290 USA). The grain of MK6827 is shrunken and has a highly coloured husk and an elongate shape and, in the hands of the inventors, this grain is very difficult to process including being very resistant to milling. The properties of MK6827 grain had not been characterised before, nor had the nature of the mutation been ascertained nor is it considered suitable for producing food.

SUMMARY OF THE INVENTION

This invention arises from the isolation and characterisation of SSII mutant of barley plants the grain of which is found to contain starch that has reduced amylopectin content and therefore high relative levels of amylose and therefore has elevated levels of dietary fibre.

The grain of the mutant and grain from crosses into certain genetic backgrounds additionally has an elevated level of β glucan. The combination of elevated β glucan level and resistant starch contributing to high dietary fibre is thought by the inventors to be unique to the present invention.

Additionally, at least in some genetic backgrounds, it is found that grain from such mutants contain starch that have high relative levels of amylose, and also have low gelatinisation temperatures. The low swelling charactistics of such starch during and following gelatinisation also has advantages in certain dietary and food processing applications.

Furthermore, grain from such mutants are found to contain starch that have high relative levels of amylose, the amylose levels found are higher than 50% of the starch content which is a level never before found in unmodified starch derived from barley.

The starch of the mutants and backcrossed lines derived from the mutants (to the extent that the backcrosses have been tested) exhibit a resistant starch, with an altered structure indicated by specific physical characteristics including one or more of the group comprising the presence of a high relative amylose content, physical inaccessibility by reason of having a high β-glucan content, altered granule morphology, and the presence of starch associated lipid, and the altered structure being indicated by a characteristic selected from one or more of the group comprising low crystallinity, reduced amylopectin chain length distribution and presence of appreciable starch associated lipid.

Additionally thus far the grain derived from the mutant barley plants can readily be used in food processing procedures.

This invention in one aspect might be said to reside in starch obtained from the of grain of a barley plant the barley plant having a reduced level of SSII activity, said starch granules having a high amylose content by reason of a reduced amylopectin content.

The invention might in another aspect of broadly be said to reside a grain useful for food production obtained from a barley plant the barley plant having a reduced level of SSII activity, starch of said grain having a high amylose content by reason of a reduced amylopectin content.

In a yet further aspect the invention might broadly said to reside in a barley plant with a reduced level of SSII activity, said barley plant capable of bearing grain, starch of said grain having a high amylose content by reason of a reduced amylopectin content, said grain suitable for food production.

Alternatively the invention could be said to reside in an isolated nucleic acid molecule encoding a barley SSII protein said nucleic acid capable of hybridising under stringent conditions with SEQ ID NO 1. or a cell carrying a replicable recombinant vector carrying said nucleic acid molecule. In a yet further form the invention might be isolated nucleic acid molecule capable of hybridising specifically to SEQ ID NO 1.

BRIEF DESCRIPTION OF THE DRAWINGS

For a better understanding, the invention will now be described with reference to a number of examples.

FIG. 7. Loci on barley chromosome 7H showing the proximity of the nud1 and sex6 loci. Diagram after GrainGenes (http://wheat.pw.usda.gov/) Barley morphological genes, 7H map, author; Franckowiak J D.

FIG. 8. Relationships between seed dimensions and starch chain length distribution for 292× Tantangara doubled haploid lines. Lines denoted by (+) yielded the Himalaya PCR pattern and lines denoted by (○) gave the 292 PCR result. Panel (A), the seed length to thickness ratio plotted against the percentage of starch chains with DP between 6 and 11; Panel (B) seed weight plotted against the percentage of starch chains with DP between 6 and 11

FIG. 9 Sequence of a barley SSII cDNA (SEQ ID NO 1) from the cultivar Himalaya

FIG. 11 Comparisons of the predicted SSII cDNAs from MK6827 (SEQ ID NO 2), Morex (SEQ ID NO 3) and 292 (SEQ ID NO 4), and a cDNA sequence of Himalaya (SEQ ID NO 1). Predicted sequences were generated by identifying regions of the genomic sequences present in the Himalaya SSII cDNA. The ATG start codon and wild type stop codon are indicated, as are additional stop codons present in MK6827 (#) and 292 (&) respectively.

FIG. 12 Comparison of amino acid sequences deduced from the genes encoding SSII from barley lines 292 (SEQ ID NO 7 and SEQ ID NO 8), Morex (SEQ ID NO 5), MK6827 (SEQ ID NO 9 and SEQ ID NO 10), Himalaya (SEQ ID NO 6). Additional stop codons in 292 and MK6827 are indicated by the symbols (&) and (#) respectively.

FIG. 14. Development and use of a PCR assay for the 292 mutation. (a) schematic representation of an SSII region from Himalaya amplified by the primers ZLSS2P4 and ZLBSSIIP5 (b) representation of the region amplified from the SSII gene from 292 using ZLSS2P4 and ZLBSSIIP5, showing the absence of one NIaIV site (c) agarose gel electrophoresis of NIaIV digested products from barley; Lane M; DNA marker ladder, lane 1: MK6827, lane 2; Himalaya; lane 3, Tantangara; lane 4, 292; lane 5, 342.

DETAILED DESCRIPTION OF THE INVENTION

Definitions

Figure 1:
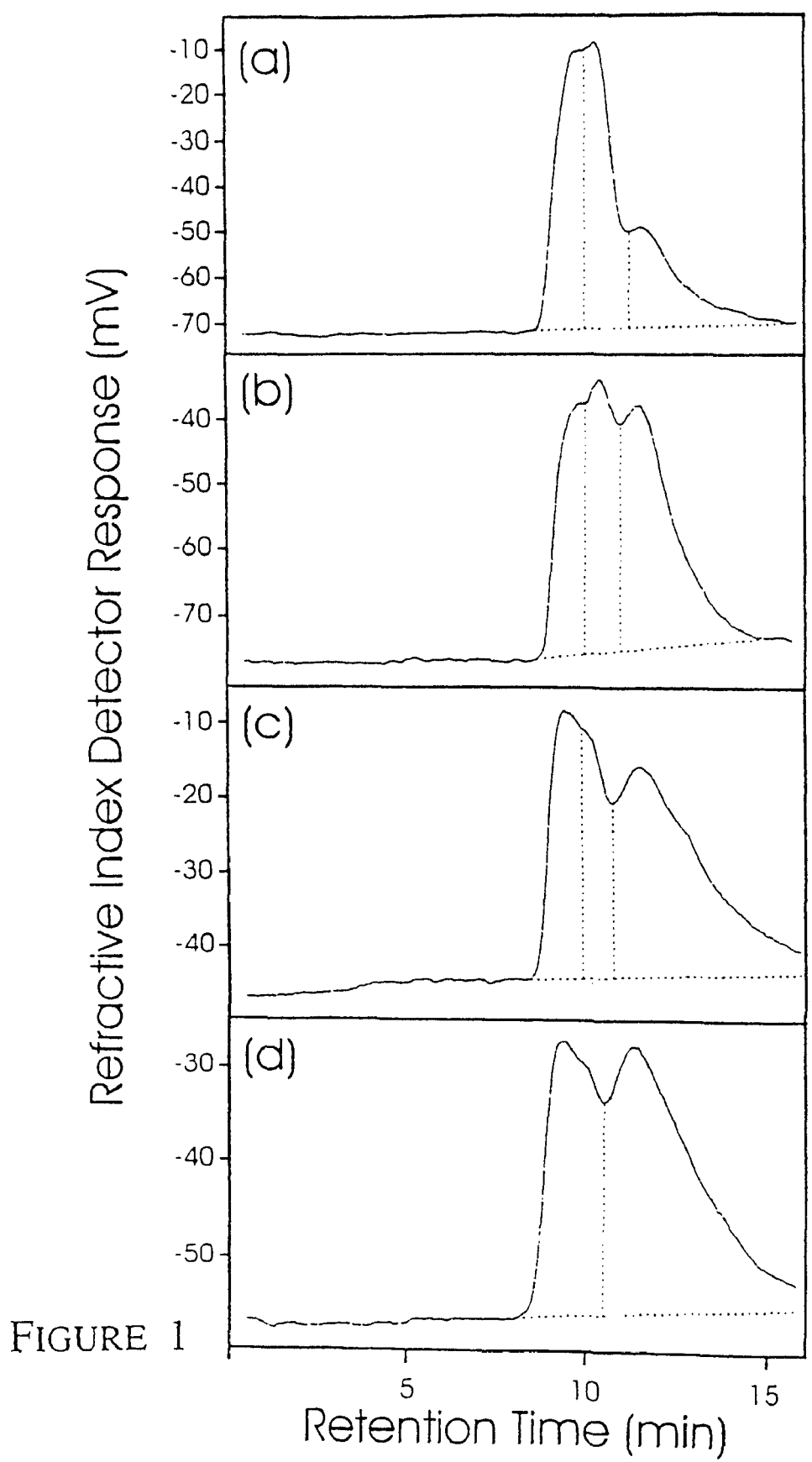
FIG. 1 Analysis of the starch molecular size distribution as determined by HPLC separation of starch in 90% DMSO. (a) Himalaya (b) AC38 (c) 342 (d) 292

Glycaemic Index. Is a comparison of the effect of a test food such as white bread or glucose on excursions in blood glucose concentration. The Glycaemic Index is a measure of the likely effect of the food concerned on post prandial serum glucose concentration and demand for insulin for blood glucose homeostasis.

Resistant Starch. The sum of starch and products of starch digestion not absorbed in the small intestine of healthy humans but entering into the large bowel. Thus resistant starch excludes products digested and absorbed in the small intestine.

Resistant starches can be classified in four groups.

RS1 physically inaccessible starch. Examples of this form of starch arise where the starch is entrapped within a protein or similar matrix or within plant cell wall, or might arise because of the partial milling of grain or in legumes after cooling.

RS2 Resistant granules. These are generally raw starches such as those that arise from raw potato or green banana, some legumes and high amylose starches.

RS3 Retrograded starches. These arise by heat/moisture treatment of starch or starch foods such as occurs in cooked and cooled potato, bread and cornflakes.

RS4 Chemically modified. These arise by reason of chemical modifications such as substitution or cross linking. This form of starch is often used in processed foods.

Dietary fibre. In this specification is the sum of carbohydrates or carbohydrate digestion products that is not absorbed in the small intestine of healthy humans but enters the large bowel. This includes resistant starch, β-glucan and other soluble and insoluble carbohydrate polymers. It is intended to comprise that portion of carbohydrates that are fermentable, at least partially, in the large bowel by the resident microflora.

Gelatinsation is the collapse (disruption) of molecular order within the starch granule with concomitant and irreversible changes in properties such as granular swelling, crystallite melting, loss of birefringence, viscosity development and starch solubilisation.

This invention arises from the isolation and characterisation of SSII mutant barley plants, the grain of which is found to contain starch that has reduced amylopectin content and therefore high relative levels of amylose and therefore has elevated levels of dietary fibre.

Such mutants are found to have a number of quite desirable characteristics, and it has been shown that crosses into various other genetic backgrounds maintains at least some of those characteristics.

The grain of the mutant and grain from crosses into certain genetic backgrounds additionally has an elevated level of β glucan. The combination of elevated β glucan level and high dietary fibre is thought by the inventors to be unique to the present invention.

Additionally at least in some genetic backgrounds it is found that grain from such mutants are found to contain starch that have high relative levels of amylose, and also have low gelatinisation temperatures. The swelling charactistics of the gelatinisation of such starch also has the benefit of being low swelling which has advantages in certain dietary and food processing applications.

Furthermore grain from such mutants are found to contain starch that have high relative levels of amylose, the amylose levels found are higher than 50% of the starch content which is a level never before found in unmodified starch derived from barley.

The starch of the mutants and to the extent that the backcrosses have been tested exhibit a resistant starch, with an altered structure indicated by specific physical characteristics including one or more of the group comprising the presence of a high relative amylose content, physical inaccessibility by reason of having a high β-glucan content, altered granule morphology, and the presence of starch associated lipid, and the altered structure being indicated by a characteristic selected from one or more of the group comprising low crystallinity, reduced amylopectin chain length distribution and presence of appreciable starch associated lipid.

Additionally thus far the grain derived from the mutant barley plants can readily be used in food processing procedures.

Grain from such mutants in one form preferably contain starch that have high relative levels of dietary fibre, more particularly amylose as well as an elevated level of β glucan. The combination of elevated β glucan level and high amylose level is thought by the inventors to be unique to the present invention, and provide for a unique source of a combination of β-glucan and resistant starch that does not, at least in broader forms of the invention require mixing of β glucan and soluble dietary fibre together or modification of the component parts.

To the best of the knowledge of the inventors the barley plant of the present invention is the first time that there has been a barley grain having elevated relative dietary fibre levels in the form of resistant starch having an elevated amylose level, that also has elevated levels of β glucan that are at the higher end of the typical levels of β glucan or that go beyond that level. Grains that have β glucan content that are still higher are of the waxy phenotype and therefore have low levels of amylose.

It is known that there is a wide variation in β glucan levels in barley in the range of about 4% to about 18% by weight of the barley, but more typically from 4% to about 8% (Izydorcyk et al., (2000) *Journal of Agricultural and Food Chemistry* 48, 982-989; Zheng et al., (2000) *Cereal Chemistry* 77, 140-144; Elfverson et al., (1999) *Cereal Chemistry* 76, 434-438; Andersson et al., (1999) *Journal of the Science of Foods and Agriculture* 79, 979-986; Oscarsson et al., (1996) *J Cereal Science* 24, 161-170; Fastnaught et al., (1996) *Crop Science* 36, 941-946). Enhanced barley strains have been developed, Prowashonupana for example, which have between about 15% and about 18% by weight β-glucan but has a waxy phenotype. This is sold commercially under the name Sustagrain™, (ConAgra™ Specially Grain Products Company, Omaha, Nebr. USA).

The levels of β glucan contemplated by this invention may depend on the genetic background in which the amylopectin synthesis enzyme activity is reduced. However it is proposed that the reduction of the amylopectin synthesis activity will have the effect of elevating the relative level of dietary fibre which, in part, takes the form of amylose, and at the same time elevating the level of β glucan. One explanation for the concomitant elevation of β glucan with elevated relative amylose levels is that such elevation might be the result of a concentration effect of having reduced endosperm and may be further increased through the diversion of carbon from starch synthesis to β glucan synthesis.

Thus the grain of the barley plant preferably has a β glucan content that is greater than 6% of total non-hulled grain weight or more preferably greater than 7% and most preferably greater than 8%, however levels of β glucan in a waxy mutant has been measured as being as high as 15 to 18% and the present invention may contemplate levels as high, or higher, than that.

In a second preferable form the grain of the barley plant has a reduced gelatinsation temperature (as measured by differential scanning calorimetry) in addition to the relatively high amylose content. On the data shown for the exemplified barley this reduced gelatinisation temperature is not just reduced when compared to starch produced by barley with somewhat elevated amylose content but also when compared with starch produced from barley with starch having normal levels of amylose. Thus whilst the invention contemplates reduced gelatinisation temperatures relative to a corresponding high amylose starch, it may also contemplate a gelatinisation temperature reduced relative to that of starch with normal amylose levels.

Additionally in the genetic backgrounds thus far checked the starch is also characterised by a swelling in heated excess water that is lower than swelling of other starches tested.

In a third preferable form the starch has amylose levels of higher than 50% of the starch content which is a level never before found in unmodified starch derived from barley.

The starch of the present barley plant has a high relative amylose content and much higher than might be anticipated for a mutation in the SSII gene or other starch synthase gene. Thus in wheat mutants in SSII result in relative amylose levels of about 35% of starch. The amylose content of starch might be considered to be elevated when the content is significantly greater than the 25% or so that is present in normal barley grain and thus might be greater than about 30% w/w of total starch. Known barley plants considered to be high amylose have a content of 35-45%. The present invention however provides for barley with an amylose content that is greater than 50%, with is a level never before found in unmodified starch derived from barley.

The relative amylose content might be greater than 60% and more preferably, still greater than 70%. It may be desired to have even higher levels and thus it has been possible to achieve even higher levels in other plants by breeding with single mutations, such levels approach 90%. Thus the invention might encompass amylose levels of greater than 80% or greater than 90%.

In a fourth preferable form the starch also has an altered structure which gives rise to the resistant starch. This might arise from a high amylose content. Resistant starch might also arise because β-glucan is present at elevated levels and is likely to exert protective effects by reason of the association of the β glucan with the starch granule, the intimacy of association potentially provides a protective effect to the starch to thereby provide for a resistance that might be characterised as an RS1 form, being somewhat inaccessible to digestion. Similarly the presence of starch-lipid association as measured by V-complex crystallinity is also likely to contribute to the level of resistant starch. In this case the resistance is likely to arise because of the physically inaccessible of the starch by virtue of the presence of the lipid and accordingly this might be regarded as an RS1 starch. It is known that retrograded starch that takes up the V-complex configuration is highly resistant to digestion and accordingly it is anticipated that amylopectin that forms part of the V-complex crystalline structure will also be resistant to digestion. The starch of the exemplified barley plant may be resistant to digestion by reason of the structure of the starch granule and accordingly may have RS2 starch. Each of these characteristics might be present separately or as two or more of these characteristics in combination.

The elevated dietary fibre may at least in part take the form of resistant starch which may be characterised by a high amylose content of the starch granules as referred to above.

The relative amylose content might be greater than 60% and more preferably greater than 70%. It may be desired to have even higher levels and thus it has been possible to achieve even higher levels in other plants by breeding with single mutation such levels approach 90%. Thus the invention might encompass amylose levels of greater than 80% or greater than 90%.

It might be desired that the barley plant additionally expresses an altered level of activity of one or more amylose synthesis enzymes or other enzymes to further enhance the relative level of amylose. Thus the barley plant may carry another mutation that further decreases or alters amylopectin biosynthesis, or a mutation or genetic background that increases amylose biosynthesis. For example the barley plant may exhibit an amylose extender genotype, such as a barley plant carrying the amo1 mutation. An example of such a plant is the variety known as AC38 (also known as High Amylose Glacier).

It will be understood that the relative level of amylose referred to is in relation to total starch content, and thus the remainder of the starch might be predominantly of an intermediate type of starch or it might be predominantly amylopectin or a mixture of both. In the barley analysed the elevated level of amylose results from decreased amylopectin levels, and accordingly the relative level of amylose does not result from an increased synthesis of amylose.

It is known that β glucan has the effect of slowing digestion in the small intestine simply by its presence when together with another food component. Similarly it is known that resistant molecules that have close juxtaposition with starch granules help to mask the starch and contribute to its resistance by making it physically inaccessible. Elevated levels of amylose and other forms of starch as may arise from association with lipid will be further enhanced therefore by the presence and physical juxtaposition to the starch granules. Thus there is provided a significant enhancement of the effects of the resistant starch, as well as a provision of other beneficial effects arising from high β glucan levels.

Additionally it is known that there is a dose response in terms of the beneficial effects of resistant starch and β glucan. It is proposed therefore that the increased level of β glucan together with the increased levels of resistant starch will provide enhanced health benefits.

The combination of the levels of β glucan and resistant starch of at least preferred forms of this invention have not been found before and certainly not from one source without a degree of modification or purification and thus forms of the present invention provide for a single practical source of these benefits.

Another preferred aspect of the starch is that despite the high relative amylose content it also has a low gelatinisation temperature as measured by differential scanning calorimetry. This is in contrast with the general finding that high amylose starches tend to have a raised gelatinisation temperature which introduces restrictions on the manner in which high amylose starches can be utilised. On the data shown for the exemplified barley this reduced gelatinisation temperature is not just reduced when compared to starch produced by lines with somewhat elevated amylose content but also when compared with starch produced from barley with starch having normal levels of amylose. Thus whilst a preferred aspect of the invention contemplates reduced gelatinisation temperatures relative to corresponding high amylose starch it may also contemplate a gelatinisation temperature reduced relative to that of starch with normal amylose levels. For high amylose starches aspects of processing requiring higher temperatures and therefore inherently require a higher energy input which is expensive and can destroy the functionality of other food components. Similarly from the point of view of the ultimate consumer, high amylose starch foods may be less convenient because of a higher temperature or longer time required for preparation. Thus, for example, in this preferred form of the invention it is now possible to provide for a product such as a noodle product requiring the addition of boiling or heated water to a vessel such as a cup and not requiring heating for an extended period of time and at the same time providing for delivery of resistant starches and other constituents of nutritional value to the large bowel.

A major effect of the low gelatinisation temperatures of these starches is the lower temperature requirements and hence comminution energy requirement of the food. A corollary is also that where, as typically might be the case in certain food processing, mixing occurs at room temperature and then the mixture is heated, the lower gelatinisation temperature also reduces the time required to achieve gelatinisation. Additionally at a range of temperatures below the temperature for full gelatinisation of normal starch, there will be more complete gelatinisation of the starch of the present invention than normal starch.

One measure of the gelatinisation capacity is reflected in the thermal properties as measured by DSC (differential scanning calorimetry). The onset of the first peak (gelatinisation peak) of DSC may be at less than 53° C., more preferably at less than 50° C. and most preferably at less than about 47° C. The onset of the first peak may be regarded as the onset of gelatinisation. The starch produced from the barley grain may have a first peak at less than about 60° C., more preferably at less than 55° C. and most preferably at less than 52° C. The ΔH (enthalpy) of the first peak may be less than about 3.5, more preferably less than about 1.0 and most preferably less than about 0.5.

Another finding of the gelatinsation of flours containing the starches of this invention is that they exhibit a reduced swelling. Swelling volume is typically measured by mixing either a starch or flour with excess water and heating to elevated temperatures, typically greater than 90° C. The sample is then collected by centrifugation and the swelling volume is expressed as the mass of the sedimented material divided by the dry weight of the sample. The swelling volumes of flour from starches of waxy and normal barleys are found to be greater than about 5.5. The swelling volumes of flour made from the grain that is a high amylose grain, (AC38) is about 3.75. Whereas the grains of the mutants and crosses examined are less than 3.2, preferably less than 3.0, but generally higher than about 2.

This low swelling gelatinisation characteristic is particularly useful where it is desired to increase the starch content of a food preparation, in particular a hydrated food preparation. In the present instance it might be desired to increase the dietary fibre content of a sol or other liquid preparation where there would otherwise be a restriction on delivery of the food preparation.

This characteristic in combination with the reduced gelatinisation temperature exhibited by the present starch provides a prospect of significantly enhancing the nutritional benefits of foods where there is a requirement of rapid preparation, such as instant soups and instant noodles.

It is postulated gelatinisation temperature effects are the result of an altered amylopectin structure in the endosperm of its grain, and one measurement of this structure is the distribution of chain lengths (degrees of polymerisation) of the starch molecules following debranching by isoamylase. An analysis of the chain length of the amylopectin content of the starch of the exemplified SSII mutants showed that when debranched they have a distribution of chain length in the range from 5 to 60 that is shorter than the distribution of starch yielded by non-mutant lines upon debranching. Starch with shorter chain lengths will also have a commensurate increase in frequency of branching. Thus the starch may also have a distribution of shorter amylopectin chain lengths. The proportion of starch chains that have a degree of polymerisation that falls in the range of 6 to 11 residues may be greater than 25%, more preferably greater than 30% and most preferably greater than 35%. The proportion of starch chains that have a degree of polymerisation that falls in the range of 12-30 residues may be less than 65%, more preferably less than 60% and most preferably less than about 55%. The proportion of starch chains that have a degree of polymerisation that falls in the range of 31-60 residues may be less than about 10%, more preferably less than about 8% but also preferably greater than about 5% and more preferably greater than about 6%. Rather than taken individually combination of proportions of the three chain length ranges might be taken as an indicator that a starch is of a type that accords with the present invention.

The reduction in chain length distribution is likely to contribute to lower gelatinsation temperatures. Reduced chain length is also thought to enhance the organoleptic properties of the starch, in particular mouthfeel, thus perhaps contributing to a smooth product. Additionally it has been postulated that reduced amylopectin chain length might decrease the extent of amylopectin degradation, which has an impact on food quality, for example it is thought to be important in bread staling.

The starch structure in the exemplified starch is additionally shown to differ in that the degree of crystallinity is reduced compared to normal starch isolated from barley. When combined with a reduced amylopectin chain length distribution, reduced granular crystallinity may indicate that gelatinsation temperature will be lower. The reduced crystallinity of a starch is also thought to be associated with enhance organoleptic properties and as with shorter amylopectin chain length contributes to a smoother mouth feel. Thus the starch may additionally exhibit reduced crystallinity resulting from reduced levels of activity of one or more amylopectin synthesis enzymes. The proportion of starch exhibiting crystallinity may be less than about 20% and preferably less than about 15%.

A further measure of the properties of the present starch is by measuring viscosity. It is found using a Rapid Visco Analyser that the peak viscosity of the starch of this invention is significantly different to that of normal and waxy starches and high amylose starches obtained from barley. These measurements were made on wholemeal however the properties of the starch will predominate in these measurements. The normal and waxy starches have a peak viscosity of between about 900 and about 500 RVA units, known high amylose starch has a peak viscosity of greater than 200, whereas barley plants according to the present invention have a peak viscosity of less than 100 with a majority being less than about 50 in some plants as low as about 10 RVA units. It will be understood by a person skilled in the art that the parameters cited empirical units and the results cited are intended to indicate the relative performance of these starches in RVA instruments or similar instruments such as the amylograph.

In addition to reduced crystallinity referred to above the present starch may be characterised by the presence of the V-complex form of starch. It is thought by the inventors that this is the first time that this form of starch has been exhibited in appreciable amounts in starch granules of a grain. This form of starch is usually associated with retrograded starch, in particular where there has been contact with lipids. In the case of the present invention it is postulated that the structure of the starch permits the formation of an intimate relationship between plant lipids and starch which results in the V-complex structure. It is thought that this form of starch may have health benefits because it has reduced digestibility and therefore may contribute to resistant starch.

Other forms of structure can also result from lipid-starch interaction and include non crystalline lipid-starch complexes. Thus the invention might also be said to reside in a barley plant exhibiting appreciable amounts of starch-lipid complexes in the starch content of the endosperm of its grain resulting from reduced levels of activity of one or more amylopectin synthesis enzymes. Starches that contain starch lipid complexes, including those that exhibit V-complex structure, are also usually resistant to digestion and thus contribute to the dietary fibre levels. Preferably the proportion of crystalline starch exhibiting a form of crystallinity characteristic of a starch-lipid complex is greater than about 50% and more preferably greater than about 80%.

The starch additional to the presence of the V-complex form of starch may also exhibit no appreciable amounts of A complex forms of starch. Absence of A-complex might be taken as indicator of the presence of a starch of this invention.

It is also found that the pasting temperature of starches and product made from the grain of this invention are considerably elevated. The pasting temperatures in known starches is less than 70° C., and this is for both normal and high amylose starches. The starches of the present invention however preferably exhibit pasting temperatures of higher than about 75° C. or more preferably higher than about 80° C. It will be noted that these are empirical measures and might be taken as relative to those measurement of the other starches.

The starch of the exemplified barley plant is found to have significant amounts of dietary fibre and resistant starch, presumably this increase is at least in part as a result of the high relative level of amylose, however there may also be a contribution of dietary fibre by reason of starch/lipid complexes, including V-complex, or because of the intimate associate of amylose or amylopectin with β glucan. Similarly simply the elevated level of β glucan may also make a significant contribution to the elevation of dietary fibre.

The elevated relative amylose levels in the endosperm of the exemplified barley plant in all likelihood results from altered amylopectin production as a result of a reduction in the level of activity of the SSII enzyme.

Mutations in the gene encoding this enzyme might be expected to exhibit increased amylose content and/or a decrease in the level of amylopectin. Where amylopectin synthesis alone is decreased, starch exhibits an increased relative level of amylose.

Reduced activity of the amylopectin synthesis enzyme may be achieved by the appropriate mutations within a respective gene or regulatory sequences of the gene. The extent to which the gene is inhibited will to some degree determine the characteristics of the starch made. The exemplified mutations of this invention being SSII mutations in barley are truncation mutants and these are known to have a significant impact on the nature of the starch, however an altered amylopectin structure will also result from a leaky mutant that sufficiently reduces amylopectin synthesis enzyme activity to provide the characteristic of interest in the starch or grain of barley. Other chromosomal rearrangements may also be effective and these might include deletions, inversions, duplication or point mutations.

Such mutations can be introduced into desirable genetic backgrounds by either mutagenizing the varieties of interest, but more reliably by crossing the mutant with a plant of the desired genetic background and performing a suitable number of backcrosses to cross out the originally undesired parent background. Isolation of mutations might be achieved by screening mutagenised plants.

A molecular biological approach might be taken as an alternative to conventional methods. The SSII sequence is presented in this specification. Vectors carrying the desired mutations and a selectable marker may be introduced into tissue cultured plants, or suitable plant systems such as protoplasts. Plants where the mutation has been integrated into a chromosome to replace an existing wild type allele can be screened by, for example, using a suitable nucleic acid probe specific for the mutation and phenotypic observation. Methods for transformation of monocotyledonous plants such as barley and for regeneration of plants from protoplasts or immature plant embryos are well known in the art, see for example, Canadian Patent Application 2092588 by Nehra, Australian Patent Application No 61781/94 by National Research Council of Canada, Australian Patent No 667939 by Japan Tobacco Inc., International Patent Application PCT/US97/10621 by Monsanto Company, U.S. Pat. No. 5,589,617, and other methods are set out in Patent specification WO99/14314.

Other known approaches to altering the activity of the amylopectin synthesis enzyme, other than the use of mutations may also be adopted. Thus, for example, this could be by expression of suitable antisense molecules that interfere with the transcription or processing of the gene or genes encoding the amylopectin synthesis enzyme. These might be based on the DNA sequence elucidated herein for the barley SSII gene. These antisense sequences can be for the structural genes or for sequences that effect control over the gene expression or splicing event. These sequences have been referred to above. Methods of devising antisense sequences are well known in the art and examples of these are can be found in, for example, U.S. Pat. No. 5,190,131, European patent specification 0467349 A1, European patent specification 0223399 A1 and European patent specification 0240208, which are incorporated herein by reference to the extent that they provide methods for carrying out antisense techniques. Methods of introducing and maintaining such sequences in plants are also published and known.

A variation of the antisense technique is to utilise ribozymes. Ribozymes are RNA molecules with enzymic function that can cleave other RNA molecules at specific sites defined by an antisense sequence. The cleavage of the RNA block the expression of the target gene. Reference is made to European patent specification 0321201 and specification WO 97/45545.

Another molecular biological approach that might also be used is that of co-suppression. The mechanism of co-suppression is not well understood, but it involves putting an extra copy of a gene into a plant in the normal orientation. In some instances the additional copy of the gene interferes with the expression of the target plant gene. Reference is made to Patent specification WO 97/20936 and European patent specification 0465572 for methods of implementing co-suppression approaches.

A further method that might be employed using the DNA sequences is duplex or double stranded RNA mediated gene suppression. In this method a DNA is used that directs the synthesis of a double stranded RNA product. The presence of the double stranded molecule triggers a response from the plant defence system that destroys both the double stranded RNA and also the RNA coming from the target plant gene, efficiently reducing or eliminating the activity of the target gene. Reference is made to Australian Patent specification 99/292514-A and Patent specification WO 99/53050 for methods of implementing this technique.

It will be understood that the invention may arise as a result of reducing the levels of activity of two or more of the above genes using a molecular biological approach.

One important product that might be envisaged in particular as a result of the high amylose and high β glucan content is a low calorific product with a reduced glycaemic index. A low calorific product might be based on inclusion of flour produced from milled grain. It might be desired, however, to first pearl the grain removing perhaps 10% or 20% by weight of the grain, thereby removing the aleurone layer and at the greater reduction removing also the germ. The effect of the pearling step is to reduce the lipid content and therefore reducing the calorific value of the food. Such foods will have the effect of being filling, enhancing bowel health, reducing the post prandial serum glucose and lipid concentration as well as providing for a low calorific food product. Use of the pearled product would result in a reduction in nutritional benefits provided by the aleurone layer and the germ. The flour produced from the pearled product is likely to have an enhanced appearance because a product made in that way tends to be whiter.

Aspects of this invention also arise from the combination of aleurone layer and germ in combination with high levels of dietary fibre. Specifically this arises from the somewhat higher relative levels of aleurone or germ present in the exemplified grain. Firstly, barley has a significantly higher aleurone layer than other commercial grains, being a result of having a three cell aleurone layer. Secondly, the exemplified barley grain is also shrunken which means that the endosperm is present in reduced amounts, a corollary of which is that the aleurone layer and the germ are present in elevated relative amounts. Thus the barley has a relatively high level of certain beneficial elements or vitamins in combination in a resistant starch delivery system, such elements include divalent cations such as bioavailable Ca++ and vitamins such as folate or antioxidants such as tocopherols and tocotrienols. Thus calcium is established in the provision of material for growth and deposition of bone and other calcified tissue and in lowering the risk of osteoporosis later in life. Folic acid is found to be protective against neural tube defects when consumed peri-conceptually and decreases the risk of cardiovascular disease thereby enhancing the effects of the combination of resistant starch and β-glucan. Folic acid also is thought to have an effect of lowering the risk of certain cancers. Tocopherol and tocotrienols carry the benefits of antioxidants and are believed to lower the risk of cancer and heart disease, and also have the effect of reducing the undesirable effects of oxidation of components of a food such as fatty acids which can result in rancidity. When these components of this preferred form of barley grain or products made therefrom constitute a convenient packaging with the one grain. One specific form of milled product might be one where the aleurone layer is included in the milled product. Particular milling process might be undertaken to enhance the amount of aleurone layer in the milled product. Such a method is referred to in Fenech et al., ((1999) J Nutr 129:1114-1119). Thus any product derived from grain milled or otherwise processed to include aleurone layer and germ will have the additional nutritional benefits, without the requirement of adding these elements from separate sources.

It will be understood that the barley plant of the present invention is preferably one having grain that is useful for food production and in particular for commercial food production. Such a production might include making of flour or other product that might be an ingredient in commercial food production. A lower level of usefulness might be a starch content greater than about 12% or perhaps greater than about 15%. Or similarly this might include the capacity to mill the grain; thus whilst pearled barley may be produced from most forms of grain certain configurations of grain are particularly resistant to milling. Another characteristic that might have an impact on a variety producing a commercially useable grain is discolouration of the product produced. Thus where the husk or other portion of the grain exhibits significant colouration, for example purple, this will come through with the product and limits its commercial applications to niche applications such as being a component of a bread containing coloured whole or kibbled grains. It is generally also more convenient that the barley plants are naked, because the presence of husks on barley grains introduces greater difficulty in processing the grain. Another aspect that might make a barley plant of higher value is on the basis of starch extraction from the grain, the higher extraction rates being more useful. Grain shape is also another feature the can impact on the commercial usefulness of a plant, thus grain shape can have an impact on the ease or otherwise with which the grain can be milled, thus for example the barley grain of MK6827 plant has an unusually very elongated grain morphology which makes it difficult to mill and process. A convenient measure of this elongate shape and useability is the ratio of two morphological characteristics length of the grain to the thickness of the grain (L/T ratio). This ratio is often dictated by the nature of the starch. It has been found by the inventors that MK6827 has a L/T ratio of greater than 6. Barley plants thus screened carrying the mutant SSII gene have an L/T ratio ranging from about 4 to about 5, although it is anticipated that this might extend over an even greater range and still be useful, perhaps being less than about 5.8 or at least 5.5.

The desired genetic background will include considerations of commercial yield and other characteristics: Such characteristics might include whether it is desired to have a winter or spring type of barley, agronomic performance, disease resistance and abiotic stress resistance. In Australia one might want to cross into barley cultivars such as Sloop, Schooner, Chebec, Franklin, Arapiles, Tantangara, Galleon, Gairdner or Picola. The examples provided are specific for an Australian production region, and other varieties will be suited for other growing regions.

A fuller grain may be desirable in terms of achieving greater yields and certain benefits of the invention might be achieved, such as the production of starch with high levels of amylose, or in the alternative starch with altered chain length distributions. Other aspects of the invention may, however, be better achieved by a grain that is less filled. Thus the proportion of aleurone layer or germ to starch may be higher in less filled grain, thereby providing for a barley flour or other product that is higher in the beneficial constituents of the aleurone layer. The high aleurone layer product might thus be higher in certain vitamins such as folate, or it might be higher in certain minerals such as calcium, and that combined with higher resistant starch levels and/or higher β glucan levels might provide synergistic effects such as providing for enhance uptake of minerals in the large bowel.

In order to maximise the amount of amylose it may be desirable for the barley plant to also have other phenotypic characteristics in addition to a reduced activity of one or more amylopectin synthesising enzymes. The genetic background might therefore include additionally an high amylose phenotype for example the amo1 mutation in AC38 (causal gene unknown) and the waxy mutation (found for example in the Waxiro variety). Additionally it might be desired to make double mutations in other barley mutants available with shrunken endosperms where the causal gene is not known.

In a further aspect the invention could be said to reside in the grain produced from a barley plant as referred to in this specification.

It will also be understood that the invention encompasses a processed grain including a milled, ground, kibbled, pearled or rolled grain or product obtained from the processed or whole grain of the barley plant referred to above, including flour. These products may be then used in various food products, for example farinaceous product such as breads, cakes biscuits and the like, or food additives, such as thickeners or to make malted or other barley drinks, noodles and quick soups.

Alternatively the invention encompasses starch isolated from the grain of the barley plant referred to above. Starch might be isolated by known techniques.

It will be understood that one benefit of the present invention is that it provides for one or more products that are of particular nutritional benefit, and moreover it does so without the need to modify the starch or other constituents of the barley grain.

However it may be desired to make modifications to the starch, β glucan or other constituent of the grain, and the invention encompasses such a modified constituent.

The method of modification are those known, and include the extraction of the starch or β glucan or other constituent by conventional methods and modification of the starches to for the desired resistant form.

Thus the starch or β glucan may be modified either singly of multiply though the use of a treatment selected from group including but not limited to, heat and/or moisture, physically (for example ball milling), enzymatically (using for example α or β amylase, pullalanase or the like), chemical hydrolysis (wet or dry using liquid or gaseous reagents), oxidation, cross bonding with difunctional reagents (for example sodium trimetaphosphate, phosphorous oxychloride), or carboxymethylation.

The dietary fibre content of the exemplified barley grain does not result solely from the increased relative endbspermal amylose content. One primary reason is that β-glucan is present at elevated levels and contributes significantly to the dietary fibre level. There are also likely to be protective effects by reason of the association of the β glucan with the starch granule, the intimacy of association potentially provides a protective effect to the starch to thereby provide for a resistance that might be characterised as an RS1 form, being somewhat inaccessible to digestion. Similarly the presence of starch-lipid association as measured by V-complex crystallinity is also likely to contribute to the level of resistant carbohydrate. In this case the resistance is likely to arise by reason of physical inaccessibility by reason of the presence of the lipid and accordingly this might be regarded as an RS1 starch. Thus it is known that retrograded starch that takes up the V-complex configuration is highly resistant to digestion and accordingly it is anticipated that amylopectin that forms part of the starch granule having the V-complex crystalline structure will have enhanced resistance to digestion. Thirdly the starch of the exemplified barley plant may be resistant to digestion by reason of the structure of the starch granule and accordingly may have RS2 starch.

It will be understood that whilst various indications have been given as to aspects of the present invention, the invention may reside in combinations of two or more aspects of the present invention.

Example 1

Background

The synthesis of starch in the endosperm of higher plants is carried out by a suite of enzymes that catalyse four key steps. Firstly, ADPglucose pyrophosphorylase activates the monomer precursor of starch through the synthesis of ADPglucose from G-1-P and ATP. Secondly, the activated glucosyl donor, ADPglucose, is transferred to the non-reducing end of a pre-existing α1-4 linkage by starch synthases. Thirdly, starch branching enzymes introduce branch points through the cleavage of a region of α1,4 linked glucan followed by transfer of the cleaved chain to an acceptor chain, forming a new α1,6 linkage. Finally, genetic studies demonstrate that starch debranching enzymes are essential for the synthesis of normal quantities of starch in higher plants, however, the mechanism through which debranching enzymes act is unresolved (Myers et al., 2000).

While it is clear that at least these four activities are required for normal starch granule synthesis in higher plants, multiple isoforms of each of the four activities are found in the endosperm of higher plants and specific roles have been proposed for individual isoforms on the basis of mutational analysis (Wang et al, 1998, Buleon et al., 1998) or through the modification of gene expression levels using transgenic approaches (Abel et al., 1996, Jobling et al., 1999, Sewall et al., 2000). However, the precise contributions of each isoform of each activity to starch biosynthesis are still not known, and it is not known whether these contributions differ markedly between species. In the cereal endosperm, two isoforms of ADPglucose pyrophosphorylase are present, one form within the amyloplast, and one form in the cytoplasm (Denyer et al., 1996, Thorbjornsen et al., 1996). Each form is composed of two subunit types. The shrunken (sh2) and brittle (bt2) mutants in maize represent lesions in large and small subunits respectively (Girouz and Hannah, 1994). Four classes of starch synthase are found in the cereal endosperm, an isoform exclusively localised within the starch granule, granule-bound starch synthase (GBSS), two forms that are partitioned between the granule and the soluble fraction (SSI, Li et al., 1999a, SSII, Li et al., 1999b) and a fourth form that is entirely located in the soluble fraction, SSIII (Cao et al, 2000, Li et al., 1999b, Li et al, 2000). GBSS has been shown to be essential for amylose synthesis (Shure et al., 1983), and mutations in SSII and SSIII have been shown to alter amylopectin structure (Gao et al, 1998, Craig et al., 1998). No mutations defining a role for SSI activity have been described.

Three forms of branching enzyme are expressed in the cereal endosperm, branching enzyme I (BEI), branching enzyme IIa (BEIIa) and branching enzyme IIb (BEIIb) (Hedman and Boyer, 1982, Boyer and Preiss, 1978, Mizuno et al., 1992, Sun et al., 1997). In maize and rice, high amylose phenotypes have been shown to result from lesions in the BEIIb gene (Boyer and Preiss, 1981, Mizuno et al., 1993). In these mutants, amylose content is significantly elevated, and the branch frequency of the residual amylopectin is reduced. In addition, there is a significant pool of material that is defined as "intermediate" between amylose and amylopectin (Boyer et al., 1980, Takeda, et al., 1993). Mutations defining the roles of BEIIa and BEI have yet to be described, although in potato down regulation of BEI alone causes minimal affects on starch structure (Filpse et al., 1996). However, in potato the combination of down regulation of BEII and BEI provides a much higher amylose content than the down-regulation of BEII atone (Schwall et al., 2000). Two types of debranching enzymes are present in higher plants and are defined on the basis of their substrate specificities, isoamylase type debranching enzymes, and pullulanase type debranching enzymes (Myers et al., 2000). Sugary-1 mutations in maize and rice are associated with deficiency of both debranching enzymes (James et al., 1995, Kubo et al., 1999) however the causal mutation maps to the same location as the isoamylase-type debranching enzyme gene. In the *Chlamydomonas* sta-7 mutant (Mouille et al., 1996), the analog of the maize sugary-1 mutation, isoamylase activity alone is down regulated.

Known variation in barley starch structure is limited relative to the variation available in maize. The most highly characterised mutations, are waxy and a high amylose mutation identified as AC38. Double mutants have also been constructed and analysed (Schondelmaier et al., 1992, Fujita et al, 1999). A broad range of characteristics of the variation in starch structure and properties (Czuchajowska et al., 1992; Schondelmaier et al., 1992; Vasanthan and Bhatty, 1995; Morrison et al., 1984; Gerring and DeHaas, 1974; Bankes et al., 1971; Persson and Christerson, 1997: Vasanthan and Bhatty, 1998; Czuchajowska et al., 1998; Song and Jane, 2000; Andreev et al., 1999; Yoshimoto et al., 2000), and grain properties (Swantson 1992, Ahokas 1979; Oscarsson et al, 1997; Oscarsson et al., 1998; Andersson et al., 1999; Elfverson et al., 1999; Bhatty 1999; Zheng et al., 2000; Izydorczyk et al., 2000; Andersson et al., 2000), have been reported and the utility of the mutants in animal feeding trials (Xue et al., 1996; Newman et al., 1978; Calvert et al., 1976; Wilson et al., 1975; Sundberg et al., 1998; Bergh et al., 1999), human foods (Swanston et al., 1995; Fastnaught et al., 1996; Persson et al., 1996; Pomeranz et al., 1972) and human nutrition investigated (Pomeranz 1992; Granfeldt et al., 1994; Oscarsson et al., 1996; Akerberg et al., 1998.)

In the present example, we have isolated a novel class of high amylose mutant from barley. The mutant lines contain amylose contents (65-70%) above those known from the well characterised High Amylose Glacier (AC38) mutant (45-48%)(Walker et al., 1968), and have starch with an amylopectin structure that has an increase in starch branch frequency, this is in contrast to the reduced branch frequency associated with the amylose extender mutant in maize (Takeda, et al., 1993).

The grain and starch characteristics of the present mutant have been investigated in detail and the causal mutation mapped. The mutations isolated are allelic to the previous known shrunken mutant in barley, sex6, and the causal mutation has been shown to be located within the starch synthase II gene. The effects of this mutation shed new light on the process of starch biosynthesis and illustrate how mutations in specific genes can have differing impacts on starch structure from one species to another.

Materials and Methods
Mutagenesis and Screening

The hull-less barley variety "Himalaya" was mutagenised using sodium azide according to Zwar and Chandler (1995).

Selection of variants with altered grain morphology was carried out according to Green et al., (1997). A total of 75 lines with shrunken endosperm phenotypes were identified and maintained according to Green et al., (1997).

Starch Isolation

Starch was isolated from barley grain using the method of Schulman et al. (1991).

Methods for Amylose Determination

Determinations of the amylose/amylopectin ratio by an HPLC method for separating debranched starches, and an iodine binding method, were carried out as described by Batey and Curtin, (1996). Analysis of the amylose/amylopectin ratio by the analysis on non-debranched starches was carried out according to Case et al., (1998).

Starch Content Measurement

Starch was determined using the total starch analysis kit supplied by Megazyme (Bray, Co Wicklow, Republic of Ireland).

Protein Content

Nitrogen was determined by the Kjeldahl method, and protein contents were calculated using a factor of 5.7.

β-Glucan Levels

β-Glucan was determined using the kit supplied by Megazyme (Bray, Co Wicklow, Republic of Ireland).

Starch Chain Length Distribution

Starches were debranched and chain length distributions analysed using flurophore assisted carbohydrate electrophoresis (FACE) using a capillary electrophoresis according to Morell et al (1998).

DSC

Gelatinisation was measured in a Pyris 1 differential scanning calorimeter (Perkin Elmer, Norwalk Conn., USA). Starch was mixed with water in the ratio of 2 parts water:1 part starch and this mixture (40-50 mg, accurately weighed) was placed in a stainless steel pan and sealed. The sample was scanned at 10° C. per minute from 20° C. to 140° C. with an empty stainless steel pan as a reference. Gelatinisation temperatures and enthalpy were determined using the Pyris software.

RVA Analysis

Viscosity was measured on a Rapid-Visco-Analyser (RVA, Newport Scientific Pty Ltd, Warriewood, Sydney) using conditions as a reported by Batey et al., 1997 for wholemeal flours. In order to inhibit a-amylases, silver nitrate was included in all assays at a concentration of 12 mM. The parameters measured were peak viscosity (the maximum hot paste viscosity), holding strength, final viscosity and pasting temperature. In addition, breakdown (peak viscosity minus holding strength) and setback (final viscosity minus holding strength) were calculated.

Flour Swelling

Flour swelling volume was determined according to the method of Konik-Rose et al (2001).

X-Ray Data

X-ray diffraction data was collected using standard techniques (Buleon et al., 1998).

Scanning Electron Microscopy

Scanning electron microscopy was carried out on a Joel JSM 35C instrument. Purified starches were sputter coated with gold and scanned at 15 kV at room temperature.

Doubled Haploid Production

Doubled haploids were produced from F1 plants derived from crosses between 292 and *Hordeum vulgare* cv Tantangara, and between 342 and *H. vulgare* cv Tantangara by Dr P. Davies, Waite Institute, Adelaide, Australia.

Linkage Analysis

Genetic linkage data was calculated using MapManager.

Construction of Barley cDNA Library

Five mgs of polyA+mRNA from 10, 12 and 15 days post-anthesis of barley endosperm tissues was used for cDNA synthesis according to the protocols (Life Technology). The NotI-(dT)18 primer (Pharmacia Biotech) was used for the first stand of cDNA synthesis. The double strand cDNAs were ligated with a SalI-XhoI adapter (Stratagene) and cloned to the SalI-NotI arms of ZipLox (Life Technology) after digestion of cDNAs with NotI followed by size fractionation (SizeSep 400 spun Column of Pharmacia Biotech). The ligated cDNAs were packaged with Gigapack III Gold packaging extract (Stratagene). Titre of the library was $2 \times 10^6$ pfu tested with Y1090(ZL) strain of E. coli.

Cloning of Specific cDNA Regions of Barley Starch Synthase II Using PCR

The cDNA clone, wSSIIp1, was used for the screening of a cDNA library of barley. The cDNA clone, wSSIIp1 was generated by PCR using the primers ssIIa (TGTTGAGGTTCC ATGGCACGTTC SEQ ID NO 11) and ssIIb (AGTCGTTCT-GCCGTATGATGTCG SEQ ID NO 12), amplifying the region between nucleotide positions 1,435 and 1,835 of wSSIIA (GenBank accession no: AF155217).

The amplification was performed using a FTS-1 thermal sequencer (Corbett, Australia) for 1 cycle of 95° C. for 2 minutes; 35 cycles of 95° C. for 30 seconds, 60° C. for 1 minutes, 72° C. for 2 minutes and 1 cycle of 25° C. for 1 minute. The fragment wSSITp1 was cloned into a pGEM-T vector (Promega)

Screening of Barley cDNA Library

A cDNA library, constructed from RNA from the endosperm of barley cv Himalaya, was screened with a 347-bp cDNA fragment, wSSIIp1 at the hybridisation conditions as previously described (Rahman et al., 1998). Hybridisation was carried out in 50% formamide, 6×SSPE, 0.5% SDS, 5×Denhardt's and 1.7 µg/mL salmon sperm DNA at 42° C. for 16 h, then washed 3× with 2× SSC containing 0.1% SDS at 65° C. for 1 h per wash.

Screening of a Barley Genomic Library.

A barley (barley cv Morex) genomic library was constructed and screened essentially as described in Gubler et al (2000) using the barley SSII cDNA as a probe.

Sequencing of Genomic Clones

The Morex SSII gene was subcloned into plasmid vectors and sequenced. The 292 and MK6827 genes were sequenced by PCR amplification of overlapping regions of the gene using primers designed on the basis of the Morex sequence. PCR fragments were either sequenced directly or subcloned and sequenced from plasmids Identification of Expressed Regions Regions of the 292 and MK6827 genomic sequences predicted to be present in cDNAs were defined by reference to the Himalaya cDNA sequence and Morex genomic sequence.

PCR Analysis of the G to A Mutation in the SSII Gene

PCR primers were designed that amplify the region containing the G to A transition mutation identified in 292. The primer sequences are: ZLSS2P4 (CCTGGAACACTTCA-GACTGTACG SEQ ID NO 13) and ZLBSSII5 (CTTCAGG-GAGAAGTTGGTGTAGC SEQ ID NO 14). The amplification was performed using a FTS-1 thermal sequencer (Corbett, Australia) for 1 cycle of 95° C. for 2 minutes; 35 cycles of 95° C. for 30 seconds, 60° C. for 1 minutes, 72° C. for 2 minutes and 1 cycle of 25° C. for 1 minute.

SDS-PAGE Analysis of Burley Endosperm Proteins

Starch was prepared from the developing and mature endosperm of barley and wheat and the surface proteins were removed by proteinase K as described (Rahman et al, 1995). Starch granule proteins were extracted from 20 mg of starch dry wt., using 0.5 ml of an extraction buffer containing 50 mM Tris pH 6.8, 10% SDS and 10% 2-mercaptoethanol. After gelatinization by boiling for 10 min, and collection of the starch by centrifugation, 15 microliters of the supernatant was loaded on each lane.

Doubled Haploid Production

Doubled haploids were produced from F1 plants derived from crosses between 292 and Hordeum vulgare cv Tantangara, and between 342 and H. vulgare cv Tantangara by Dr P. Davies, Waite Institute, Adelaide, Australia.

Backcrossing Strategy

Crosses were made between 292 and Hordeum vulgare cv Sloop to generate F1 seed. Plants derived from the F1 seed were selfed to generate a population of F2 seed. The plants growing from these F2 seed were tested using a PCR assay and plants homozygous for the 292 mutation were backcrossed to Sloop (BC1). The F1 plants resulting from BC1 were again tested by PCR and plants heterozygous for the 292 mutation selected, and crossed back to Sloop (BC2). The F1 plants derived from BC2 were again analysed by PCR and plants heterozygous for the 292 mutation selected. These plants were either selfed to generate a BC2F2 population, or crossed again to Sloop (BC3). The F1 plants derived from BC3 were again analysed by PCR and plants heterozygous for the 292 mutation selected. These plants were selfed to generate a BC3F2 population. Plants derived from these seed were tested by PCR and plants homozygous for the 292 mutation selected for single seed descent and seed increase.

Results

Selection of Mutants

The identification of a range of mutants in the hull-less or naked barley variety "Himalaya" induced by a sodium azide treatment has been previously reported by Zwar and Chandler (1995). A group of 75 shrunken grain mutants were identified by the inventors and the amylose content of the starch from the shrunken seed was determined by HPLC (FIG. 1). Two lines, 292 and 342, were found to have amylose contents of 71 and 62.5% respectively (Table 1). The amylose contents of 292 and 342 were substantially higher than the previously well characterised AC38 line (47% amylose, see Table 1). This study defines the genetic basis of the novel high amylose phenotype displayed by 292 and 342, and describes effects of the causal mutation on grain and starch structure and functionality.

Grain Characteristics

Figure 2:
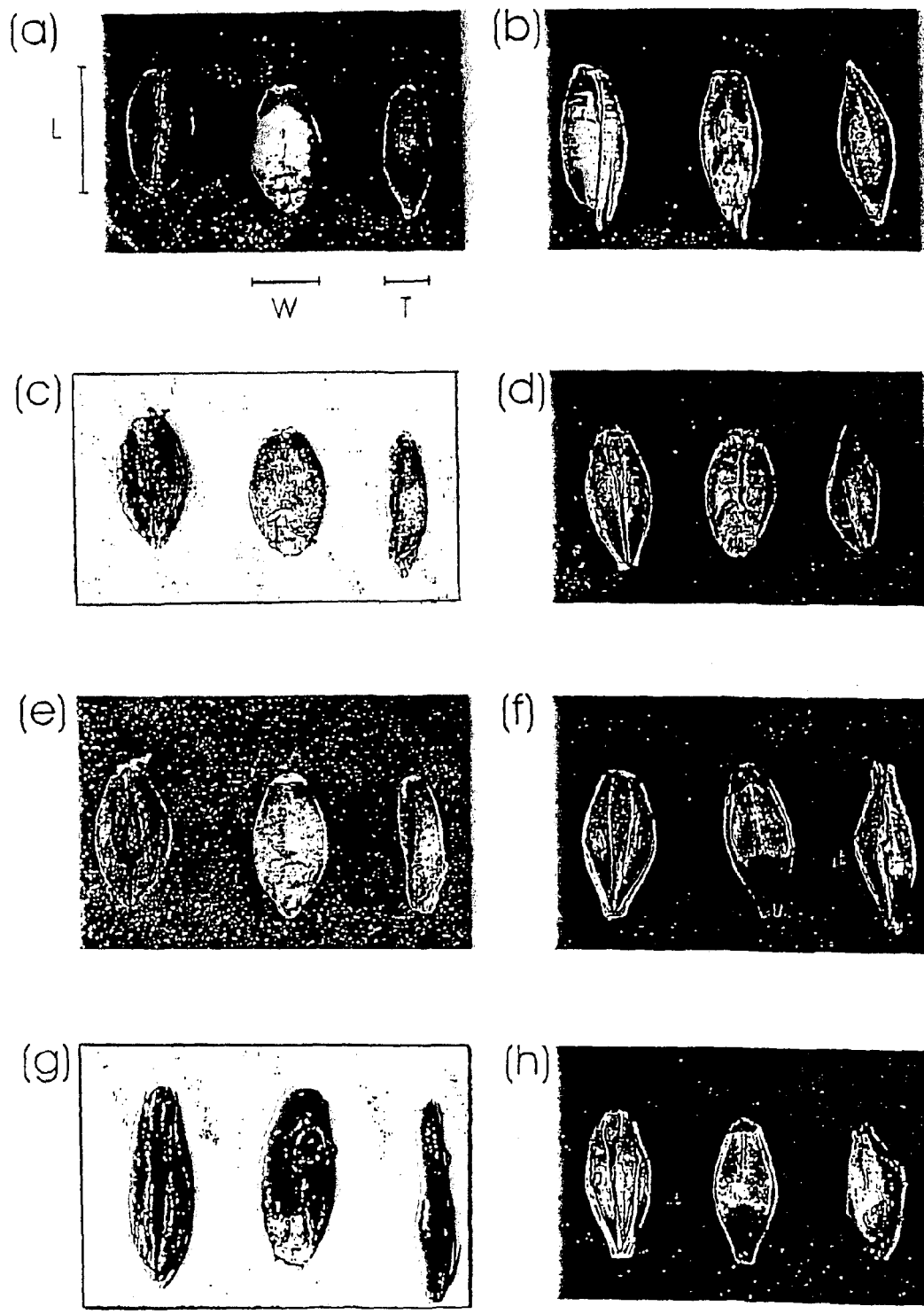
FIG. 2 Photographs showing the grain morphology of mutant and parental lines. (a) Himalaya (b) AC38 (c) 292 (d) Waxiro (e) 342 (f) Tantangara (g) MK6827 (h) Sloop. The length (L), width (W) and thickness (T) dimensions of the grain are illustrated in panel (a).

Grain Size and Morphology:

The effects of the mutation on grain weight and morphology are marked (Table 2). The grain weight is reduced from 51 mg for the parent line Himalaya, to 32 mg for 292 and 35 mg for 342. The mutants retain the length and width of the wild type, but in comparison are flattened (from 2.82 mm average thickness in Himalaya to 1.58 and 1.75 mm in 292 and 342 respectively) and have an essentially unfilled central region. FIG. 2 shows photographs of the mutant and wild-type grain. The dimensions of the grain were routinely measured, the length of the grain (L), the width of the grain at the widest point (W), and the thickness (T) as indicated in FIG. 2. The ratio of length (L) to thickness (T) of the grain is a useful diagnostic for the mutation, with values of >3.5 typically found for seed carrying the 292 or 342 mutations, and values <3.5 for non-mutant barleys.

Grain Composition:

The starch content of the mutant lines is reduced from 49.0% for Himalaya to 17.7 and 21.9% for 292 and 342 respectively (see Table 1). Subtraction of the starch weight from total grain weight to give a total non-starch content of the grain, showed that the loss of starch content accounted for the loss of grain weight, with non-starch weights of 26.0, 26.3 and 27.3 mg for Himalaya, 292 and 342 respectively.

The protein content of 292 and 342 is increased relative to the parent line, Himalaya (Table 1) however, this effect is due to the loss of starch from the grain and is not due to any increase in protein synthesis per caryopsis.

The β-glucan levels of the 292 and 342 mutants are also increased, and are higher than would be expected from the effect of the reduction of starch content (Table 1). In both cases, β-glucan content is increased about 20% per caryopsis, possibly representing diversion of a small proportion of incoming carbon from starch synthesis to β-glucan synthesis.

Starch Composition and Functionality
Amylose and Amylopectin Content

Amylose content was determined using two techniques, firstly, size exclusion HPLC in 90% (v/v) DMSO, and secondly, iodine blue value. The amylose contents determined by each method were similar and the HPLC data are given in Table 1.

From grain weight and amylose content data for mutant and wild type lines, calculations of the amount of amylose deposited per grain can be made. This analysis shows that there is a decrease in amylose amount per grain from 6.2 mg/caryopsis in Himalaya, to 4.0 mg/caryopsis in 292 and 4.8 mg/caryopsis in 342. In contrast, there is a dramatic reduction in amylopectin synthesis per caryopsis, from 18.7 mg in Himalaya, to 1.6 mg in 292 and 2.9 mg in 342.

Chain Length Distribution

Figure 3:
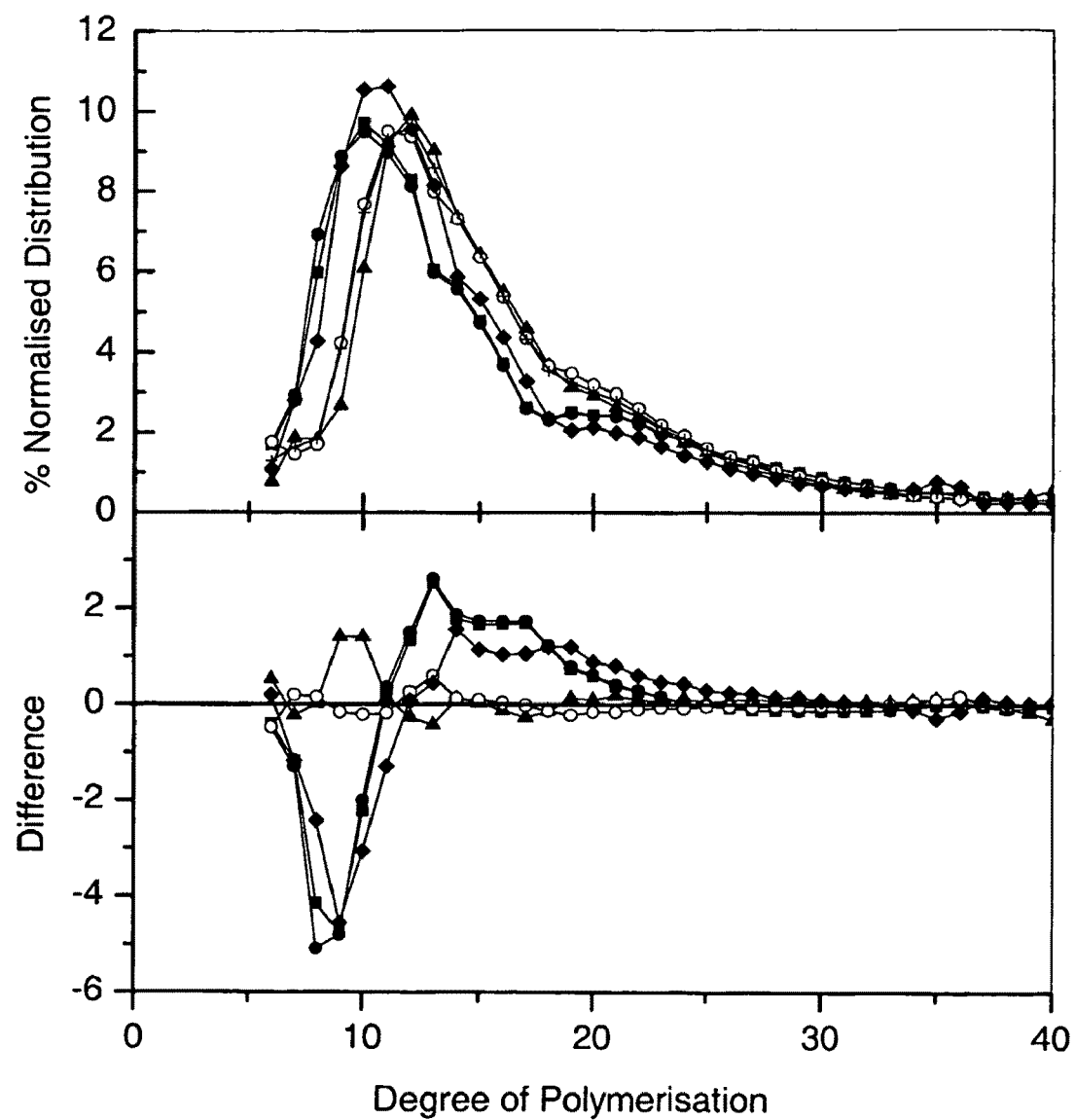
FIG. 3 Analysis of the chain length distribution of various mutant and wild type starches using FACE. (a) normalised chain length distribution (b) comparison of chain length distributions by difference plot. Samples were 342 (■), 292 (●), Tantangara (s), AC38 (⊕), MK6827 (♦) and Himalaya (+).

The chain length distribution of the starch following isoamylase debranching was carried out using fluorophore-assisted carbohydrate electrophoresis (FACE). The chain length distribution of the 292 and 342 mutants, and Himalaya, are shown in FIG. 3a. FIG. 3b shows a difference plot in which the normalised chain length distributions for the 292 and 342 mutants are subtracted from the normalised distribution of Himalaya. The percentages of chain lengths from DP 6-11, DP 12-30 and DP 31-65 have been calculated and are presented in Table 3. There is a marked shift in the 292 and 342 mutants in chain length distribution such that there is a higher percentage of chains in the region from DP6-11 compared to DP12-30.

Differential Scanning Calorimetry

The gelatinisation temperature of the mutants was investigated using differential scanning calorimetry, and the data is shown in Table 4. Both 292 and 342 yield starches that have markedly lower gelatinisation temperatures than the Himalaya starches, with respect to onset, peak and final temperatures for the gelatinisation peak. The enthalpy for the gelatinisation peak for the 292 and 342 mutants is also dramatically reduced in comparison to the wild type. The amylose/lipid peak onset temperature is also reduced for the 292 and 342 mutants, however, the enthalpy is increased, consistent with the increased amylose content of the mutants.

Starch Viscosity by RVA

Figure 4:
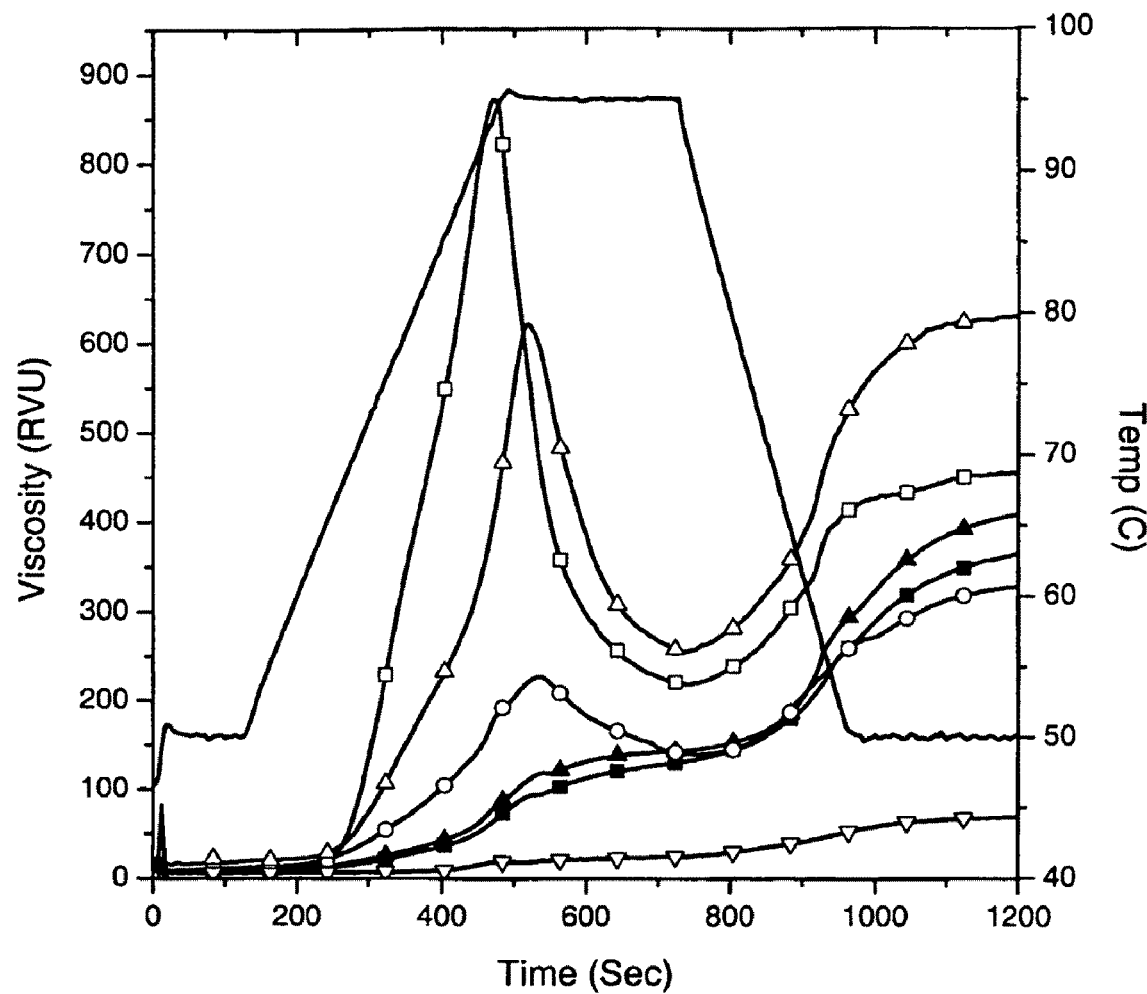
FIG. 4 RVA analysis of barley starch samples. Samples were Himalaya (⊕), Namoi (Δ), AC38 (○), 342 (▼), 292 (▲) and MK6827 (■). The temperature profile used during the profile is indicated by the unbroken line.

RVA analysis of barley wholemeal samples was conducted in order to examine their pasting viscosity. Previous studies have shown that analysis of wholemeal samples is strongly correlated with the analysis of isolated starches (Batey et al., 1997). The analysis showed that there are major differences between the barley genotypes studied (see Table 5 and FIG. 4). Two barley varieties containing wild type starch, Himalaya and Namoi, showed typical RVA profiles in which there was a prominent peak viscosity, followed by a decline in viscosity to a holding strength, followed by an increase in viscosity as the temperature is reduced to a final viscosity. As is generally observed for barley starches, the final viscosities for the wild type starches were equivalent to, or less than, the peak viscosities (Table 5). In AC38, a prominent peak viscosity was obtained, however, because of the elevated amylose content of this line, the final viscosity obtained was higher than the peak viscosity. However, in 292, 342 and MK6827, a very different profile was obtained. No marked initial increase in viscosity corresponding to the peak viscosity in other barley starches was obtained, and therefore no value for breakdown could be calculated. The values for peak viscosity given in Table 5 for 292, 342 and MK6927 were the viscosities registered at the time of peak viscosity for Himalaya. In 292, 342 and MK6827, viscosity increased throughout the analysis to reach a final viscosity comparable to the other wholemeal samples. When normalized on the basis of starch content, the 292 and 342 starches had very high final viscosities (see Table 5).

Swelling volume is a method of measuring the properties of flour and starch that probes the behaviour of the material on exposure to heat and excess water. Increased uptake of water is measured by weighing the sample prior to and after mixing the sample in water at defined temperatures and following collection of the gelatinized material. The analysis showed that the control samples, Himalaya and Tantangara, swell to 6 to 8 times their dry weight, in contrast, 292 and 342 swell to just 2-3 times their dry weigh (Table 9).

Crystallinity

Figure 5:
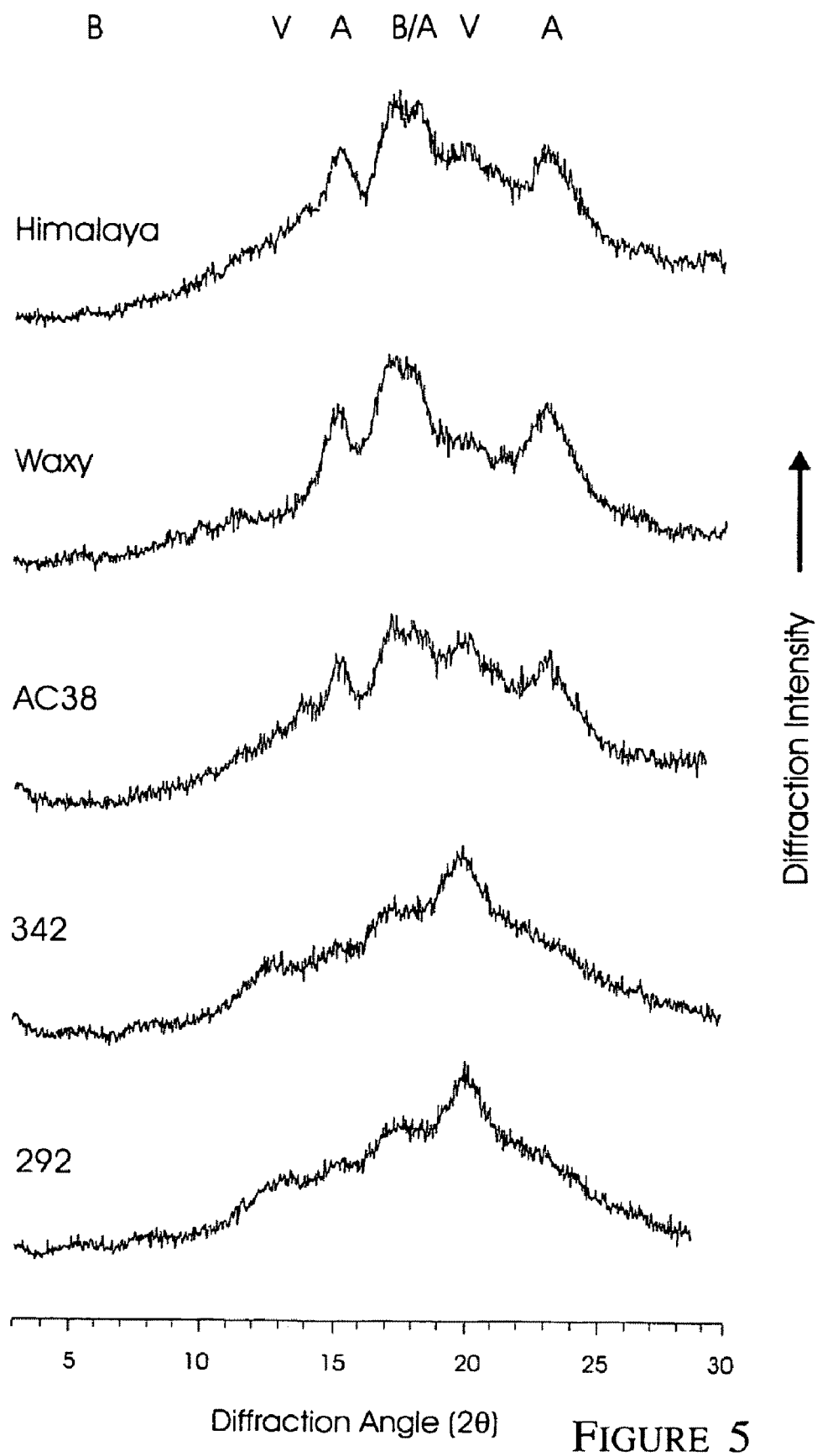
FIG. 5 X-ray diffraction data for mutant and wild type lines.

The structure of the starches was further investigated by X-ray crystallography (see Table 6 and FIG. 5). Himalaya shows the expected pattern for a cereal starch, having predominantly "A" type crystallinity, and both AC38 and Waxiro showed very similar X-ray diffraction patterns, although the levels of crystallinity were lower for AC38 and higher for Waxiro. For the 292 and 342 mutants, the X-ray diffraction pattern shifted to a mixture of V and B pattern. In addition to the shift in diffraction pattern, the amount of crystallinity was sharply reduced in the 292 and 342 mutants, to 9 and 12% respectively. This result is consistent with the low amylopectin content of the 292 and 342 starches.

Granule Morphology

Figure 6:
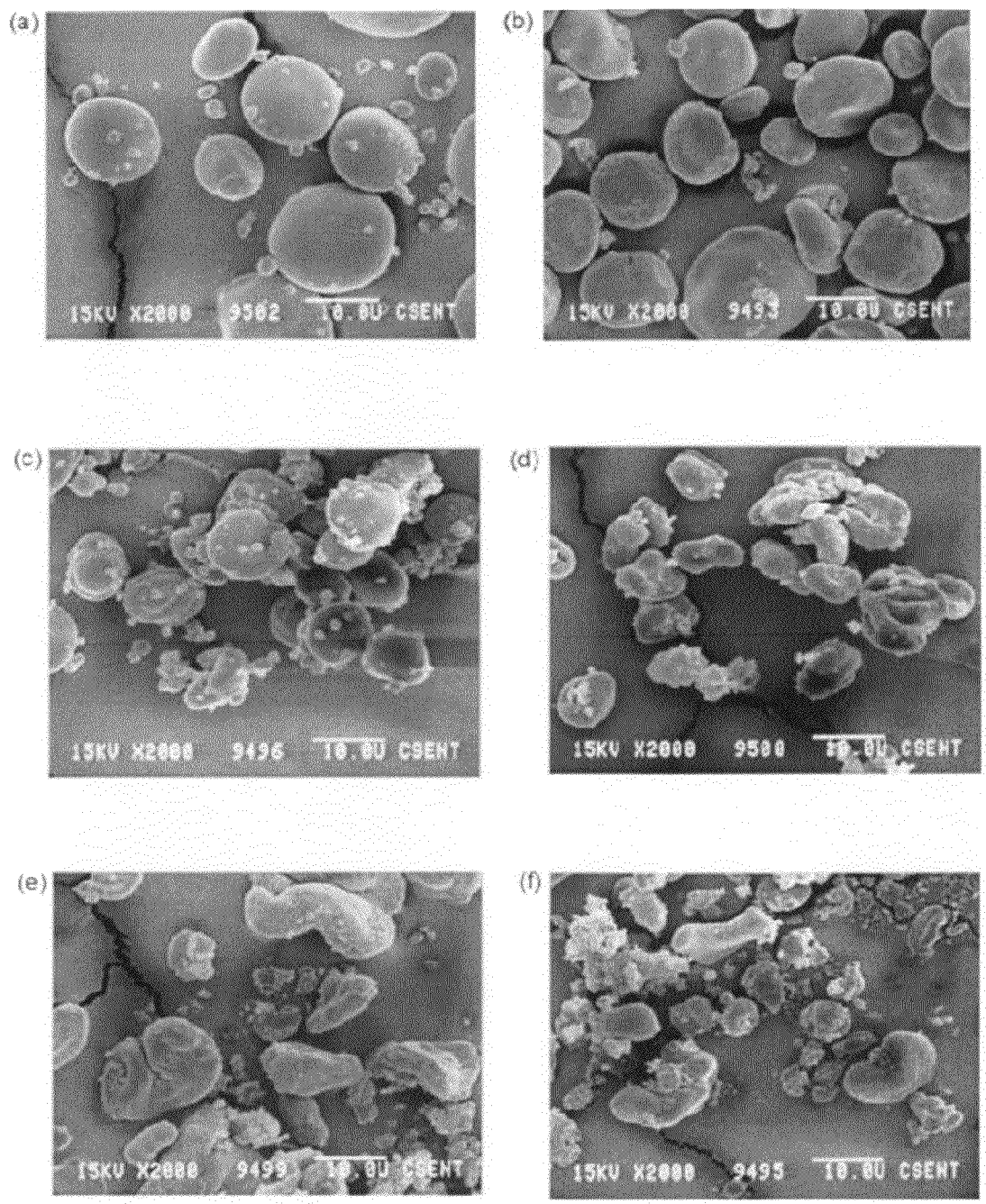
FIG. 6 Scanning electron micrographs of isolated barley starches. (a) Himalaya (b) Waxiro (c) AC38 (d) 292 (e) 342 (f) MK6827

Starch granule morphology was investigated using scanning electron microscopy (FIG. 6). The size and shape for granules from Himalaya (FIG. 6, panel A), waxy barley (Waxiro, FIG. 6 panel b), and AC38 (FIG. 6, panel c) were consistent with previously published observations of starch granules in normal barley lines. The morphology of "A" type starch granules in the mutant lines 292 (FIG. 6, panel d), 342 (FIG. 6, panel e), and MK6827 (FIG. 6, panel f), is clearly altered with the granules having a convoluted surface in comparison to the smooth lenticular shape of the normal barleys.

Dietary Fibre

Dietary fibre analysis was conducted according to the AOAC procedure and showed that there was an increase in dietary fibre in 292 and 342, and that this increase in dietary fibre was due to an increase in insoluble dietary fibre rather than soluble dietary fibre (Table 1), consistent with components of the dietary fibre being resistant starch and β-glucan. It is to be noted that this measure of dietary fibre is a chemically determined one which is quite distinct form the physiological measure relevant from a nutritional point of view.

Genetic Basis of the Mutation
Segregation Ratio

Crossing of the mutation to barley varieties not displaying the shrunken endosperm phenotype of 292 or 342 demonstrated that the mutation is a straightforward recessive mutation, displaying a 3 normal:1 shrunken ratio in the F2 seed of outcrossed populations, and 1 normal:1 shrunken ratio in the seed of a doubled haploid population developed following a single outcross (see Table 6). Normal is defined as seed with an L/T ratio of <3.5, shrunken seed as seed with an L/T ratio of >3.5.

Allelic Nature of Mutants

The 292 and 342 mutations were shown to be allelic through the analysis of progeny from crosses of 292 and 342. All F1 seed derived from reciprocal crosses showed grain weight and grain morphology phenotypes within the range of sizes and shapes observed for the parental 292 and 342 lines, and outside of the range of seed size and shape found for the parental Himalaya line. Furthermore, all F2 seed derived from 292×342 F1 plants showed the typical shrunken seed phenotype of the 292 and 342 mutants.

Analysis of the grain morphology and starch characteristics of a series of shrunken grain mutants available from the Barley Germplasm Collection (USDA-ARS, National Small Grains Germplasm Research Facility, Aberdeen, Id. 83210, USA) suggested that the line MK6827 (BGS31, also referred to as GSHO 2476), carrying the sex6 mutation showed a highly similar set of starch and grain characteristics to the 292 and 342 mutations. Crosses were established between 292 and MK6827 and all F1 grain showed the typical 292 phenotype with respect to grain weight and shrunken seed phenotype. F2 seed derived from the 292×MK6827 F1 plants all showed shrunken endosperm phenotype with L/T ratios of >4. In contrast, F2 seed from a cross between 292 and the commercial barley cultivar Sloop yielded a bimodal distribution showing a 3:1 segregation ratio between shrunken and filled seed (Table 6). F1 seed generated from crosses of 292 and 5 other lines with shrunken endosperm phenotypes (BGS 380, shrunken endosperm 4, 7HL (Jarvi et al., 1975); BGS 381, shrunken endosperm 5, 7HS (Jarvi et al., 1975); BGS 382, sex1, 6HL (Eslick and Ries 1976); BGS 396, Shrunken endosperm 6, 3HL (Ramage and Eslick 1975); BGS 397, Shrunken endosperm 7, not mapped, (Ramage and Eslick 1975) all yielded grain with a filled seed morphology. On this basis, the 292, 342 and MK6827 mutations are considered to be allelic, and on the basis of previously published map locations for the sex6 locus, the 292 and 342 mutations would be predicted to map to the short arm of chromosome 7H in barley, about 4 cM from the centromere (Netsvetaev, 1990, Netsvetaev and Krestinkov, 1993, Biyashev et al., 1986, Netsvetaev, 1992).

Linkage Analysis

A doubled haploid population was generated from a cross between 292 and the commercial malting barley variety, Tantangara, which contained 90 progeny lines (Table 8).

The lines were scored for seed morphology (filled versus shrunken seed), chain length distribution by FACE (percentage of chains with DP 6 to 11), seed covering (naked or husked), and for a PCR marker (see below). This data is given in Table 8. The shrunken seed character and 292 FACE distribution co-segregated precisely in this population, as would be expected if the altered grain size and shape were a consequence of altered starch deposition. The co-segregation of characters is illustrated in FIG. 8. Panel A shows the relationship between starch chain length (illustrated by the percentage of chains between DP 6 to 11) and the length to thickness ratio. The open circles indicate lines that have the PCR marker for the 292 mutation, the crosses indicate lines that carry the wild type PCR marker. There is a clear definition between the two groups of lines. FIG. 8 Panel B shows the relationship between starch chain length and seed weight, and shows that seed weight is less diagnostic for the mutation that the length to thickness ratio.

In barley the presence or absence of the husk is controlled by the nud locus located on chromosome 7H, and as Tantangara is a husked barley and 292 is a naked type, this character could be scored in the doubled haploid progeny. Analysis of the linkage between the naked/husked character and FACE data showed that in this cross the 292 mutation was mapped within 16.3 cM of the nud locus. This location is consistent with previous mapping data for the allelic sex6 mutation (Netsvetaev, 1990, Netsvetaev and Krestinkov, 1993, Uiyashev et al., 1986, Netsvetaev, 1992).

Identification of the Causal Gene

Figure 10:
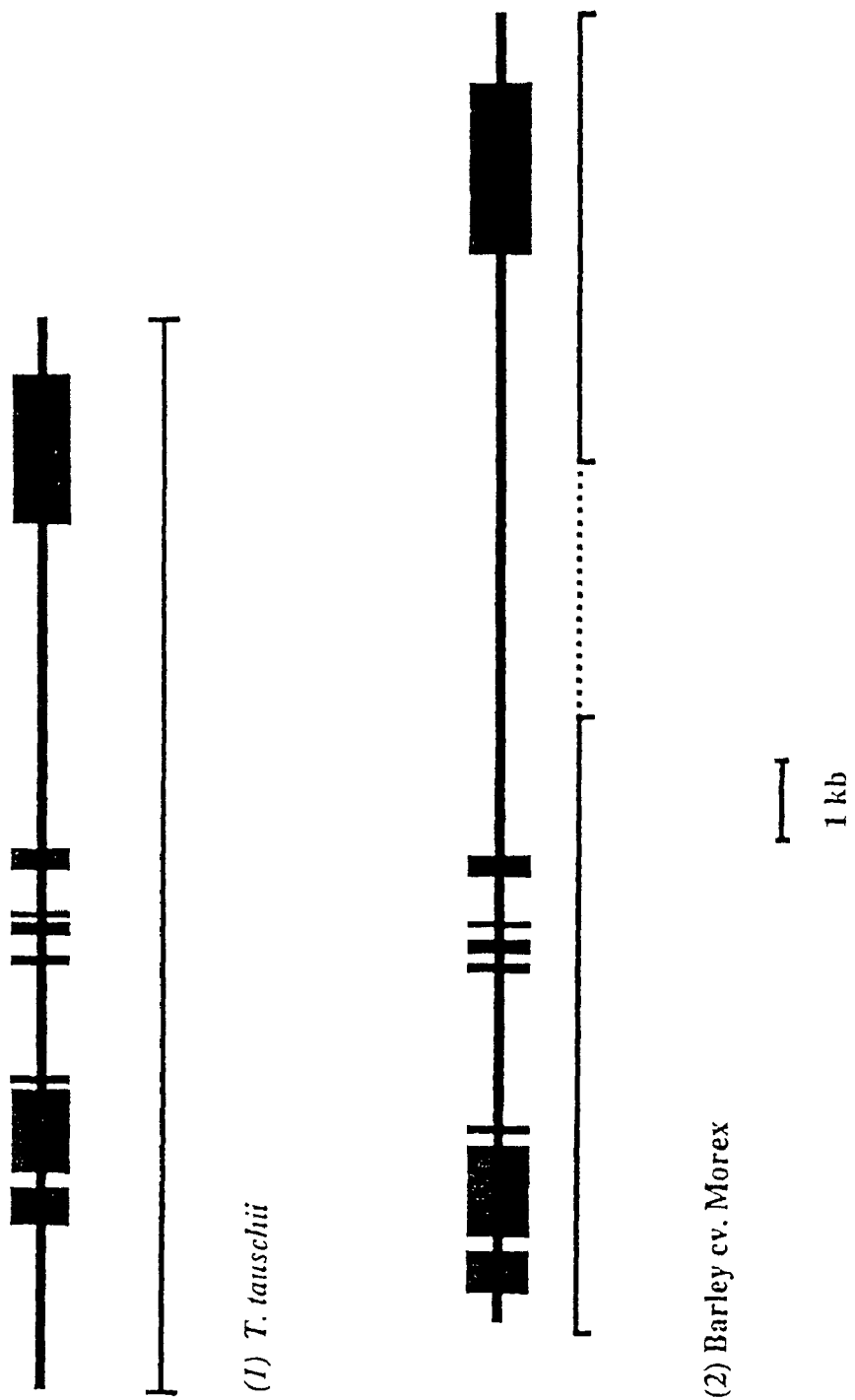
FIG. 10 The structure of the SSII genes from (1) *T. tauschii* (diploid wheat), (2) barley cultivar Morex. The thick lines represent exons and the thin lines introns. The straight line underneath each example indicates the region of the gene sequences. The dotted line represents a region of the barley SSII gene, from intron 7, that has not been sequenced but has been determined by PCR analysis to be approximately 3 kb in length.
Figure 13:
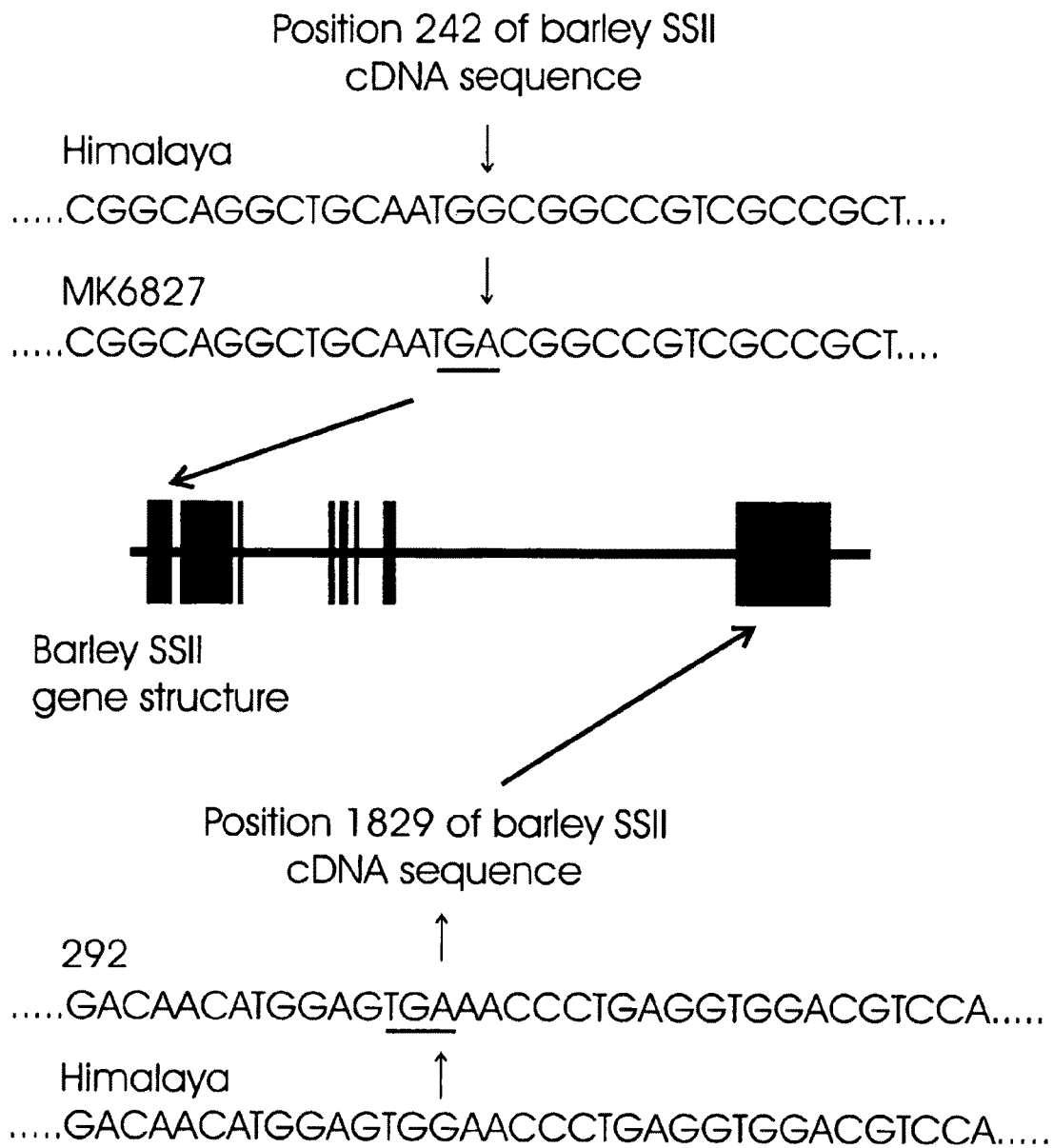
FIG. 13. Position of the mutations in MK6827 (SEQ ID NO 2) and 292 (SEQ ID NO 4) in the barley SSII gene.

The nud gene has been demonstrated to be located on barley chromosome 7H (FIG. 8, Fedak et al., 1972). In wheat, three starch synthases (GBSS, SSI and SSII), and an isoamylase-type debranching enzyme (S. Rahman, personal communication) are located on the short arm of chromosome 7, the homologous chromosome (Yamamori and Endo, 1996, Li et al., 1999a, Li et al., 1999b, Li et al., 2000). The close linkage to the nud locus suggested that the most probable candidate gene was the SSII gene. The wheat SSII gene has been cloned at the cDNA level (Li et al, 1999b; Genbank Accession No. AF155217) and at the genomic level (Li et al., personal communication), and a barley cDNA has been isolated and cloned (FIG. 9). The sequencing of barley and wheat SSII genomic sequences shows that the genes have very similar exon/intron structures, however, the lengths of the intron regions differ between sequences (FIG. 10). Comparison of the Morex genomic sequence and the sequence of a cDNA from Himalaya (FIG. 9) lead to the identification of deduced cDNA sequences from Morex, 292 and MK2827.

A G to A transition mutant was found in the SSII gene from 292 at a position that corresponds to 1829 of the alignment shown in FIG. 11. This mutation introduces a stop codon into the 292 SSII open reading frame (FIG. 12). Sequence analysis of Tantangara and Himalaya showed that both wild type genes were identical in this region and both 292 and 342 contained the same G to A transition mutation. The introduced stop codon would truncate the gene product such that the entire C-terminal catalytic domain of the starch synthase II gene would not be translated, and it is therefore highly likely that all SSII activity is abolished by this mutation.

A G to A transition was also present in MK6827, at position 242 of the alignment shown in FIG. 11 and the Himalaya cDNA sequence in FIG. 9. This mutation also introduces a stop codon into the 292 SSII open reading frame (FIG. 12) and would prevent translation of over 90% of the SSII gene, abolishing SSII activity encoded by this gene.

The G to A transition mutation in 292 disrupted a restriction site (NIaIV) in the barley SSII gene. The location of the diagnostic NIaIV site is shown in FIG. 14, panels (a) and (b). FIG. 14c shows agarose gel electrophoresis of NIaIV digested products from barley showing that the diagnostic pattern for the 292 mutation is in 292 and 342 but not MK6827, Himalaya or Tantangara.

The PCR marker for the G to A transition was scored in the 90 lines of the 292× Tantanagara doubled haploid population and found to co-segregate precisely with the shrunken seed and FACE chain length distribution phenotypes, indicating that the 292 mutation is perfectly linked to this starch phenotype and that it is highly probable that this mutation is the causal mutation underlying the 292 phenotype. FIG. 14d shows the analysis of lines from the 292× Tantangara doubled haploid population.

Biochemical Evidence for Loss of SRI Activity

The composition of starch biosynthetic enzymes in the mutant and normal barley lines was investigated using a range of gel electrophoresis techniques. Analysis of the soluble fraction of the developing endosperm demonstrated that all lines contained BEI, BEIIa, BEIIb, SSI and SSIII and that the content of these isoforms of BE and SS respectively were essentially unaltered. However, analysis of the starch granule indicated that several bands were missing. Firstly, SDS-PAGE analysis (FIG. 16, panel B) showed that a band of 90 kD was not present in 292, 342 or MK6827 that was present in Himalaya, Tantangara and AC38. This band was shown by immunoblotting to contain SSII (FIG. 16, panel B) and BeIIa and BEIIb. The finding that BEIIa and BEIIb are present in the soluble fraction but not the granule indicates that there has been an alteration in the distribution of these enzymes in the 292, 342 and MK6827 mutants, rather than a mutation abolishing expression. In contrast, no evidence was found for SSII expression in either the soluble or the granule fraction (FIG. 16, panels A and B), consistent with the genetic evidence directly linking the SSII mutation to the observed phenotypes in 292, 342 and MK6827.

Breeding of Lines Carrying the 292 Mutation

Two strategies have been used to transfer the 292 mutation into alternative barley genotypes.

In the first example, doubled haploid lines were generated from a cross between 292 and Tantangara. Data for seed covering, seed weight, L:T ratio, chain length distribution and SSII DNA marker status is given in Table 8. More comprehensive analysis of the composition of these lines is given in Table 9, including RVA analysis, β-glucan content and flour swelling volume. The data shows that the lines carrying the 292 mutation have significantly different RVA parameters (as exemplified by the Peak/Final Viscosity ratio), higher β-glucan content, and altered flour swelling volumes.

In the second example, the mutation was transferred by performing two backcrosses from 292 to a cultivar with normal starch properties (cv Sloop). The F2 seed from three backcross 2 F1 plants was collected for analysis. The F2 seed were categorized into seed with an L:T ratio of >3.5 and an L:T ratio of <3.5. The distribution of seeds between these classes was consistent with expectations for a single recessive gene. Flour swelling volume data for the categories of seeds derived from each plant are shown in FIG. 10 and shows that the starch swelling trait was clearly transferred through the breeding process into lines with an average of 75% Sloop background.

Discussion

We describe the isolation of novel mutants, 292 and 342, in barley that have a shrunken endosperm phenotype. Analysis of grain composition demonstrates that the shrunken phenotype is due to a significant decrease in starch content, and analysis of starch composition shows that this decrease is manifested as a high amylose phenotype that arises because of a decrease in amylopectin synthesis.

The 292 and 342 mutants possess a unique combination of grain and starch properties, in containing both increased β-glucan levels and resistant starch. The β-glucan levels of the lines are increased approximately 15% above that expected by the effect of reduced starch content, suggesting that carbon unable to be converted to starch is diverted to β-glucan synthesis. Determinations of dietary fibre levels demonstrate that the grain from the mutants have increased levels of dietary fibre, and that this increase is due to an increase in insoluble dietary fibre.

This combination of properties indicates that these mutants may have very interesting potential as components of the human diet. First, the elevated β-glucan levels suggests that the lines may be useful in lowering cholesterol through the well established action of β-glucan in reducing cholesterol levels. Secondly, the presence of resistant starch indicates that the lines may be beneficial from a bowel health perspective through the well established ability of resistant starches to promote colonic fermentation (Topping et al., 1997, Topping 1999). Thirdly, the grain composition indicates that the lines will have low energy density and that they may be slowly digested, indicating that they may contribute to the formulation of foods with a reduced glycaemic index.

The starch properties of the exemplified lines are also unique in that they combine a high amylose starch that also has a low gelatinisation temperature. This contrasts with high amylose mutations resulting from mutations in branching enzyme lib in which gelatinisation temperature typically increases, such as the amylose extender mutation in maize (Ng et al., 1997, Katz et al., 1993, Krueger et al., 1987, Fuwa et al., 1999). While the amylose content of 292 is comparable to amylose extender lines, the structure of the amylopectin component of the starches differs dramatically (Wang et al., 1993). In 292 and 342, the chain length distribution of amylopectin shifts towards lower degree of polymerisation, whereas in amylose extender, the chain length distribution shifts towards increased degree of polymerisation. This suggests that amylopectin, rather than amylose content, is the primary determinant of gelatinisation temperature and that this effect is mediated through the strength of the interaction between the external chains of the amylopectin molecule. Similar effects were noted for a range of starches by Jane et al., 1999.

The viscosity data from the RVA analysis indicate that the starch from the SSII mutant lines is marked different from normal barleys and AC38. The SSII mutant barleys have essentially no peak of viscosity typically seen as the temperature is ramped up to 95° C. at the beginning of an RVA temperature profile. Instead, in these mutants, the viscosity increases steadily until a final viscosity if present. These data are consistent with the low amylopectin content of the granules, the low level of amylopectin crystallinity in the granule, and the low gelatinisation temperature and enthalpy observed in the differential scanning calorimeter. A high final viscosity is reached once the amylose has been released from the granule through heating in excess water, and stirring. These RVA characteristics are unique for a cereal starch and provide a novel source of starch for food and industrial applications where low pasting viscosity yet high final viscosity is required.

The observations made on gelatinisation temperature in the DSC are reflected in results from X-ray diffraction studies. The granules of 292 and 342 have reduced levels of crystallinity and the crystal form shifts from the A type typical of cereal starches to a mixture of V and B types. The V type is typical of amylose and reflects the amylose component of the starch complexed with fatty acids, while the B form is derived from amylopectin and presumably reflects the residual amylopectin content of the starch (Buleon et al, 1998).

Analysis of the genetic basis of the 292 and 342 mutations demonstrates that the mutations are simple recessive mutations that give typical Mendelian ratios in outcrossing experiments. Crossing studies demonstrated that 292 and 342 are allelic. Further analysis of the interaction between 292 and other shrunken endosperm mutations in crossing experiments demonstrated that the 292/342 mutations were also allelic with the Sex6 mutation in the line MK6827. This mutation has previously been mapped and shown to be located within 3 cM of the centromere on the short arm of chromosome 7H (Netsvetaev, 1990, Netsvetaev and Krestinkov, 1993, Biyashcv et al., 1986, Nctsvetaev, 1992).

A doubled haploid population between the husked barley Tantangara and the naked 292 mutant was established and the shrunken endosperm mutation mapped to the short arm of chromosome 7HS, to within 16 cM of the nud gene, a location consistent with the map location of the Sex6 mutation.

The localisation of the gene to the region adjacent to the centromere on the short arm of chromosome 7HS demonstrates that the causal mutation (sex6) is in a different gene to the mutation that causes the high amylose phenotype in AC38 (amo1) which has been mapped to chromosome 1H (Schondelmeier et al 1992). The map location suggested that one candidate for the gene disrupted in the sex6/292 mutation was starch synthase II, known in wheat to be localised in the same region of the chromosome (Yamamori and Endo 1996, Li et al, 1999b). Sequence analysis of the 292 and 342 mutants showed that there was a G to A transition mutation in the gene which would cause truncation of the gene such that the C-terminal region containing the active site of the enzyme would not be translated, presumably leading to the synthesis of a completely inactive protein. Furthermore, the sequencing of the SSII gene from MK6827 showed a G to A transition mutation at position 242 which would also cause truncation of the gene. This result confirms the allelic nature of the 292 and MK6827 mutations.

The identification of mutations in the SSII gene lead to the development of a PCR marker diagnostic for the mutation in 292. This PCR marker was scored across the 91 progeny of the 292× Tantangara population and shown to 100% co-segregate with the shrunken endosperm phenotype and the reduced chain length distribution phenotype of starch. The discovery of allelic mutations in the SSII genes from barleys of diverse backgrounds (292 and MK6827) which give rise to similar phenotypes, and the perfect linkage of the mutation to the shrunken grain phenotype provides a high degree of certainty that the mutations present in the SSII genes of 292, 342 and MK6827 are the causal mutations leading to the shrunken endosperm character.

The phenotype observed here for the SSII mutation in barley is similar to the phenotypes of SSII mutations in other plants in some respects, however, SSII mutations do not give rise to any lose contents as high as those found in 292/342. SSII mutants are known in pea (rug5, Craig et al., 1998) and Chlamydomonas (Fontaine et al., 1993) and give rise to amylopectins with reduced chain length distributions, as observed here. There is also evidence to suggest that the Shrunken-2 mutation in maize arises through mutation of the SSII gene although this has yet to be conclusively demonstrated (Harn et al., 1998, Knight et al., 1998). In maize, the Shrunken-2 mutation gives rise to starches with reduced gelatinisation temperatures (Campbell et al., 1994). In wheat, Yamamori has developed a triple null line that lacks the Sgp-1 protein (Yamamori 1998) that has been shown by Li et al (Li et al, 1999b) to be the product of the SSII gene. In wheat, amylose content is increased to about 35% and abnormal starch granules, altered crystallinity and altered gelatinisation temperature are observed (Yamamori 1998). The differences in properties between the barley SSII mutants and SSII mutants from other species are quite unexpected.

The SSII mutation has been shown to be able to be transferred by breeding from one genetic background to another and yield diagnostic grain morphology and composition typical of the original 292, 342 and MK6827. In table (9) data from 292× Tantangara doubled haploid lines for the L/T ratio, β-glucan content, chain length distribution, RVA and flour swelling volume parameters demonstrate that lines carrying the 292 mutation show phenotypes typical of the 292 parent. In a further demonstration, the segregation of seed from the selfed progeny of a second backcross of 292 to Sloop showed a segregation ratio consistent with 3:1 segregation for the normal (74 seeds with L/T ratio <3.5) and shrunken phenotypes (21 seeds L/T ratio >3.5).

The availability of the sequence of the SSII gene and barley transformation systems provides the tools required to knock out the SSII gene using gene suppression technologies, in order to produce a comparable phenotype to that found with the SSII mutations. A recently developed highly effective strategy is to produce a hairpin construct designed to produce a double stranded RNA which would suppress the endogenous SSII activity. While complete knock out mutants analogous to the mutations described here would be of interest, the use of DNA constructs with differing promoters, and the recovery of transgenes with differing levels of hairpin construct expression, would allow the impact of titrating the expression of the gene from normal levels to complete knock-down levels to be assessed.

The mutations were shown to be able to be transferred from 292 into alternative barely genetic backgrounds, while retaining essential features of the original 292 mutation. In Tables 9 and 10, phenotypic data for 292× Tantangara doubled haploid progeny, and the seed from a second backcross to Sloop, are shown, and indicate that the phenotypes are transferred through the breeding process.

TABLE 1

Barley Grain Composition

| | Starch Content (%)[a] | Amylose Content By HPLC (%)[b] | Amylose Content by iodine binding (%) | Protein Content (%)[a] | β-glucan (%)[a] | Total Dietary Fibre[a] (%) | Insoluble Dietary Fibre[a] (%) | Soluble Dietary Fibre[a] (%) |
|---|---|---|---|---|---|---|---|---|
| Glacier | n.d. | 31.0 | n.d. | 11.5 | 4.3 | 21.6 | 16.6 | 5 |
| AC38 | 47 | 47.4 | 60.6 | 10.4 | 5.8 | 24.9 | 28.8 | 6.1 |
| Himalaya | 49 | 25 | 25.4 | 10.0 | 4.8 | 27.1 | 18.1 | 9 |
| 292 | 17.7 | 71 | 68.9 | 15.0 | 9.5 | 30.3 | 21.4 | 8.9 |
| 342 | 21.9 | 62.5 | 71.7 | 15.7 | 8.3 | 28.3 | 19.4 | 8.9 |
| MK6827 | 10.2 | n.d. | 44.4 | 21.3 | n.d. | n.d. | n.d. | n.d. |
| Waxiro | 42.8 | n.d. | 5.0 | 14.6 | n.d. | 19.8 | 12.7 | 7.1. |
| Tantangara | 51.6 | n.d. | 29.5 | 14.6 | n.d. | 17.2 | 12.7 | 4.5. |

[a] % grain weight, 14% moisture
[b] % of total starch content
n.d. not determined

TABLE 2

Grain Dimensions

| | Grain weight (mg) | Grain Length (mm) | Grain Width (mm) | Grain Thickness (mm) | L/T Ratio |
|---|---|---|---|---|---|
| Himalaya | 51.01 ± 6.63[a] | 7.01 ± 0.51 | 3.58 ± 0.34 | 2.82 ± 0.36 | 2.48 |
| Tantangara | 50.40 ± 6.51[a] | 7.22 ± 0.98 | 3.60 ± 0.25 | 2.73 ± 0.21 | 2.64 |
| Waxiro | 45.71 ± 5.21 | 7.54 ± 0.47 | 3.40 ± 0.20 | 2.67 ± 0.19 | 2.82 |
| AC38 | 50.79 ± 8.22 | 7.62 ± 0.65 | 3.35 ± 0.27 | 2.64 ± 0.25 | 2.89 |
| 292 | 32.13 ± 4.67[a] | 7.05 ± 0.49 | 3.63 ± 0.55 | 1.58 ± 0.20 | 4.46 |
| 342 | 35.45 ± 6.01 | 7.28 ± 0.55 | 3.76 ± 0.38 | 1.75 ± 0.18 | 4.16 |
| MK6827 | 44.89 ± 3.78 | 11.20 ± 0.58 | 3.63 ± 0.27 | 1.77 ± 0.33 | 6.33 |

N = 50, except where indicated by [a], n = 200

TABLE 3

Chain Length Distribution of Isoamylase Debranched Starches

| Dp[a] | Himalaya %[b] | Tantangara %[b] | AC38 %[b] | 342 %[b] | 292 %[b] | MK6827 %[b] |
|---|---|---|---|---|---|---|
| DP 6-11 | 24.15 | 22.40 | 26.33 | 38.18 | 38.96 | 37.98 |
| DP 12-30 | 69.12 | 67.59 | 67.62 | 54.14 | 53.42 | 55.60 |
| DP 31-60 | 6.73 | 10.01 | 6.05 | 7.68 | 7.62 | 6.42 |

[a]degree of polymerisation
[b]percentage of distribution of oligosaccharides expressed on a molar basis

TABLE 4

Barley Starch Thermal Properties Measured by DSC

| | Peak 1 | | | | Peak 2 | | | |
|---|---|---|---|---|---|---|---|---|
| | Onset | Peak | End | ΔH | Onset | Peak | End | ΔH |
| Glacier | 55.4 | 59.3 | 65.3 | 4.2 | 93.9 | 101.4 | 107.7 | 0.87 |
| AC38 | 55.0 | 62.2 | 68.2 | 3.9 | 89.3 | 100.1 | 106.9 | 1.195 |
| Himalaya | 56.8 | 60.9 | 68.0 | 4.5 | 93.1 | 101.8 | 108.3 | 0.78 |
| 292 | 46.0 | 51.2 | 58.1 | 0.29 | 88.7 | 97.7 | 104.9 | 1.34 |
| 342 | 45.2 | 50.4 | 56.8 | 0.47 | 86.5 | 97.0 | 105.0 | 1.59 |

TABLE 5

RVA Parameters for Barley Starches

| | Peak Viscosity | Breakdown | Holding Strength | Setback | Final Viscosity | Normalised Final Viscosity* | Pasting Temp (C.) |
|---|---|---|---|---|---|---|---|
| Himalaya | 871.5 | 653.1 | 218.4 | 235.8 | 454.2 | 926 | 64.9 |
| Namoi | 621.7 | 367.5 | 254.2 | 375.3 | 629.5 | 1284 | 65.9 |
| AC38 | 226.7 | 87.3 | 139.4 | 188.4 | 327.8 | 697 | 68.9 |
| 292 | 92.1** | *** | 133.9 | 230 | 363.9 | 2055 | 89.5 |
| 342 | 110.9** | *** | 144.9 | 264.5 | 409.4 | 1869 | 87.9 |
| MK6827 | 18.2** | *** | 25.7 | 43.3 | 69 | 676 | n.d. |

*Final viscosity divided by starch content of wholemeal
**Value registered at time of peak viscosity for Himalaya
***Value was less than zero
n.d. not determined

TABLE 6

Starch Crystallinity Data

| Sample | % H2O (W.B) | Crystallinity %* | A %* | B %* | V %* |
|---|---|---|---|---|---|
| 292 | 29.6 | 9 | — | 13 | 87 |
| 342 | 35.8 | 12 | — | 18 | 81 |
| AC38 | 26.1 | 19 | 93 | 7 | (traces) |
| Himalaya | 27.7 | 27 | 93 | 7 | (traces) |
| Waxiro | 29.7 | 41 | 94 | 6 | — |

(*_± 5%)

TABLE 7

Progeny Analysis

| Cross | Shrunken | Full | Calculated $\chi^2$ value[c] |
|---|---|---|---|
| 292 × Sloop[a] | 45 | 155 | $\chi^2$ (3:1) = 1.0 |
| 292 × Tantangara[b] | 45 | 46 | $\chi^2$ (1:1) = 0.01 |

[a]progeny from standard cross
[b]doubled haploid progeny
[c]in each case, $\chi^2$ (0.05), df = 1 = 3.84, hence the 292 × Sloop population fits a 3:1 segregation and 292 × Tantangara doubled haploid population fits a 1:1 segregation

TABLE 8

Scoring of 292 × Tantangara Doubled Haploid Lines

| Line Number[a] | Husk[b] | Seed Weight (mg) | L/T Ratio[c] | DP6-11 (%)[d] | Amylose Content[e] | PCR[f] |
|---|---|---|---|---|---|---|
| 1 | N | 26 | 3.8 | 35.87 | 50.2 | 292 |
| 2 | N | 24 | 4.21 | 36.87 | 56.2 | 292 |

TABLE 8-continued

Scoring of 292 x Tantangara Doubled Haploid Lines

| Line Number[a] | Husk[b] | Seed Weight (mg) | L/T Ratio[c] | DP6-11 (%)[d] | Amylose Content[e] | PCR[f] |
|---|---|---|---|---|---|---|
| 3 | H | 43 | 3.32 | 25.45 | 18.3 | Wt |
| 5 | N | 40 | 4.58 | 39.47 | 55.5 | 292 |
| 7 | N | 34 | 4.28 | 19.63 | 43.0 | 292 |
| 8 | H | 48 | 3.02 | 21.6 | 46.7 | Wt |
| 9 | N | 31 | 2.76 | 22.89 | 25.9 | Wt |
| 10 | N | 26 | 3.02 | 27.56 | 21.1 | Wt |
| 11 | N | 34 | 3.55 | 37.90 | 44.7 | 292 |
| 12 | H | 50 | 2.94 | 26.37 | 32.8 | Wt |
| 13 | N | 27 | 4.29 | 38.68 | 48.4 | 292 |
| 14 | H | 56 | 3.07 | 22.98 | 20.8 | Wt |
| 15 | H | 46 | 2.74 | 24.88 | 22.9 | Wt |
| 16 | H | 43 | 2.78 | 25.40 | 18.3 | Wt |
| 17 | N | 31 | 3.8 | 37.37 | 54.2 | 292 |
| 18 | N | 31 | 4.51 | 37.46 | 57.5 | 292 |
| 19 | H | 26 | 3.1 | 29.57 | 22.7 | Wt |
| 20 | H | 53 | 3.04 | 25.42 | 23.8 | Wt |
| 21 | N | 31 | 4.5 | 38.51 | 59.1 | 292 |
| 22 | N | 27 | 4.63 | 37.25 | 27.2 | 292 |
| 23 | H | 47 | 2.73 | 24.11 | 21.2 | Wt |
| 24 | N | 27 | 4.58 | 36.89 | 42.0 | 292 |
| 26 | H | 35 | 3.57 | 19.50 | 15.1 | Wt |
| 27 | H | 22 | 4.3 | 36.81 | 48.6 | 292 |
| 28 | N | 31 | 4.34 | 38.88 | 37.0 | 292 |
| 30 | N | 30 | 4.04 | 38.05 | 48.4 | 292 |
| 31 | N | 23 | 4.25 | 37.07 | 51.7 | 292 |
| 32 | H | 48 | 2.62 | 20.67 | 13.0 | Wt |
| 33 | N | 25 | 4.92 | 35.68 | 33.3 | 292 |
| 34 | N | 31 | 4.01 | 38.34 | 46.1 | 292 |
| 35 | H | 43 | 3.16 | 20.07 | 23.6 | Wt |
| 36 | N | 26 | 4.33 | 36.93 | 29.7 | 292 |
| 38 | H | 38 | 3.01 | 21.11 | 9.1 | Wt |
| 39 | H | 33 | 2.92 | 20.49 | 23.5 | Wt |
| 40 | H | 36 | 2.99 | 19.57 | 2.2 | Wt |
| 41 | N | 30 | 4.05 | 37.82 | 40.9 | 292 |
| 42 | H | 47 | 2.95 | 20.80 | 11.9 | Wt |
| 43 | N | 40 | 3.24 | 21.97 | 18.1 | Wt |
| 45 | H | 52 | 2.78 | 19.97 | 14.5 | Wt |
| 46 | N | 29 | 4.44 | 35.87 | 32.1 | 292 |
| 47 | N | 35 | 3.69 | 36.34 | 92.9 | 292 |
| 48 | H | 31 | 2.54 | 20.27 | 13.4 | Wt |
| 49 | H | 54 | 2.94 | 22.29 | 19.3 | Wt |
| 50 | H | 50 | 2.94 | 21.92 | 20.6 | Wt |
| 51 | H | 43 | 3.73 | 20.59 | 18.1 | Wt |
| 53 | N | 31 | 4.12 | 36.52 | 55.3 | 292 |
| 54 | N | 34 | 4.02 | 35.17 | 57.1 | 292 |
| 55 | H | 32 | 4.19 | 41.35 | 60.4 | 292 |
| 56 | N | 29 | 3.17 | 21.48 | 18.1 | Wt |
| 57 | H | 30 | 4.85 | 36.66 | 46.3 | 292 |
| 58 | N | 32 | 2.97 | 23.83 | 13.8 | Wt |
| 59 | N | 46 | 2.91 | 24.15 | 9.2 | Wt |
| 60 | H | 44 | 2.74 | 22.39 | 13.5 | Wt |
| 61 | N | 31 | 4.47 | 35.67 | 61.3 | 292 |
| 63 | N | 32 | 4.3 | 36.94 | 39.4 | 292 |
| 64 | H | 39 | 2.93 | 21.95 | 20.5 | Wt |
| 65 | N | 26 | 3.87 | 37.51 | 20.7 | 292 |
| 66 | N | 30 | 4.03 | 36.89 | 48.7 | 292 |
| 67 | H | 36 | 3.17 | 20.24 | 14.4 | Wt |
| 68 | N | 43 | 2.65 | 22.53 | 8.4 | Wt |
| 69 | N | 32 | 3.93 | 36.34 | 54.7 | 292 |
| 70 | H | 43 | 2.77 | 22.28 | 17.6 | Wt |
| 71 | N | 29 | 3.73 | 38.73 | 31.5 | 292 |
| 72 | H | 47 | 2.65 | 22.00 | 20.8 | Wt |
| 73 | N | 36 | 4.09 | 39.58 | 49.0 | 292 |
| 74 | N | 24 | 4.18 | 36.15 | 47.8 | 292 |
| 75 | H | 34 | 2.99 | 24.42 | 14.2 | Wt |
| 76 | N | 31 | 4.35 | 35.95 | 49.9 | 292 |
| 77 | H | 49 | 3.19 | 21.22 | 17.0 | Wt |
| 78 | H | 33 | 2.78 | 21.27 | 15.6 | Wt |
| 79 | H | 31 | 2.85 | 23.04 | 21.2 | Wt |
| 80 | H | 38 | 3.18 | 19.88 | 18.9 | Wt |
| 81 | H | 37 | 2.84 | 24.22 | 16.2 | Wt |
| 82 | H | 33 | 4.64 | 39.99 | 45.3 | 292 |
| 84 | N | 28 | 3.62 | 36.98 | 28.9 | 292 |
| 85 | N | 26 | 6.44 | 44.43 | 41.3 | 292 |
| 86 | H | 32 | 2.87 | 30.73 | 16.1 | Wt |
| 88 | N | 26 | 4.62 | 46.12 | 39.3 | 292 |
| 89 | H | 38 | 2.88 | 31.25 | 16.3 | Wt |
| 90 | H | 32 | 3.19 | 31.11 | 13.8 | Wt |
| 91 | N | 31 | 4.17 | 42.86 | 37.3 | 292 |
| 92 | N | 27 | 3.99 | 45.30 | 44.6 | 292 |
| 93 | H | 37 | 2.99 | 30.77 | 12.5 | Wt |
| 94 | H | 43 | 3.67 | 29.46 | 21.9 | Wt |
| 96 | N | 33 | 5.69 | 47.34 | 52.2 | 292 |
| 97 | N | 23 | 3.41 | 31.36 | 17.1 | Wt |
| 98 | N | 32 | 5.95 | 45.27 | 52.4 | 292 |
| 99 | N | 19 | 3.68 | 38.36 | 1.7 | 292 |
| 100 | H | 36 | 3.1 | 31.92 | 15.4 | Wt |
| 101 | N | 58 | 3.29 | 24.71 | 2.9 | Wt |

[a]292 x Tantangara doubled haploid line
[b]Husk phenotype. N, naked; H, husked
[c]L/T ratio: length to thickness ratio
[d]Percentage of chains in debranched starch with DP6 to DP11, calculated on a molar basis as a percentage of chains eluting between DP6 and DP65
[e]Amylose content determined by iodine blue value
[f]PCR score. 292, PCR reaction yields band which yields 169 bp band plus 103 bp on NlaIV digestion; Wt, PCR reaction yields band which yields 111 bp, 103 bp and 57 bp band on NlaIV digestion

TABLE 9

Detailed Analysis of Doubled Haploid Lines

| Line | L/T Ratio | FACE | RVA Peak Viscosity (RVA Units) | RVA Final Viscosity (RVA Units) | Ratio Peak/Final Viscosities | β-glucan Content (%) | Flour Swelling Volume |
|---|---|---|---|---|---|---|---|
| Control | | | | | | | |
| Sloop | 2.78 | 23.5 | 535.8 | 483.5 | 1.11 | 2.3 | 7.54 |
| Tantangara | 2.64 | 22.4 | 507 | 395.1 | 1.28 | 5.16 | 5.97 |
| Himalaya | 2.48 | 24.2 | 873.9 | 449.3 | 1.94 | 8.53 | 8.18 |
| AC38 | 2.89 | 26.33 | 226.7 | 327.8 | 0.69 | 5.8 | 3.75 |
| 292 | 4.46 | 38.9 | 92.1 | 363.9 | 0.25 | 13.09 | 2.00 |
| MK6827 | 6.33 | 37.98 | 18.2 | 69 | 0.26 | n.d. | 2.11 |

TABLE 9-continued

Detailed Analysis of Doubled Haploid Lines

| Line | L/T Ratio | FACE | RVA Peak Viscosity (RVA Units) | RVA Final Viscosity (RVA Units) | Ratio Peak/Final Viscosities | β-glucan Content (%) | Flour Swelling Volume |
|---|---|---|---|---|---|---|---|
| Doubled Haploid Line Wild Type | | | | | | | |
| 8 | 3.02 | 21.6 | 527.9 | 431.3 | 1.22 | 8.9 | 6.47 |
| 43 | 3.24 | 25.4 | 566.6 | 527.4 | 1.07 | 7.77 | 6.04 |
| 56 | 3.17 | 24.9 | 703.1 | 523.5 | 1.34 | 7.81 | 6.95 |
| 58 | 2.97 | 27.9 | 726.8 | 588.8 | 1.23 | 9.65 | 6.23 |
| 59 | 2.91 | 27.0 | 655 | 435.8 | 1.50 | 7.16 | 7.21 |
| 68 | 2.65 | 22.5 | 876.3 | 465.5 | 1.88 | 8.87 | 8.63 |
| 101 | 3.29 | 34.71 | 471.3 | 410.3 | 1.15 | 6.54 | 6.26 |
| Mutant SSII | | | | | | | |
| 5 | 4.58 | 39.5 | 68.7 | 316.6 | 0.217 | 9.87 | 2.55 |
| 11 | 3.55 | 48.2 | 51.5 | 240.8 | 0.21 | 8.36 | 2.58 |
| 13 | 4.29 | 38.7 | 43.7 | 265.5 | 0.16 | 11.13 | 2.92 |
| 27 | 4.30 | 36.8 | 20.3 | 96.6 | 0.21 | 13.11 | 2.71 |
| 30 | 4.04 | 38.05 | 57.3 | 251.1 | 0.23 | 10.56 | 2.27 |
| 31 | 4.25 | 37.1 | 17.6 | 124.5 | 0.14 | 11.35 | 2.48 |
| 33 | 4.92 | 35.7 | 11.7 | 83.5 | 0.14 | 7.22 | 2.13 |
| 36 | 4.33 | 36.9 | 14.5 | 93.6 | 0.15 | 7.20 | 2.20 |
| 46 | 4.44 | 35.9 | 31.3 | 175.8 | 0.18 | 10.02 | 2.32 |
| 91 | 4.17 | 42.9 | 35.8 | 189.5 | 0.19 | 11.3 | 2.43 | n.d. not determined

TABLE 10

Flour Swelling Data for BC2F2 seed

| Line | Swelling Volume |
|---|---|
| C5/1 Plant 1 L: T > 3.5 | 2.118 |
| C5/1 Plant 1 L: T < 3.5 | 6.913 |
| 65/2 Plant 1 L: T > 3.5 | 2.382 |
| 65/2 Plant 1 L: T < 3.5 | 7.565 |
| 65/2 Plant 2 L: T > 3.5 | 2.409 |
| 65/2 Plant 2 L: T < 3.5 | 6.707 |

Example 2

Design and Construction of Vectors

Figure 15:
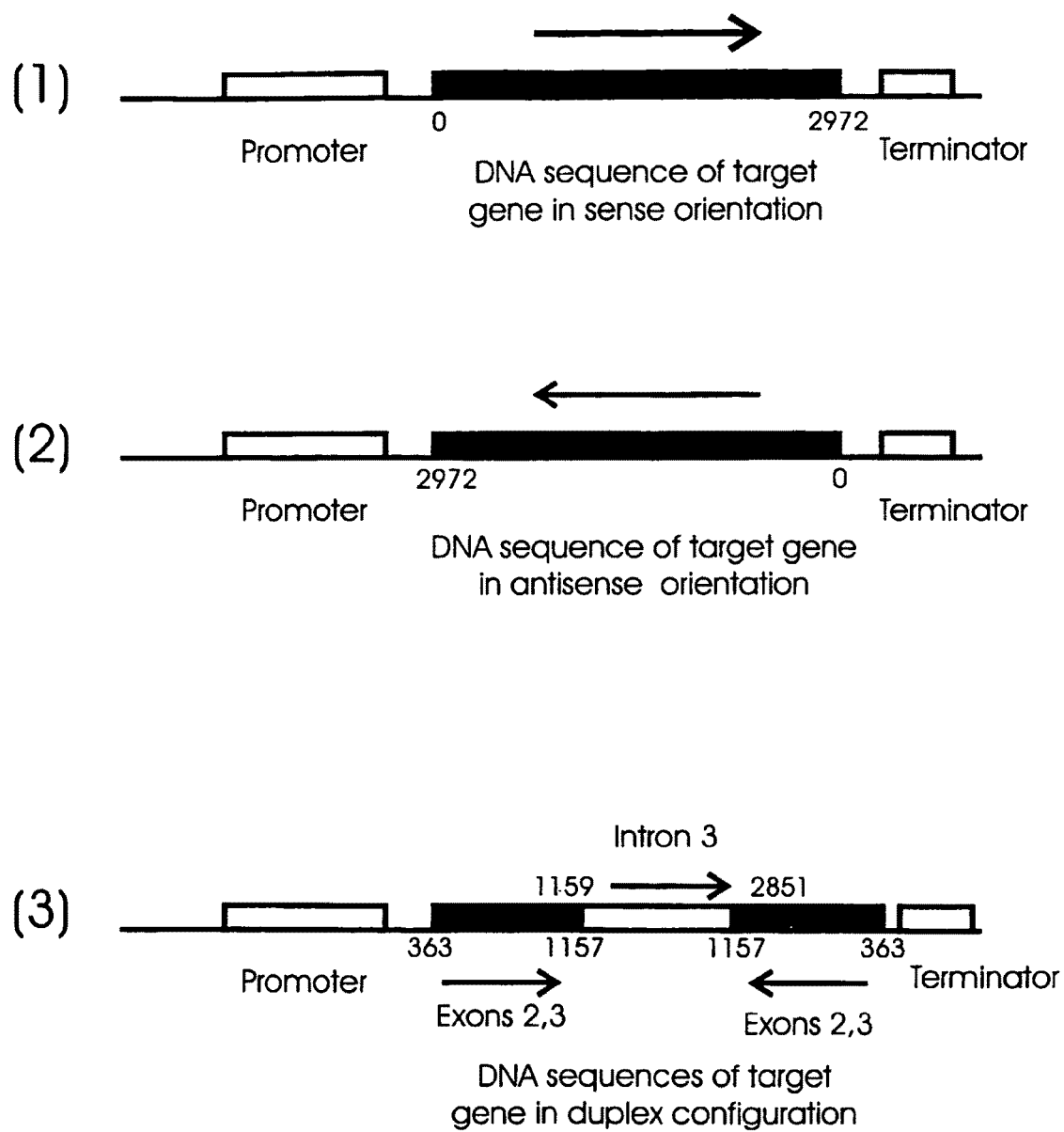
FIG. 15. SDS-PAGE electrophoresis of starch granule proteins. Panel (A) 8% Acrylamide (37.5:1 Acryl/Bis) SDS-PAGE gel, electroblotted and probed with a SSII antibody produced against purified granule-bound SSII protein from Wheat. (B) 12.5% acrylamide (30:0.135 Acryl/Bis), silver stained. The migration of molecular weight standards of defined mass (units are kd) are indicated on each side of the figure.

Regions of the barley SSII gene (as defined in FIG. 15) were cloned into vectors for transformation. Three constructs were prepared for each gene target, addressing the gene suppression strategies, (1) sense cosuppression, (2) antisense and (3) duplex-mediated suppression.

Figure 16:
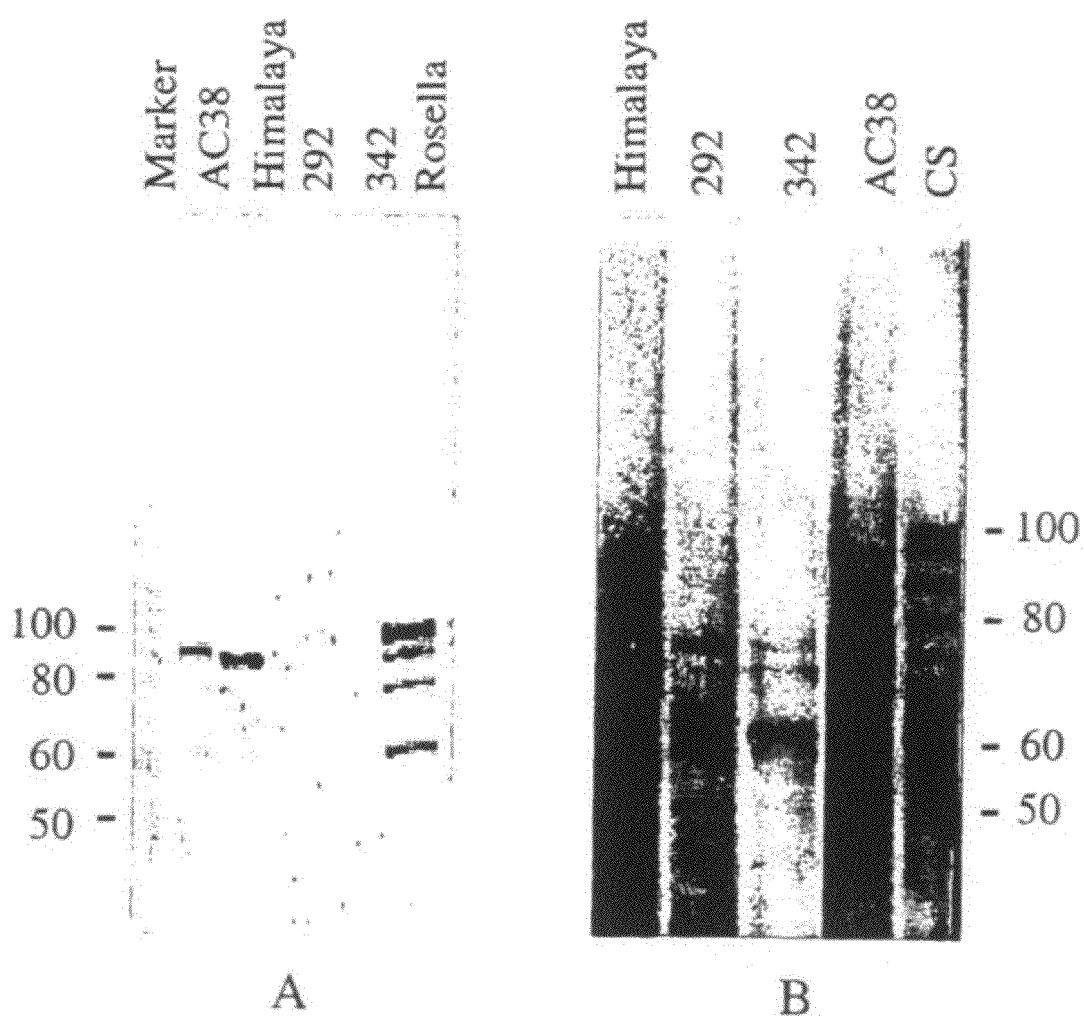
FIG. 16. A schematic representation of DNA constructs designed to down regulate SSII expression following stable transformation of barley (1) The SSII gene from nucleotides 1 to 2972 (see FIG. 9 for sequence) is inserted between the promoter and terminator in the sense orientation. (2) The SSII gene is inserted between the promoter and terminator in the anti-sense orientation from nucleotides 2972 to 1 (see FIG. 9 for sequence). (3) Duplex construct in which intron 3 of the barley SSII gene (between nucleotides 1559 and 2851) of the Morex SSII genomic sequence is inserted between exons 2 and 3 from the barley SSII cDNA from Himalaya (nucleotides 363 to 1157 from FIG. 9).

FIG. 16 illustrates the configuration of sequences in DNA constructs designed to suppress the expression of the endogenous target gene. The promoter may be selected from either endosperm-specific (such as High Molecular Weight Glutenin promoter, the wheat SSI promoter, wheat BEII promoter) or promoters not specific for the endosperm (such as ubiquitin or 35S). The construct may also contain other elements that enhance transcription such as the nos 3 element of OCS. The regions of DNA illustrated will be incorporated into vectors containing suitable selectable marker gene sequences and other elements, or into vectors that are co-transformed with vectors containing these sequences.

Cereal Transformation

Methods for the transformation of barley (Tingay et al., 1997; Wan et al, 1994) oats (Somers et al., 1992, 1994; Gless et al., 1998; Zhang et al., 1999, Cho et al., 1999) and rye (Castillo et al., 1994; Pena et W., 1984) have been described and can be used to transfer DNA constructs generating transgenic plants.

Analysis of Transgenics

Identification of transgenic plants is carried out through identification of the DNA of the DNA construct through PCR or through Southern hybridisation. The levels of the expression of the individual barley starch biosynthetic genes is measured at both the mRNA and protein levels through standard techniques such as Northern hybridisation and Western blotting respectively. The starch and grain content and composition is measured using standard techniques such as those exemplified in Example 1.

REFERENCES

Abel et al., (1996). *The Plant Journal* 10, 981-991.
Ahokas, (1979). *Barley Genetics Newsletter* 9, 7-9
Akerberg et al., (1998). *Journal of Cereal Science* 28, 71-80.
Andersson et al., (2000). *Cereal Chemistry* 77, 463-467
Andersson et al., (1999). *Journal of the science of food and agriculture.* 79, 979-986.
Andreev et al., (1999). *StarchStarke.* 51, 422-429.
Banks et al., (1971). *Starch.* 23, 12-15.
Batey and Curtin. (1997). *Starch* 48, 338-344.
Batey et al., (1997). *Cereal Chemistry* 74, 497-501.
Bergh et al., (1999). *Animal Feed Science and Technology* 78, 215-226.
Bhatty (1999). *Cereal Chemistry* 76, 589-599.
Biyashev et al., (1986). *Soviet Genetics* 22, 296-303.
Boyer and Preiss, (1978). *Carbohydrate Research* 61, 321-334.
Boyer and Preiss, (1981). *Plant Physiology* 67, 1141-1145.
Boye et al., (1980). *Starch* 32, 217-222.
Buleon et al., (1998). *International Journal of Biological Macromolecules* 23, 85-112.
Calvert et al., (1976). *Nutrition Reports. International* 14, 55-61.

Campbell et al., (1994). *Cereal Chemistry* 71, 464-468.
Cao et al., (2000). *Archives. of Biochemistry and Biophysics.* 373, 135-146.
Case et al., (1998). *Journal of Cereal Science* 27, 301-314.
Castillo, et al., (1994). *Bio/technology* 12, 1366-1371.
Cho, et al. (1999). *Plant Science (Limerick)* 148, 9-17.
Craig et al., (1998). *Plant Cell* 10, 413-426.
Czuchajowska et al., (1998). *Cereal Chemistry* 75, 747-754.
Czuchajowska et al., (1992). *Cereal Chemistry* 69, 413-418.
Denyer et al., (1996). *Plant Physiology* 112, 779-785.
Elfverson et al., (1999). *Cereal Chemistry* 76, 434-438.
Eslick and Ries, (1976). *Barley Genetics Newsletter* 6, 21-22.
Fastnaught, et al., (1996). *Crop Science* 36, 941-946.
Fedak et al., (1972). *Canadian Journal of Genetics and Cytology* 14, 949-957.
Filpse et al., (1996). *Planta* 198, 340.
Fontaine et al., (1993). *Journal of Biological Chemistry* 268, 16223-16230.
Fujita et al., (1999) Breeding. Science 49, 217-219.
Fuwa et al., (1999). *Starch/Starke.* 51, 147-151.
Gao et al., (1998). *Plant Cell* 10, 399-412.
Giroux and Hannah. (1994). *Molecular and General Genetics* 243, 400-408.
Gless, et al. (1998). *Journal of Plant Physiology* 152, 151-157.
Goering and DeHaas, (1974). *Cereal Chemistry* 51, 573-578.
Granfeldt et al., (1994). *American Journal of Clinical Nutrition* 59, 1075-1082.
Green et al., (1997). *Plant Physiology* 114, 203-212.
Gubler et al., (2000) *Plant Physiology* 122, 1457
Hedman and Boyer, (1982). *Biochemical Genetics* 20, 483-492.
Izydorczyk et al., (2000). *Journal of Agricultural and Food Chemistry* 48, 982-989.
James et al., (1995). *Plant Cell* 7, 417-429.
Jane et al., (1999). *Cereal Chemistry* 76, 629-637.
Jarvi and Eslick, R. F. (1975). *Crop Science* 15, 363-366.
Jobling et al., (1999). *Plant Journal* 18, 163-171.
Katz et al., (1993). *Carbohydrate polymers* 21, 133-136.
Knight et al., (1998). *Plant Journal* 14, 613-622.
Konik-Rose et al (2001) *Starch* 53, 14-20
Krueger et al., (1987). *Cereal Chemistry* 64, 187-190.
Kubo et al., (1999). *Plant physiology.* 121, 399-409.
Li et al., (1999). *Plant physiology.* 120, 1147-1155.
Li, et al., (2000). *Plant Physiology* 123, 613-624.
Li et al., (1999). *Theoretical and Applied Genetics* 98, 1208-1216.
Mizuno et al., (1993). *Journal of Biological Chemistry* 268, 19084-19091.
Mizuno et al., (1992). *Journal of Biochemistry* 112, 643-651.
Morell et al., (1997). *Plant Physiology* 113, 201-208.
Morell et al., (1998). *Electrophoresis* 19, 2603-2611.
Morrison et al., (1984). *Journal of Cereal Science* 2, 257-271.
Mouille et al., (1996). *The Plant Cell.* 8, 1353-1366.
Myers et al., (2000). *Plant Physiology* 122, 989-997.
Netsvetaev, (1990). *Nauchno-Tekh. Bull' VSG*1, Odessa. No. 1 75, 31-35.
Netsvetaev, (1992). *Cytology and Genetics (Kiev)* 26, 26-30.
Netsvetaev and Krestinkov. (1993). *Barley Genetics Newsletter* 22, 44-45.
Newman et al., (1978). *Journal of Animal Science* 47, 448-455.
Ng et al., (1997). *Cereal Chemistry.* 74, 288-288.
Oscarsson et al., (1998). *Journal of the science of food and agriculture.* 78, 359-366.
Oscarsson et al., (1996). *Journal of Cereal Science* 24, 161-170.
Oscarsson et al., (1997). *Journal of Cereal Science* 26, 259-264.
Pena, et al., (1987). *Nature, UK* 325, 274-276.
Persson and Christerson, (1997). *Sveriges. Utsadesforenings. Tidskrift.* 107, 141-153.
Persson et al., (1996). *Sveriges. Utsadesforenings. Tidskrift.* 106, 79-86.
Pomeranz, (1992). *European. Journal of Clinical. Nutrition* 46, S63-S68.
Pomeranz et al., (1972). *Cereal Chemistry* 49, 629-635.
Rahman et al., (1995). *Australian Journal of Plant Physiology* 22, 793-803.
Ramage and Eslick, (1975). *Barley Genetics Newsletter* 5, 114.
Ramage, and Eslick, (1975). *Barley Genetics Newsletter* 6, 115.
Schondelmaier et al., (1992). *Plant Breeding* 109, 274-280.
Schulman and Kammiovirta, (1991). *Starch* 43, 387-389.
Schwall et al., (2000). *Nature Biotechnology* 18, 551-554.
Shure et al., (1983). *Cell* 35, 225-233.
Somers et al., (1992). Fertile, transgenic oat plants. *Bio/technology* 10, 1589-1594.
Somers, et al. (1994). Genetic engineering of oat. 37-46.
Song and Jane, (2000). *Carbohydrate polymers* 41, 365-377.
Sun et al., (1997). *The New Phytologist* 137, 215-215.
Sundberg et al., (1998). Journal of the Science of Food and Agriculture. 76, 457-463.
Swanston, (1992). *Barley Genetics Newsletter* 22, 66-67.
Swanston et al., (1995). *Journal of Cereal Science* 22, 265-273.
Takeda et al., (1993). *Carbohydrate Research* 246, 273-281.
Thorbjornsen et al., (1996). *Plant Journal* 10, 243-250.
Tingay, et al., (1997). *Plant Journal* 11, 1369-1376.
Topping, (1999). *Asia Pacific Journal of Clinical Nutrition* 8, S22-S26.
Topping et al., (1997). *The Journal of Nutrition* 127, 615-615.
Vasanthan and Bhatty, (1995). *Cereal Chemistry* 72, 379-384.
Vasanthan and Bhatty, (1998). *Starch-Starke.* 50, 286-291.
Walker and Merritt, (1968). *Nature* 221, 482-484.
Wan and Lemaux, (1994). *Plant Physiology* 104, 37-48.
Wang et al., (1998). *Journal of Experimental Botany* 49, 481-502.
Wang, et al., (1993). *Cereal Chemistry* 70, 521-525.
Wilson and McNab, (1975). *British Poultry Science* 16, 497-504.
Xue et al., (1996). *Cereal Chemistry* 73, 588-592.
Yamamori, (1998). (Anon.), pp. 300-302. University Extension Press, University of Saskatchewan, Saskatoon.
Yamamori and Endo, (1996). *Theoretical and Applied Genetics* 93, 275-281.
Yoshimoto et al., (2000). *Cereal Chemistry* 77, 279-285.
Zhang, et al. (1999). *Plant Cell Reports.* 18, 959-966.
Zheng et al., (2000). *Cereal Chemistry* 77, 140-144.
Zwar and Chandler, (1995). *Planta* 197, 39-48.

The invention claimed is:

1. A barley grain comprising a mutant Starch Synthase II (SSII) gene which encodes the amino acid molecule whose sequence is set forth in SEQ ID NO: 7.

2. The barley grain of claim 1, having an amylose content in its starch of higher than 50% (w/w), when determined by size exclusion HPLC in 90% (v/v) DMSO.

3. The barley grain of claim 1 which is milled, ground, pearled, rolled, kibbled, or whole grain.

4. A process of producing the barley grain of claim 1, the process comprising the step of a) obtaining a barley plant capable of producing the barley grain and b) growing the barley plant so obtained to produce the barley grain.

5. A food product comprising the barley grain of claim 1 which is whole, milled, ground, pearled, rolled or kibbled grain, or flour from the grain, wherein the barley grain or flour comprises starch with an amylose content of higher than 50% (w/w), when determined by size exclusion HPLC in 90% (v/v) DMSO.

6. A process for making a food product comprising:
a) obtaining the barley grain of claim 1 having starch with an amylose content of higher than 50% (w/w), when determined by size exclusion HPLC in 90% (v/v) DMSO; and
b) mixing the barley grain or milled, ground, pearled, rolled or kibbled grain, or flour from the grain with a food ingredient to make the food product.

7. A barley plant comprising a mutant Starch Synthase II (SSII) gene which encodes the amino acid molecule whose sequence is set forth in SEQ ID NO: 7.

8. The barley plant of claim 7, wherein a cDNA of the SSII gene has nucleotides in the sequence set forth in SEQ ID NO:1 with the exception that the G at position 1829 is A.

9. A barley grain comprising a mutant Starch Synthase II (SSII) gene, wherein a cDNA of the SSII gene has nucleotides in the sequence set forth in SEQ ID NO: 1 with the exception that the G at position 1829 is A.

10. The barley grain of claim 9, having an amylose content in its starch of higher than 50% (w/w), when determined by size exclusion HPLC in 90% (v/v) DMSO.

11. The barley grain of claim 9, which is milled, ground, pearled, rolled, kibbled, or whole grain.

12. A process of producing the barley grain of claim 9, the process comprising the step of a) obtaining a barley plant capable of producing the barley grain and b) growing the barley plant so obtained to produce the barley grain.

13. A food product comprising the barley grain of claim 9 which is whole, milled, ground, pearled, rolled or kibbled grain, or flour from the grain, wherein the barley grain or flour comprises starch with an amylose content of higher than 50% (w/w), when determined by size exclusion HPLC in 90% (v/v) DMSO.

14. A process for making a food product comprising:
a) obtaining the barley grain of claim 9 having starch with an amylose content of higher than 50% (w/w), when determined by size exclusion HPLC in 90% (v/v) DMSO; and
b) mixing the barley grain or milled, ground, pearled, rolled or kibbled grain, or flour from the grain with a food ingredient to make the food product.

* * * * *

SEQUENCE LISTING

<160> NUMBER OF SEQ ID NOS: 14

<210> SEQ ID NO 1
<211> LENGTH: 2920
<212> TYPE: DNA
<213> ORGANISM: Hordeum vulgare

<400> SEQUENCE: 1

```
cctcgaggtg cgtttacccc acacagagta cactccaact ccagtccaat ccagcccact    60
gccgcttctg cccgcccatc gtaccgtcgc ccgccccgat cccggccgcc gccatgtcgt   120
cggcggtcgc gtccccgcg tccttcctcg cgctcgcgtc cgcctcgccc gggagatcat   180
cacggaggag ggcgagggtg ggcgcgtcgc caacccgcgc tggggccggc aggctgcaat   240
ggcggccgtc gccgctgcag cgcacggctc gcgacggagc ggtggccgcg cgcgccgccg   300
ggatcgacga cgccgcgccc ggtaggcagc ccgcgctcg ccgctatggc gccgccacca   360
aggtcgcgga tcccgtcaag acgctcgatc gcgacgccgc ggaaggtggt gggccgtccc   420
cgccggcacc gaggcaggac gccgcccgtc tgccgagtaa gaacggcacg ctgatcaacg   480
gtgagaacaa acctaccggc ggcggtggcg cgactaaaga cagcgggctt gccacacccg   540
cacgcgcgcc ccatctgtca atccaaaaca gagtaccggt gaacggtgaa acaaacata   600
aggtcgcctc gccgccgacc agcatagtgg atgtcgcgtc tccgggttcc gcagctaaca   660
tttccatcag taacaaggtg ccgccgtccg ttgtcccagc caagaagacg ccgccgtcgt   720
ccgttttccc ggccaagaag acgctgccgt cgtccggctc aaattttgtg tcctcggcct   780
ctgctcccag gctggacact gtcagcgatg tggaacttgc acagaagaag gatgcgctga   840
ttgtcaaaga agctccaaaa ccaaaggctc tttcggcccc tgcagccccc gctgtacaag   900
aagacctttg ggatttcaag aaatacattg gtttcgagga gcccgtggag gccaaggatg   960
atggctcggc tgttgcagat gatgcgggtt cctttgaaca tcaccagaat catgattccg  1020
gacctttggc aggggagaac gtcatgaacg tggtcgtcgt tgctgctgaa tgttctccct  1080
ggtgcaaaac aggtggtctt ggagatgttg cgggtgcttt gcccaaggct ttggctaaga  1140
gaggacatcg tgttatggtt gtggtaccaa ggtatgggga ctatgaggaa gcctacgatg  1200
tcggagtccg aaaatactac aaggctgctg acaggaggat ggaagtgaat tatttccatg  1260
cttatatcga tggagtggat tttgtgttca ttgacgctcc tctcttccga caccgtcagc  1320
aagacattta tggggcagc agacaggaaa ttatgaagcg catgattttg ttctgcaagg  1380
ccgctgtcga ggttccttgg cacgttccat gcggcggtgt cccttacggg gatggaaatc  1440
tggtcttcat tgcaaatgat tggcacacgg cactcctgcc tgtctatctg aaagcatatt  1500
acagggacca tggtttgatg caatacagtc gctccgttat ggtgatacat aacatcgctc  1560
accagggccg tggccctgta gatgaattcc cgttcaccga gttgcctgag cactacctgg  1620
aacacttcag actgtacgac cccgtcggcg gtgagcacgc caactacttc gccgccggcc  1680
tgaagatggc ggaccaggtt gtcgtcgtga gccccgggta cctgtgggag ctgaagacgg  1740
tggagggcgg ctgggggctt cacgacatca tacggcagaa cgactggaag acccgcggca  1800
tcgtgaacgg catcgacaac atggagtgga accctgaggt ggacgtccac ctgaagtcgg  1860
acggctacac caacttctcc ctgaagacgc tggactccgg caagcggcag tgcaaggagg  1920
ccctgcagcg cgagctgggg ctgcaggtcc gggcgacgt gccgctgctc gggttcatcg  1980
ggcggctgga cgggcagaag ggcgtggaga tcatcgcgga cgcgatgccc tggatcgtga  2040
```

```
gccaggacgt gcagctggtg atgctgggca cggggcgcca cgacctggag agcatgctgc    2100
agcacttcga gcgggagcac cacgacaagg tgcgcgggtg ggtggggttc tccgtgcgcc    2160
tggcgcaccg gatcacggcg ggcgccgacg cgctcctcat gccctccgg ttcgagccgt     2220 gcgggctgaa ccagctctac gcgatggcct acggcaccgt ccccgtcgtg cacgccgtcg    2280
gcggcttgag ggataccgtg ccgccgttcg acccttcaa ccactccggg ctcgggtgga     2340
cgttcgaccg cgccgaggcg cacaagctga tcgaggcgct cgggcactgc ctccgcacct    2400
accgggacca aaggagagc tggaggggcc tccaggagcg cggcatgtcg caggacttca     2460
gctgggaaca tgccgccaag ctctacgagg acgtcctcgt ccaggccaag taccagtgg    2520 gaacgctgct acccggtcca gccccgcatg cgtgcatgag aggatggaaa tgcgcattgc    2580
gcacttgcag atttggcgca cgcaggaacg tgccgtcctt cttgatgaga acgccggcat    2640
ccgcgaggtt gagacgctga ttccgatctg gtccgtcgca gagtagagtg aaacgctcct    2700
tgttgcaggt atatgggaat gttttttttc ctttttttt gcgagggagg tatatgggaa    2760
tgttaacttg gtattgtaat gtggtatgct gtgtgcatta ttacatcggt tgttgttgct    2820
tattcttgct agctaagtcg gaggccaaga gcgaaagcta gctcacatgt ctgatgtatg    2880
caagtgacat ggttggtttg aaaaaaaaaa aaaaaaaaaa                           2920

<210> SEQ ID NO 2
<211> LENGTH: 2950
<212> TYPE: DNA
<213> ORGANISM: Hordeum vulgare

<400> SEQUENCE: 2
gtgcgtttac cccacacaga gtacactcca actccagtcc agtccagccc actgccgctt    60
ctgccccgcc atcgtaccgt cgcccgcccc gatcccggcc gccgcatgt cgtcggcggt    120 cgcgtccccc gcgtccttcc tcgcgctcgc gtccgcctcg cccggagat catcacggag    180 gagggcgagg gtgggcgcgt cgccaaccc gctggggcc ggcaggctgc aatgacggcc     240
gtcgccgctg cagcgcacgg ctcgcgacgg agcggtggcc gcgcgcgccg ccgggatcga    300
cgacgccgcg cccggtaggc agccccgcgc tcgccgctat ggcgccgcca ccaaggtcgc    360
ggatcccgtc aagacgctcg atcgcgacgc gcggaaggt ggtgggccgt ccccgccggc     420
accgaggcag gacgccgccc gtctgccgag taagaacggc acgctgatca acggtgagaa    480
caaacctacc ggcggcggtg gcgcgactaa agacagcggg ctgcccacac ccgcacgcgc    540
gccccatctg tcaatccaga acagagtacc ggtgaacggg gaaaacaaac ataaggtcgc    600
ctcgccgccg accagcatag tggatgtcgc gtctccgggt tccgcagcta acatttccat    660
cagtaacaag gtgccgccgt ccgttgtccc agccaagaag acgccgccgt cgtccgtttt    720
cccggccaag aaggcgccgc cgtcgtccgt tgtcccggcc aagaagacgc tgccgtcgtc    780
cggctcaaat tttgtgtcct cggcctctgc tcccaggctg acactgtca gcgatgtgga    840 acttgcacag aagaaggatg cgctgattgt caaagaagct ccaaaaccaa aggctctttc    900
ggcccctgca gccccgctg tacaagaaga cctttggat ttcaagaaat acattggttt      960
cgaggagccc gtggaggcca aggatgatgg ctcggctgtt gcagatgatg cgggttcctt    1020
tgaacatcac cagaatcatg attccggacc tttggcaggg gagaacgtca tgaacgtggt    1080
cgtcgttgct gctgaatgtt ctccctggtg caaaacaggt ggtcttggag atattgcggg    1140
tgctttgccc aaggctttgg ctaagagagg acatcgtgtt atggttgtgg taccaaggta    1200
tggggactat gaggaagcct acgatgtcgg agtccgaaaa tactacaagg ctgctggaca    1260
```

```
ggatatggaa gtgaattatt tccatgctta tatcgatgga gtggattttg tgttcattga   1320
cgctcctctc ttccgacacc gtcagcaaga catttatggg ggcagcagac aggaaattat   1380
gaagcgcatg attttgttct gcaaggccgc tgtcgaggtt ccttggcacg ttccatgcgg   1440
cggtgtccct tacggggatg gaaatctggt cttcattgca aatgattggc acacggcact   1500
cctgcctgtc tatctgaaag catattacag ggaccatggt ttgatgcaat acagtcgctc   1560
cgttatggtg atacataaca tcgctcacca gggccgtggc cctgtagatg aattcccgtt   1620
caccgagttg cctgagcact acctggaaca cttcagactg tacgaccccg tcggcggtga   1680
gcacgccaac tacttcgccg ccggcctgaa gatggcggac caggttgtcg tcgtgagccc   1740
cgggtacctg tgggagctga agacggtgga gggcggctgg gggcttcacg acatcatacg   1800
gcagaacgac tggaagaccc gcggcatcgt gaacggcatc gacaacatgg agtgaaccc    1860 tgaggtggac gtccacctga agtcggacgg ctacaccaac ttctccctga agacgctgga   1920
ctccggcaag cggcagtgca aggaggccct gcagcgcgag ctggggctgc aggtccgcgg   1980
cgacgtgccg ctgctcgggt tcatcgggcg gctggacggg cagaagggcg tggagatcat   2040
cgcggacgcg atgccctgga tcgtgagcca ggacgtgcag ctggtgatgc tgggcacggg   2100
gcgccacgac ctggagagca tgctgcagca cttcgagcgg gagcaccacg acaaggtgcg   2160
cgggtgggtg gggttctccg tgcgcctggc gcaccggatc acggcgggcg ccgacgcgct   2220
cctcatgccc tcccggttcg agccgtgcgg gctgaaccag ctctacgcga tggcctacgg   2280
caccatccct gtcgtgcacg ccgtcggcgg cctgagggat accgtgccgc cgttcgaccc   2340
cttcaaccac tccgggctcg ggtggacgtt cgaccgcgcc gaggcgcaca gctgatcga    2400 ggcgctcggg cactgcctcc gcacctaccg ggaccacaag gagagctgga ggggcctcca   2460
ggagcgcggc atgtcgcagg acttcagctg gaacatgcc gccaagctct acgaggacgt    2520
cctcgtccag gccaagtacc agtggtgaac gctgctaccc ggtccagccc cgcatgcgtg   2580
catgagagga tggaaatgcg cattgcgcac ttgcagattt ggcgcatgca ggaacgtgcc   2640
gtccttcttg atgggaacgc cggcatccgc gaggttgaga cgctgattcc gatctggtcc   2700
gtcgcagagt agagtgaaac gctccttgtt gcaggtatat gggaatgttt tttttttcct   2760 ttttttttt gcgagggagg tatatgggaa tgttaacttg gtattgtaat gtggtatgct    2820
gtgtgcatta ttcatcggt tgttgttgct tattcttgct agctaagtcg gaggccaaga    2880
gcgaaagcta gctcacatgt ctgatgtatg caagtgacat ggttggtttg ttgtgcagt    2940 gcaaacggca                                                        2950
```

<210> SEQ ID NO 3
<211> LENGTH: 2951
<212> TYPE: DNA
<213> ORGANISM: Hordeum vulgare

<400> SEQUENCE: 3

```
gtgcgtttac cccacacaga gtacactcca actccagtcc agtccagccc actgccgctt     60
ctgcccgccc atcgtaccgt cgcccgcccc gatcccggcc gccgccatgt cgtcggcggt   120
cgcgtccccc gcgtccttcc tcgcgctcgc gtccgcctcg cccgggagat catcacggag   180
gagggcgagg gtgggcgcgt cgccaacccg cgctggggcc ggcaggctgc aatggcggcc   240
gtcgccgctg cagcgcacgg ctcgcgacgg agcggtggcc gcgcgcgccg ccgggatcga   300
cgacgccgcg cccggtaggc agcccgcgc tcgccgctat ggcgccgcca ccaaggtcgc    360
ggatcccgtc aagacgctcg atcgcgacgc cgcggaaggt ggtgggccgt ccccgccggc   420
```

-continued

```
accgaggcag gacgccgccc gtctgccgag taagaacggc acgctgatca acggtgagaa    480
caaacctacc ggcggcggtg gcgcgactaa agacagcggg ctgcccacac ccgcacgcgc    540
gccccatctg tcaatccaga acagagtacc ggtgaacggt gaaaacaaac ataaggtcgc    600
ctcgccgccg accagcatag tggatgtcgc gtctccgggt tccgcagcta acatttccat    660
cagtaacaag gtgccgccgt ccgttgtccc agccaagaag acgccgccgt cgtccgtttt    720
cccggccaag aaggcgccgc cgtcgtccgt tgtcccggcc aagaagacgc tgccgtcgtc    780
cggctcaaat tttgtgtcct cggcctctgc tcccaggctg acactgtca gcgatgtgga     840
acttgcacag aagaaggatg cgctgattgt caaagaagct ccaaaaccaa aggctctttc    900
ggcccctgca gccccgctg tacaagaaga cctttgggat tcaagaaat acattggttt     960
cgaggagccc gtgaaggcca aggatgatgg ctcggctgtt gcagatgatg cgggttcctt   1020
tgaacatcac cagaatcatg attccggacc tttggcaggg gagaacgtca tgaacgtggt   1080
cgtcgttgct gctgaatgtt ctccctggtg caaaacaggg ggtcttggag atgttgcggg   1140
tgctttgccc aaggctttgg ctaagagagg acatcgtgtt atggttgtgg taccaaggta   1200
tggggactat gaggaagcct acgatgtcgg agtccgaaaa tactacaagg ctgctggaca   1260
ggatatggaa gtgaattatt tccatgctta tatcgatgga gtggattttg tgttcattga   1320
cgctcctctc ttccgacacc gtcagcaaga catttatggg ggcagcagac aggaaaattat  1380
gaagcgcatg attttgttct gcaaggccgc tgtcgaggtt ccttggcacg ttccatgcgg   1440
cggtgtccct tacggggatg gaaatctggt cttcattgca aatgattggc acacggcact   1500
cctgcctgtc tatctgaaag catattacag ggaccatggt ttgatgcaat acagtcgctc   1560
cgttatggtg atacataaca tcgctcacca gggccgtggc cctgtagatg aattcccgtt   1620
caccgagttg cctgagcact acctggaaca cttcagactg tacgaccccg tcggcggtga   1680
gcacgccaac tacttcgccg ccggcctgaa gatggcggac caggttgtcg tcgtgagccc   1740
cgggtacctg tgggagctga agacggtgga gggcggctgg gggcttcacg acatcatacg   1800
gcagaacgac tggaagaccc gcggcatcgt gaacggcatc gacaacatgg agtgggaaccc  1860
tgaggtggac gtccacctga agtcggacgg ctacaccaac ttctccctga agacgctgga   1920
ctccggcaag cggcagtgca aggaggccct gcagcgcgag ctggggctgc aggtccgcgg   1980
cgacgtgccg ctgctcgggt tcatcgggcg gctggacggg cagaagggcg tggagatcat   2040
cgcggacgcg atgccctgga tcgtgagcca ggacgtgcag ctggtgatgc tgggcacggg   2100
gcgccacgac ctggagagca tgctgcagca cttcagcgg gagcaccacg acaaggtgcg    2160
cgggtgggtg gggttctccg tgcgcctggc gcaccggatc acggcgggcg ccgacgcgct   2220
cctcatgccc tccggttcg agccgtgcgg gctgaaccag ctctacgcga tggcctacgg    2280
caccatccct gtcgtgcacg ccgtcggcgg cctgagggat accgtgccgc cgttcgaccc   2340
cttcaaccac tccgggctcg ggtggacgtt cgaccgcgcc gaggcgcaca agctgatcga   2400
ggcgctcggg cactgcctcc gcacctaccg ggaccacaag gagagctgga ggggcctcca   2460
ggagcgcggc atgtcgcagg acttcagctg ggaacatgcc gccaagctct acgaggacgt   2520
cctcgtccag gccaagtacc agtggtgaac gctgctaccc ggtccagccc cgcatgcgtg   2580
catgagagga tggaaatgcg cattgcgcac ttgcagattt ggcgcatgca ggaacgtgcc   2640
gtccttcttg atgggaacgc cggcatccgc gaggttgaga cgctgattcc gatctggtcc   2700
gtcgcagagt agagtgaaac gctccttgtt gcaggtatat gggaatgttt tttttttcct   2760
ttttttttt tgcgagggag gtatatggga atgttaactt ggtattgtaa tgtggtatgc    2820
```

```
tgtgtgcatt attacatcgg ttgttgttgc ttattcttgc tagctaagtc ggaggccaag   2880
agcgaaagct agctcacatg tctgatgtat gcaagtgaca tggttggttt ggttgtgcag   2940
tgcaaacggc a                                                        2951

<210> SEQ ID NO 4
<211> LENGTH: 2946
<212> TYPE: DNA
<213> ORGANISM: Hordeum vulgare

<400> SEQUENCE: 4
gtgcgtttac cccacacaga gtacactcca actccagtcc agtccagccc actgccgctt     60
ctgcccgccc atcgtaccgt cgcccgcccc gatcccggcc gccgccatgt cgtcggcggt    120
cgcgtccccc gcgtccttcc tcgcgctcgc gtccgcctcg cccgggagat catcacggag    180
gagggcgagg gtgggcgcgt cgccaacccg cgctggggcc ggcaggctgc aatggcggcc    240
gtcgccgctg cagcgcacgg ctcgcgacgg agcggtggcc gcgcgcgccg ccgggatcga    300
cgacgccgcg cccggtaggc agccccgcgc tcgccgctat ggcgccgcca ccaaggtcgc    360
ggatcccgtc aagacgctcg atcgcgacgc gcggaaggt ggtgggccgt ccccgccggc    420
accgaggcag gacgccgccc gtctgccgag taagaacggc acgctgatca acggtgagaa    480
caaacctacc ggcggcggtg gcgcgactaa agacagcggg ctgcccacac ccgcacgcgc    540
gccccatctg tcaatccaga acagagtacc ggtgaacggt gaaaacaaac ataaggtcgc    600
ctcgccgccg accagcatag tggatgtcgc gtctccgggt tccgcagcca acatttccat    660
cagtaacaag gtgccgccgt ccgttgtccc agccaagaag acgccgccgt cgtccgtttt    720
cccggccaag aaggcgccgc cgtcgtccgt tgtcccggcc aagaagacgc tgccgtcgtc    780
cggctcaaat tttgtgtcct cggcctctgc tcccaggctg acactgtca gcgatgtgga    840 acttgcacag aagaaggatg cgctgattgt caaagaagct ccaaaaccaa aggctctttc    900
ggcccctgca gccccgctg tacaagaaga cctttgggat ttcaagaaat acattggttt    960
cgaggagccc gtggaggcca aggatgatgg ctcggctgtt gcagatgatg cgggttcctt   1020
tgaacatcac cagaatcatg attccggacc tttggcaggg gagaacgtca tgaacgtggt   1080
cgtcgttgct gctgaatgtt ctccctggtg caaaacaggt ggtcttggag atgttgcggg   1140
tgctttgccc aaggctttgg ctaagagagg acatcgtgtt atggttgtgg taccaaggta   1200
tggggactat gaggaagcct acgatgtcgg agtccgaaaa tactacaagg ctgctggaca   1260
ggatatggaa gtgaattatt ccatgcttta tatcgatgga gtggattttg tgttcattga   1320
cgctcctctc ttccgacacc gtcagcaaga catttatggg ggcagcagac aggaaattat   1380
gaagcgcatg attttgttct gcaaggccgc tgtcgaggtt ccttggcacg ttccatgcgg   1440
cggtgtccct tacggggatg aaatctggt cttcattgca aatgattggc acacggcact   1500
cctgcctgtc tatctgaaag catattacag ggaccatgtt tgatgcaat acagtcgctc   1560 cgttatggtg atacataaca tcgctcacca gggccgtggc cctgtagatg aattcccgtt   1620
caccgagttg cctgagcact acctggaaca cttcagactg tacgaccccg tcggcggtga   1680
gcacgccaac tacttcgccg ccggcctgaa gatggcggac caggttgtcg tcgtgagccc   1740
cgggtacctg tgggagctga gacggtgga gggcggctgg gggcttcacg acatcatacg   1800
gcagaacgac tggaagaccc gcggcatcgt gaacggcatc gacaacatgg agtgaaaccc   1860
tgaggtggac gtccacctga agtcggacgg ctacaccaac ttctccctga agacgctgga   1920
ctccggcaag cggcagtgca aggaggccct gcagcgcgag ctggggctgc aggtccgcgg   1980
```

-continued

```
cgacgtgccg ctgctcgggt tcatcgggcg gctggacggg cagaagggcg tggagatcat    2040
cgcggacgcg atgccctgga tcgtgagcca ggacgtgcag ctggtgatgc tgggcacggg    2100
gcgccacgac ctggagagca tgctgcagca cttcgagcgg gagcaccacg acaaggtgcg    2160
cgggtgggtg gggttctccg tgcgcctggc gcaccggatc acggcgggcg ccgacgcgct    2220
cctcatgccc tcccggttcg agccgtgcgg gctgaaccag ctctacgcga tggcctacgg    2280
caccatccct gtcgtgcacg ccgtcggcgg cctgagggat accgtgccgc cgttcgaccc    2340
cttcaaccac tccgggctcg gtggacgtt cgaccgcgcc gaggcgcaca agctgatcga    2400
ggcgctcggg cactgcctcc gcacctaccg ggaccacaag gagagctgga ggggcctcca    2460
ggagcgcggc atgtcgcagg acttcagctg gaacatgcc gccaagctct acgaggacgt    2520
cctcgtccag gccaagtacc agtggtgaac gctgctaccc ggtccagccc cgcatgcgtg    2580
catgagagga tggaaatgcg cattgcgcac ttgcagattt ggcgcacgca ggaacgtgcc    2640
gtccttcttg atgagaacgc cggcatccgc gaggttgaga cgctgattcc gatctggtcc    2700
gtcgcagagt agagtgaaac gctccttgtt gcaggtatat gggaatgttt ttttcctttt    2760
ttttttgcga gggaggtata tgggaatgtt aacttggtat tgtaatgtgg tatgctgtgt    2820
gcattattac atcggttgtt gttgcttatt cttgctagct aagtcggagg ccaagagcga    2880
aagctagctc acatgtctga tgtatgcaag tgacatggtt ggtttggttg tgcagtgcaa    2940
acggca                                                              2946
```

<210> SEQ ID NO 5
<211> LENGTH: 802
<212> TYPE: PRT
<213> ORGANISM: Hordeum vulgare

<400> SEQUENCE: 5

```
Met Ser Ser Ala Val Ala Ser Pro Ala Ser Phe Leu Ala Leu Ala Ser
1               5                   10                  15

Ala Ser Pro Gly Arg Ser Ser Arg Arg Ala Arg Val Gly Ala Ser
            20                  25                  30

Pro Thr Arg Ala Gly Ala Gly Arg Leu Gln Trp Arg Pro Ser Pro Leu
        35                  40                  45

Gln Arg Thr Ala Arg Asp Gly Ala Val Ala Ala Arg Ala Gly Ile
    50                  55                  60

Asp Asp Ala Ala Pro Gly Arg Gln Pro Arg Ala Arg Arg Tyr Gly Ala
65                  70                  75                  80

Ala Thr Lys Val Ala Asp Pro Val Lys Thr Leu Asp Arg Asp Ala Ala
                85                  90                  95

Glu Gly Gly Pro Ser Pro Ala Pro Arg Gln Asp Ala Ala Arg
            100                 105                 110

Leu Pro Ser Lys Asn Gly Thr Leu Ile Asn Gly Glu Asn Lys Pro Thr
        115                 120                 125

Gly Gly Gly Gly Ala Thr Lys Asp Ser Gly Leu Pro Thr Pro Ala Arg
    130                 135                 140

Ala Pro His Leu Ser Ile Gln Asn Arg Val Pro Val Asn Gly Glu Asn
145                 150                 155                 160

Lys His Lys Val Ala Ser Pro Pro Thr Ser Ile Val Asp Val Ala Ser
                165                 170                 175

Pro Gly Ser Ala Ala Asn Ile Ser Ile Ser Asn Lys Val Pro Pro Ser
            180                 185                 190

Val Val Pro Ala Lys Lys Thr Pro Pro Ser Ser Val Phe Pro Ala Lys
        195                 200                 205
```

```
Lys Thr Leu Pro Ser Ser Gly Ser Asn Phe Val Ser Ser Ala Ser Ala
    210                 215                 220

Pro Arg Leu Asp Thr Val Ser Asp Val Glu Leu Ala Gln Lys Lys Asp
225                 230                 235                 240

Ala Leu Ile Val Lys Glu Ala Pro Lys Pro Lys Ala Leu Ser Ala Pro
                245                 250                 255

Ala Ala Pro Ala Val Gln Glu Asp Leu Trp Asp Phe Lys Lys Tyr Ile
                260                 265                 270

Gly Phe Glu Glu Pro Val Glu Ala Lys Asp Asp Gly Ser Ala Val Ala
            275                 280                 285

Asp Asp Ala Gly Ser Phe Glu His His Gln Asn His Asp Ser Gly Pro
290                 295                 300

Leu Ala Gly Glu Asn Val Met Asn Val Val Val Ala Ala Glu Cys
305                 310                 315                 320

Ser Pro Trp Cys Lys Thr Gly Gly Leu Gly Asp Val Ala Gly Ala Leu
                325                 330                 335

Pro Lys Ala Leu Ala Lys Arg Gly His Arg Val Met Val Val Val Pro
            340                 345                 350

Arg Tyr Gly Asp Tyr Glu Glu Ala Tyr Asp Val Gly Val Arg Lys Tyr
        355                 360                 365

Tyr Lys Ala Ala Gly Gln Asp Met Glu Val Asn Tyr Phe His Ala Tyr
370                 375                 380

Ile Asp Gly Val Asp Phe Val Phe Ile Asp Ala Pro Leu Phe Arg His
385                 390                 395                 400

Arg Gln Gln Asp Ile Tyr Gly Gly Ser Arg Gln Glu Ile Met Lys Arg
                405                 410                 415

Met Ile Leu Phe Cys Lys Ala Val Glu Val Pro Trp His Val Pro
            420                 425                 430

Cys Gly Gly Val Pro Tyr Gly Asp Gly Asn Leu Val Phe Ile Ala Asn
        435                 440                 445

Asp Trp His Thr Ala Leu Leu Pro Val Tyr Leu Lys Ala Tyr Tyr Arg
450                 455                 460

Asp His Gly Leu Met Gln Tyr Ser Arg Ser Val Met Val Ile His Asn
465                 470                 475                 480

Ile Ala His Gln Gly Arg Gly Pro Val Asp Glu Phe Pro Phe Thr Glu
                485                 490                 495

Leu Pro Glu His Tyr Leu Glu His Phe Arg Leu Tyr Asp Pro Val Gly
            500                 505                 510

Gly Glu His Ala Asn Tyr Phe Ala Ala Gly Leu Lys Met Ala Asp Gln
        515                 520                 525

Val Val Val Ser Pro Gly Tyr Leu Trp Glu Leu Lys Thr Val Glu
530                 535                 540

Gly Gly Trp Gly Leu His Asp Ile Ile Arg Gln Asn Asp Trp Lys Thr
545                 550                 555                 560

Arg Gly Ile Val Asn Gly Ile Asp Asn Met Glu Trp Asn Pro Glu Val
                565                 570                 575

Asp Val His Leu Lys Ser Asp Gly Tyr Thr Asn Phe Ser Leu Lys Thr
            580                 585                 590

Leu Asp Ser Gly Lys Arg Gln Cys Lys Glu Ala Leu Gln Arg Glu Leu
        595                 600                 605

Gly Leu Gln Val Arg Gly Asp Val Pro Leu Leu Gly Phe Ile Gly Arg
610                 615                 620

Leu Asp Gly Gln Lys Gly Val Glu Ile Ile Ala Asp Ala Met Pro Trp
```

```
                            625                 630                 635                 640
        Ile Val Ser Gln Asp Val Gln Leu Val Met Leu Gly Thr Gly Arg His
                        645                 650                 655

Asp Leu Glu Ser Met Leu Gln His Phe Glu Arg Glu His His Asp Lys
                        660                 665                 670

Val Arg Gly Trp Val Gly Phe Ser Val Arg Leu Ala His Arg Ile Thr
                        675                 680                 685

Ala Gly Ala Asp Ala Leu Leu Met Pro Ser Arg Phe Glu Pro Cys Gly
                        690                 695                 700

Leu Asn Gln Leu Tyr Ala Met Ala Tyr Gly Thr Ile Pro Val Val His
        705                 710                 715                 720

Ala Val Gly Gly Leu Arg Asp Thr Val Pro Pro Phe Asp Pro Phe Asn
                        725                 730                 735

His Ser Gly Leu Gly Trp Thr Phe Asp Arg Ala Glu Ala His Lys Leu
                        740                 745                 750

Ile Glu Ala Leu Gly His Cys Leu Arg Thr Tyr Arg Asp His Lys Glu
                        755                 760                 765

Ser Trp Arg Gly Leu Gln Glu Arg Gly Met Ser Gln Asp Phe Ser Trp
                        770                 775                 780

Glu His Ala Ala Lys Leu Tyr Glu Asp Val Leu Val Gln Ala Lys Tyr
        785                 790                 795                 800

Gln Trp

<210> SEQ ID NO 6
<211> LENGTH: 802
<212> TYPE: PRT
<213> ORGANISM: Hordeum vulgare

<400> SEQUENCE: 6

Met Ser Ser Ala Val Ala Ser Pro Ala Ser Phe Leu Ala Leu Ala Ser
        1               5                   10                  15

Ala Ser Pro Gly Arg Ser Ser Arg Arg Ala Arg Val Gly Ala Ser
                        20                  25                  30

Pro Thr Arg Ala Gly Ala Gly Arg Leu Gln Trp Arg Pro Ser Pro Leu
                        35                  40                  45

Gln Arg Thr Ala Arg Asp Gly Ala Val Ala Ala Arg Ala Gly Ile
        50                  55                  60

Asp Asp Ala Ala Pro Gly Arg Gln Pro Arg Ala Arg Arg Tyr Gly Ala
        65                  70                  75                  80

Ala Thr Lys Val Ala Asp Pro Val Lys Thr Leu Asp Arg Asp Ala Ala
                        85                  90                  95

Glu Gly Gly Gly Pro Ser Pro Ala Pro Arg Gln Asp Ala Ala Arg
                        100                 105                 110

Leu Pro Ser Lys Asn Gly Thr Leu Ile Asn Gly Glu Asn Lys Pro Thr
                        115                 120                 125

Gly Gly Gly Gly Ala Thr Lys Asp Ser Gly Leu Pro Thr Pro Ala Arg
                        130                 135                 140

Ala Pro His Leu Ser Ile Gln Asn Arg Val Pro Val Asn Gly Glu Asn
        145                 150                 155                 160

Lys His Lys Val Ala Ser Pro Thr Ser Ile Val Asp Val Ala Ser
                        165                 170                 175

Pro Gly Ser Ala Ala Asn Ile Ser Ile Ser Asn Lys Val Pro Pro Ser
                        180                 185                 190

Val Val Pro Ala Lys Lys Thr Pro Pro Ser Ser Val Phe Pro Ala Lys
                        195                 200                 205
```

```
Lys Thr Leu Pro Ser Ser Gly Ser Asn Phe Val Ser Ser Ala Ser Ala
    210                 215                 220

Pro Arg Leu Asp Thr Val Ser Asp Val Glu Leu Ala Gln Lys Lys Asp
225                 230                 235                 240

Ala Leu Ile Val Lys Glu Ala Pro Lys Pro Lys Ala Leu Ser Ala Pro
                245                 250                 255

Ala Ala Pro Ala Val Gln Glu Asp Leu Trp Asp Phe Lys Lys Tyr Ile
                260                 265                 270

Gly Phe Glu Glu Pro Val Glu Ala Lys Asp Asp Gly Ser Ala Val Ala
            275                 280                 285

Asp Asp Ala Gly Ser Phe Glu His His Gln Asn His Asp Ser Gly Pro
        290                 295                 300

Leu Ala Gly Glu Asn Val Met Asn Val Val Val Ala Ala Glu Cys
305                 310                 315                 320

Ser Pro Trp Cys Lys Thr Gly Gly Leu Gly Asp Val Ala Gly Ala Leu
                325                 330                 335

Pro Lys Ala Leu Ala Lys Arg Gly His Arg Val Met Val Val Val Pro
                340                 345                 350

Arg Tyr Gly Asp Tyr Glu Glu Ala Tyr Asp Val Gly Val Arg Lys Tyr
            355                 360                 365

Tyr Lys Ala Ala Gly Gln Asp Met Glu Val Asn Tyr Phe His Ala Tyr
370                 375                 380

Ile Asp Gly Val Asp Phe Val Phe Ile Asp Ala Pro Leu Phe Arg His
385                 390                 395                 400

Arg Gln Gln Asp Ile Tyr Gly Gly Ser Arg Gln Glu Ile Met Lys Arg
                405                 410                 415

Met Ile Leu Phe Cys Lys Ala Ala Val Glu Val Pro Trp His Val Pro
                420                 425                 430

Cys Gly Gly Val Pro Tyr Gly Asp Gly Asn Leu Val Phe Ile Ala Asn
            435                 440                 445

Asp Trp His Thr Ala Leu Leu Pro Val Tyr Leu Lys Ala Tyr Tyr Arg
450                 455                 460

Asp His Gly Leu Met Gln Tyr Ser Arg Ser Val Met Val Ile His Asn
465                 470                 475                 480

Ile Ala His Gln Gly Arg Gly Pro Val Asp Glu Phe Pro Phe Thr Glu
                485                 490                 495

Leu Pro Glu His Tyr Leu Glu His Phe Arg Leu Tyr Asp Pro Val Gly
            500                 505                 510

Gly Glu His Ala Asn Tyr Phe Ala Ala Gly Leu Lys Met Ala Asp Gln
        515                 520                 525

Val Val Val Ser Pro Gly Tyr Leu Trp Glu Leu Lys Thr Val Glu
530                 535                 540

Gly Gly Trp Gly Leu His Asp Ile Ile Arg Gln Asn Asp Trp Lys Thr
545                 550                 555                 560

Arg Gly Ile Val Asn Gly Ile Asp Asn Met Glu Trp Asn Pro Glu Val
                565                 570                 575

Asp Val His Leu Lys Ser Asp Gly Tyr Thr Asn Phe Ser Leu Lys Thr
            580                 585                 590

Leu Asp Ser Gly Lys Arg Gln Cys Lys Glu Ala Leu Gln Arg Glu Leu
        595                 600                 605

Gly Leu Gln Val Arg Gly Asp Val Pro Leu Leu Gly Phe Ile Gly Arg
    610                 615                 620

Leu Asp Gly Gln Lys Gly Val Glu Ile Ile Ala Asp Ala Met Pro Trp
```

```
                625                 630                 635                 640
Ile Val Ser Gln Asp Val Gln Leu Val Met Leu Gly Thr Gly Arg His
                    645                 650                 655

Asp Leu Glu Ser Met Leu Gln His Phe Glu Arg Glu His His Asp Lys
                660                 665                 670

Val Arg Gly Trp Val Gly Phe Ser Val Arg Leu Ala His Arg Ile Thr
            675                 680                 685

Ala Gly Ala Asp Ala Leu Leu Met Pro Ser Arg Phe Glu Pro Cys Gly
        690                 695                 700

Leu Asn Gln Leu Tyr Ala Met Ala Tyr Gly Thr Ile Pro Val Val His
705                 710                 715                 720

Ala Val Gly Gly Leu Arg Asp Thr Val Pro Pro Phe Asp Pro Phe Asn
                725                 730                 735

His Ser Gly Leu Gly Trp Thr Phe Asp Arg Ala Glu Ala His Lys Leu
                740                 745                 750

Ile Glu Ala Leu Gly His Cys Leu Arg Thr Tyr Arg Asp His Lys Glu
            755                 760                 765

Ser Trp Arg Gly Leu Gln Glu Arg Gly Met Ser Gln Asp Phe Ser Trp
        770                 775                 780

Glu His Ala Ala Lys Leu Tyr Glu Asp Val Leu Val Gln Ala Lys Tyr
785                 790                 795                 800

Gln Trp

<210> SEQ ID NO 7
<211> LENGTH: 571
<212> TYPE: PRT
<213> ORGANISM: Hordeum vulgare

<400> SEQUENCE: 7

Met Ser Ser Ala Val Ala Ser Pro Ala Ser Phe Leu Ala Leu Ala Ser
1               5                   10                  15

Ala Ser Pro Gly Arg Ser Arg Arg Ala Arg Val Gly Ala Ser
                20                  25                  30

Pro Thr Arg Ala Gly Ala Gly Arg Leu Gln Trp Arg Pro Ser Pro Leu
            35                  40                  45

Gln Arg Thr Ala Arg Asp Gly Ala Val Ala Arg Ala Ala Gly Ile
        50                  55                  60

Asp Asp Ala Ala Pro Gly Arg Gln Pro Arg Ala Arg Arg Tyr Gly Ala
65                  70                  75                  80

Ala Thr Lys Val Ala Asp Pro Val Lys Thr Leu Asp Arg Asp Ala Ala
                85                  90                  95

Glu Gly Gly Gly Pro Ser Pro Ala Pro Arg Gln Asp Ala Ala Arg
            100                 105                 110

Leu Pro Ser Lys Asn Gly Thr Leu Ile Asn Gly Glu Asn Lys Pro Thr
        115                 120                 125

Gly Gly Gly Gly Ala Thr Lys Asp Ser Gly Leu Pro Thr Pro Ala Arg
    130                 135                 140

Ala Pro His Leu Ser Ile Gln Asn Arg Val Pro Val Asn Gly Glu Asn
145                 150                 155                 160

Lys His Lys Val Ala Ser Pro Thr Ser Ile Val Asp Val Ala Ser
                165                 170                 175

Pro Gly Ser Ala Ala Asn Ile Ser Ile Ser Asn Lys Val Pro Pro Ser
            180                 185                 190

Val Val Pro Ala Lys Lys Thr Pro Pro Ser Ser Val Phe Pro Ala Lys
        195                 200                 205
```

Lys Thr Leu Pro Ser Ser Gly Ser Asn Phe Val Ser Ala Ser Ala
    210                 215                 220

Pro Arg Leu Asp Thr Val Ser Asp Val Glu Leu Ala Gln Lys Lys Asp
225                 230                 235                 240

Ala Leu Ile Val Lys Glu Ala Pro Lys Pro Lys Ala Leu Ser Ala Pro
                245                 250                 255

Ala Ala Pro Ala Val Gln Glu Asp Leu Trp Asp Phe Lys Lys Tyr Ile
            260                 265                 270

Gly Phe Glu Glu Pro Val Glu Ala Lys Asp Asp Gly Ser Ala Val Ala
        275                 280                 285

Asp Asp Ala Gly Ser Phe Glu His His Gln Asn His Asp Ser Gly Pro
    290                 295                 300

Leu Ala Gly Glu Asn Val Met Asn Val Val Val Ala Ala Glu Cys
305                 310                 315                 320

Ser Pro Trp Cys Lys Thr Gly Gly Leu Gly Asp Val Ala Gly Ala Leu
                325                 330                 335

Pro Lys Ala Leu Ala Lys Arg Gly His Arg Val Met Val Val Val Pro
            340                 345                 350

Arg Tyr Gly Asp Tyr Glu Glu Ala Tyr Asp Val Gly Val Arg Lys Tyr
        355                 360                 365

Tyr Lys Ala Ala Gly Gln Asp Met Glu Val Asn Tyr Phe His Ala Tyr
    370                 375                 380

Ile Asp Gly Val Asp Phe Val Phe Ile Asp Ala Pro Leu Phe Arg His
385                 390                 395                 400

Arg Gln Gln Asp Ile Tyr Gly Gly Ser Arg Gln Glu Ile Met Lys Arg
                405                 410                 415

Met Ile Leu Phe Cys Lys Ala Ala Val Glu Val Pro Trp His Val Pro
            420                 425                 430

Cys Gly Gly Val Pro Tyr Gly Asp Gly Asn Leu Val Phe Ile Ala Asn
        435                 440                 445

Asp Trp His Thr Ala Leu Leu Pro Val Tyr Leu Lys Ala Tyr Tyr Arg
    450                 455                 460

Asp His Gly Leu Met Gln Tyr Ser Arg Ser Val Met Val Ile His Asn
465                 470                 475                 480

Ile Ala His Gln Gly Arg Gly Pro Val Asp Glu Phe Pro Phe Thr Glu
                485                 490                 495

Leu Pro Glu His Tyr Leu Glu His Phe Arg Leu Tyr Asp Pro Val Gly
            500                 505                 510

Gly Glu His Ala Asn Tyr Phe Ala Ala Gly Leu Lys Met Ala Asp Gln
        515                 520                 525

Val Val Val Val Ser Pro Gly Tyr Leu Trp Glu Leu Lys Thr Val Glu
    530                 535                 540

Gly Gly Trp Gly Leu His Asp Ile Ile Arg Gln Asn Asp Trp Lys Thr
545                 550                 555                 560

Arg Gly Ile Val Asn Gly Ile Asp Asn Met Glu
                565                 570

<210> SEQ ID NO 8
<211> LENGTH: 230
<212> TYPE: PRT
<213> ORGANISM: Hordeum vulgare

<400> SEQUENCE: 8

Asn Pro Glu Val Asp Val His Leu Lys Ser Asp Gly Tyr Thr Asn Phe
1               5                   10                  15

Ser Leu Lys Thr Leu Asp Ser Gly Lys Arg Gln Cys Lys Glu Ala Leu
            20                  25                  30

Gln Arg Glu Leu Gly Leu Gln Val Arg Gly Asp Val Pro Leu Leu Gly
            35                  40                  45

Phe Ile Gly Arg Leu Asp Gly Gln Lys Gly Val Glu Ile Ile Ala Asp
    50                  55                  60

Ala Met Pro Trp Ile Val Ser Gln Asp Val Gln Leu Val Met Leu Gly
65                  70                  75                  80

Thr Gly Arg His Asp Leu Glu Ser Met Leu Gln His Phe Glu Arg Glu
                85                  90                  95

His His Asp Lys Val Arg Gly Trp Val Gly Phe Ser Val Arg Leu Ala
            100                 105                 110

His Arg Ile Thr Ala Gly Ala Asp Ala Leu Leu Met Pro Ser Arg Phe
        115                 120                 125

Glu Pro Cys Gly Leu Asn Gln Leu Tyr Ala Met Ala Tyr Gly Thr Ile
130                 135                 140

Pro Val Val His Ala Val Gly Gly Leu Arg Asp Thr Val Pro Pro Phe
145                 150                 155                 160

Asp Pro Phe Asn His Ser Gly Leu Gly Trp Thr Phe Asp Arg Ala Glu
                165                 170                 175

Ala His Lys Leu Ile Glu Ala Leu Gly His Cys Leu Arg Thr Tyr Arg
            180                 185                 190

Asp His Lys Glu Ser Trp Arg Gly Leu Gln Glu Arg Gly Met Ser Gln
        195                 200                 205

Asp Phe Ser Trp Glu His Ala Ala Lys Leu Tyr Glu Asp Val Leu Val
    210                 215                 220

Gln Ala Lys Tyr Gln Trp
225                 230

<210> SEQ ID NO 9
<211> LENGTH: 42
<212> TYPE: PRT
<213> ORGANISM: Hordeum vulgare

<400> SEQUENCE: 9

Met Ser Ser Ala Val Ala Ser Pro Ala Ser Phe Leu Ala Leu Ala Ser
1               5                   10                  15

Ala Ser Pro Gly Arg Ser Ser Arg Arg Ala Arg Val Gly Ala Ser
            20                  25                  30

Pro Thr Arg Ala Gly Ala Gly Arg Leu Gln
        35                  40

<210> SEQ ID NO 10
<211> LENGTH: 759
<212> TYPE: PRT
<213> ORGANISM: Hordeum vulgare

<400> SEQUENCE: 10

Arg Pro Ser Pro Leu Gln Arg Thr Ala Arg Asp Gly Ala Val Ala Ala
1               5                   10                  15

Arg Ala Ala Gly Ile Asp Asp Ala Ala Pro Gly Arg Gln Pro Arg Ala
            20                  25                  30

Arg Arg Tyr Gly Ala Ala Thr Lys Val Ala Asp Pro Val Lys Thr Leu
        35                  40                  45

Asp Arg Asp Ala Ala Glu Gly Gly Gly Pro Ser Pro Ala Pro Arg
    50                  55                  60

```
Gln Asp Ala Ala Arg Leu Pro Ser Lys Asn Gly Thr Leu Ile Asn Gly
 65                  70                  75                  80

Glu Asn Lys Pro Thr Gly Gly Gly Ala Thr Lys Asp Ser Gly Leu
                 85                  90                  95

Pro Thr Pro Ala Arg Ala Pro His Leu Ser Ile Gln Asn Arg Val Pro
                100                 105                 110

Val Asn Gly Glu Asn Lys His Lys Val Ala Ser Pro Thr Ser Ile
            115                 120                 125

Val Asp Val Ala Ser Pro Gly Ser Ala Ala Asn Ile Ser Ile Ser Asn
130                 135                 140

Lys Val Pro Pro Ser Val Val Pro Ala Lys Lys Thr Pro Pro Ser Ser
145                 150                 155                 160

Val Phe Pro Ala Lys Lys Thr Leu Pro Ser Ser Gly Ser Asn Phe Val
                165                 170                 175

Ser Ser Ala Ser Ala Pro Arg Leu Asp Thr Val Ser Asp Val Glu Leu
                180                 185                 190

Ala Gln Lys Lys Asp Ala Leu Ile Val Lys Glu Ala Pro Lys Pro Lys
            195                 200                 205

Ala Leu Ser Ala Pro Ala Ala Pro Ala Val Gln Glu Asp Leu Trp Asp
210                 215                 220

Phe Lys Lys Tyr Ile Gly Phe Glu Pro Val Glu Ala Lys Asp Asp
225                 230                 235                 240

Gly Ser Ala Val Ala Asp Asp Ala Gly Ser Phe Glu His His Gln Asn
                245                 250                 255

His Asp Ser Gly Pro Leu Ala Gly Glu Asn Val Met Asn Val Val
                260                 265                 270

Val Ala Ala Glu Cys Ser Pro Trp Cys Lys Thr Gly Gly Leu Gly Asp
                275                 280                 285

Ile Ala Gly Ala Leu Pro Lys Ala Leu Ala Lys Arg Gly His Arg Val
                290                 295                 300

Met Val Val Val Pro Arg Tyr Gly Asp Tyr Glu Glu Ala Tyr Asp Val
305                 310                 315                 320

Gly Val Arg Lys Tyr Tyr Lys Ala Ala Gly Gln Asp Met Glu Val Asn
                325                 330                 335

Tyr Phe His Ala Tyr Ile Asp Gly Val Asp Phe Val Phe Ile Asp Ala
                340                 345                 350

Pro Leu Phe Arg His Arg Gln Gln Asp Ile Tyr Gly Gly Ser Arg Gln
                355                 360                 365

Glu Ile Met Lys Arg Met Ile Leu Phe Cys Lys Ala Ala Val Glu Val
                370                 375                 380

Pro Trp His Val Pro Cys Gly Gly Val Pro Tyr Gly Asp Gly Asn Leu
385                 390                 395                 400

Val Phe Ile Ala Asn Asp Trp His Thr Ala Leu Leu Pro Val Tyr Leu
                405                 410                 415

Lys Ala Tyr Tyr Arg Asp His Gly Leu Met Gln Tyr Ser Arg Ser Val
                420                 425                 430

Met Val Ile His Asn Ile Ala His Gln Gly Arg Gly Pro Val Asp Glu
                435                 440                 445

Phe Pro Phe Thr Glu Leu Pro Glu His Tyr Leu Glu His Phe Arg Leu
                450                 455                 460

Tyr Asp Pro Val Gly Gly Glu His Ala Asn Tyr Phe Ala Ala Gly Leu
465                 470                 475                 480

Lys Met Ala Asp Gln Val Val Val Ser Pro Gly Tyr Leu Trp Glu
                485                 490                 495
```

```
Leu Lys Thr Val Glu Gly Gly Trp Gly Leu His Asp Ile Ile Arg Gln
            500                 505                 510

Asn Asp Trp Lys Thr Arg Gly Ile Val Asn Gly Ile Asp Asn Met Glu
            515                 520                 525

Trp Asn Pro Glu Val Asp Val His Leu Lys Ser Asp Gly Tyr Thr Asn
530                 535                 540

Phe Ser Leu Lys Thr Leu Asp Ser Gly Lys Arg Gln Cys Lys Glu Ala
545                 550                 555                 560

Leu Gln Arg Glu Leu Gly Leu Gln Val Arg Gly Asp Val Pro Leu Leu
            565                 570                 575

Gly Phe Ile Gly Arg Leu Asp Gly Gln Lys Gly Val Glu Ile Ile Ala
            580                 585                 590

Asp Ala Met Pro Trp Ile Val Ser Gln Asp Val Gln Leu Val Met Leu
            595                 600                 605

Gly Thr Gly Arg His Asp Leu Glu Ser Met Leu Gln His Phe Glu Arg
610                 615                 620

Glu His His Asp Lys Val Arg Gly Trp Val Gly Phe Ser Val Arg Leu
625                 630                 635                 640

Ala His Arg Ile Thr Ala Gly Ala Asp Ala Leu Leu Met Pro Ser Arg
            645                 650                 655

Phe Glu Pro Cys Gly Leu Asn Gln Leu Tyr Ala Met Ala Tyr Gly Thr
            660                 665                 670

Ile Pro Val Val His Ala Val Gly Gly Leu Arg Asp Thr Val Pro Pro
            675                 680                 685

Phe Asp Pro Phe Asn His Ser Gly Leu Gly Trp Thr Phe Asp Arg Ala
690                 695                 700

Glu Ala His Lys Leu Ile Glu Ala Leu Gly His Cys Leu Arg Thr Tyr
705                 710                 715                 720

Arg Asp His Lys Glu Ser Trp Arg Gly Leu Gln Glu Arg Gly Met Ser
            725                 730                 735

Gln Asp Phe Ser Trp Glu His Ala Ala Lys Leu Tyr Glu Asp Val Leu
            740                 745                 750

Val Gln Ala Lys Tyr Gln Trp
            755

<210> SEQ ID NO 11
<211> LENGTH: 23
<212> TYPE: DNA
<213> ORGANISM: Artificial Sequence
<220> FEATURE:
<223> OTHER INFORMATION: Primer ssIIa

<400> SEQUENCE: 11
tgttgaggtt ccatggcacg ttc                                          23

<210> SEQ ID NO 12
<211> LENGTH: 23
<212> TYPE: DNA
<213> ORGANISM: Artificial Sequence
<220> FEATURE:
<223> OTHER INFORMATION: Primer ssIIb

<400> SEQUENCE: 12
agtcgttctg ccgtatgatg tcg                                          23

<210> SEQ ID NO 13
<211> LENGTH: 23
<212> TYPE: DNA
```

```
<213> ORGANISM: Artificial Sequence
<220> FEATURE:
<223> OTHER INFORMATION: Primer ZLSS2P4

<400> SEQUENCE: 13
cctggaacac ttcagactgt acg                                              23

<210> SEQ ID NO 14
<211> LENGTH: 23
<212> TYPE: DNA
<213> ORGANISM: Artificial Sequence
<220> FEATURE:
<223> OTHER INFORMATION: Primer ZLBSSII5

<400> SEQUENCE: 14
cttcagggag aagttggtgt agc                                              23
```